United States Patent
Kelley et al.

(10) Patent No.: US 9,656,063 B2
(45) Date of Patent: May 23, 2017

(54) METHOD AND SYSTEM FOR PLACEMENT OF ELECTRICAL LEAD INSIDE HEART

(71) Applicant: Medtronic, Inc., Minneapolis, MN (US)

(72) Inventors: James F Kelley, Coon Rapids, MN (US); Zhongping Yang, Woodbury, MN (US); Mark T Stewart, Lino Lakes, MN (US)

(73) Assignee: Medtronic, Inc., Minneapolis, MN (US)

( * ) Notice: Subject to any disclaimer, the term of this patent is extended or adjusted under 35 U.S.C. 154(b) by 721 days.

(21) Appl. No.: 13/855,276

(22) Filed: Apr. 2, 2013

(65) Prior Publication Data
US 2013/0296880 A1    Nov. 7, 2013

Related U.S. Application Data

(63) Continuation of application No. 12/570,390, filed on Sep. 30, 2009, now Pat. No. 8,409,219, which is a (Continued)

(51) Int. Cl.
*A61N 1/05* (2006.01)
*A61B 17/12* (2006.01)
(Continued)

(52) U.S. Cl.
CPC .............. *A61N 1/059* (2013.01); *A61B 17/12* (2013.01); *A61B 17/128* (2013.01);
(Continued)

(58) Field of Classification Search
CPC . A61B 17/12; A61B 17/12009; A61B 17/128; A61B 17/3468; A61B 2017/00247; A61B 2017/12018
See application file for complete search history.

(56) References Cited

U.S. PATENT DOCUMENTS 2,371,978 A   3/1945   Perham
2,561,286 A   7/1951   Montgomery
(Continued)

FOREIGN PATENT DOCUMENTS

DE      3527762 A1      2/1987
WO      WO 92/13489     8/1992
(Continued)

OTHER PUBLICATIONS

Avitall et. at., "A Thoracoscopic Approach to Ablate Atrial Fibrillation Via Linear Radiofrequency Lesion Generation on the Epicardium of Both Atria," PACE, Apr. 1996; 19(Part II):626, #241.
(Continued)

*Primary Examiner* — Julie A Szpira
(74) *Attorney, Agent, or Firm* — Carol F. Barry

(57) ABSTRACT

A method of placing an electrical lead of an implantable cardiac device inside a heart of a patient. The method includes securing a tool to an atrial appendage of the heart to hold onto the atrial appendage, piercing the atrial appendage, and creating an aperture in the atrial appendage while holding the atrial appendage with the tool. The method also includes moving a distal end of the electrical lead into the heart through the aperture in the atrial appendage and into a ventricle of the heart. Furthermore, the method includes coupling the distal end of the electrical lead to cardiac tissue in the ventricle and delivering an electrical signal to the cardiac tissue in the ventricle of the heart to maintain a predetermined heartbeat of the heart.

13 Claims, 59 Drawing Sheets

Related U.S. Application Data continuation-in-part of application No. 11/788,261, filed on Apr. 19, 2007, now Pat. No. 8,663,245, and a continuation-in-part of application No. 11/155,699, filed on Jun. 17, 2005, now abandoned.

(60) Provisional application No. 60/795,752, filed on Apr. 28, 2006, provisional application No. 60/685,681, filed on May 27, 2005, provisional application No. 60/581,223, filed on Jun. 18, 2004.

(51) Int. Cl.
  *A61B 17/128* (2006.01)
  *A61B 17/34* (2006.01)
  *A61B 17/00* (2006.01)
  *A61B 18/00* (2006.01)

(52) U.S. Cl.
  CPC .... *A61B 17/12009* (2013.01); *A61B 17/3468* (2013.01); *A61B 2017/00247* (2013.01); *A61B 2017/12018* (2013.01); *A61B 2018/00392* (2013.01)

(56) References Cited

U.S. PATENT DOCUMENTS

| | | |
|---|---|---|
| 2,840,082 A | 6/1958 | Salvatore |
| 3,454,011 A | 7/1969 | Wagner |
| 3,496,932 A | 2/1970 | Prisk et al. |
| 3,736,936 A | 6/1973 | Basiulis et al. |
| 3,807,403 A | 4/1974 | Stumpf et al. |
| 3,823,575 A | 7/1974 | Parel |
| 3,823,715 A | 7/1974 | Tromovitch |
| 3,823,718 A | 7/1974 | Tromovitch |
| 3,827,436 A | 8/1974 | Stumpf et al. |
| 3,830,239 A | 8/1974 | Stumpf |
| 3,841,521 A | 10/1974 | Jarvik |
| 3,854,482 A | 12/1974 | Laugherty et al. |
| 3,856,016 A | 12/1974 | Davis |
| 3,856,018 A | 12/1974 | Perisse et al. |
| 3,859,986 A | 1/1975 | Okada et al. |
| 3,862,627 A | 1/1975 | Hans, Sr. |
| 3,886,945 A | 6/1975 | Stumpf et al. |
| 3,907,339 A | 9/1975 | Stumpf et al. |
| 3,910,277 A | 10/1975 | Zimmer |
| 3,913,581 A | 10/1975 | Ritson et al. |
| 3,924,628 A | 12/1975 | Droegemueller et al. |
| 4,018,227 A | 4/1977 | Wallach |
| 4,022,215 A | 5/1977 | Benson |
| 4,061,135 A | 12/1977 | Widran et al. |
| 4,063,560 A | 12/1977 | Thomas et al. |
| 4,072,152 A | 2/1978 | Linehan |
| 4,082,096 A | 4/1978 | Benson |
| 4,207,897 A | 6/1980 | Lloyd et al. |
| 4,226,239 A | 10/1980 | Polk et al. |
| 4,248,224 A | 2/1981 | Jones |
| 4,274,415 A | 6/1981 | Kanamoto et al. |
| 4,275,734 A | 6/1981 | Mitchiner |
| 4,278,090 A | 7/1981 | Van Gerven |
| 4,374,523 A | 2/1983 | Yoon |
| 4,377,168 A | 3/1983 | Rzasa et al. |
| 4,493,319 A | 1/1985 | Polk et al. |
| 4,519,389 A | 5/1985 | Gudkin et al. |
| 4,598,698 A | 7/1986 | Siegmund |
| 4,601,290 A | 7/1986 | Effron et al. |
| 4,664,110 A | 5/1987 | Schanzlin |
| 4,736,749 A | 4/1988 | Lundback |
| 4,779,611 A | 10/1988 | Grooters et al. |
| 4,791,707 A | 12/1988 | Tucker |
| 4,802,475 A | 2/1989 | Weshahy |
| 4,815,470 A | 3/1989 | Curtis et al. |
| 4,872,346 A | 10/1989 | Kelly-Fry et al. |
| 4,916,922 A | 4/1990 | Mullens |
| 4,917,095 A | 4/1990 | Fry et al. |
| 4,917,677 A | 4/1990 | McCarthy |
| 4,936,281 A | 6/1990 | Stasz |
| 4,946,460 A | 8/1990 | Merry et al. |
| 5,013,312 A | 5/1991 | Parins et al. |
| 5,029,574 A | 7/1991 | Shimamura et al. |
| 5,044,165 A | 9/1991 | Linner et al. |
| 5,078,713 A | 1/1992 | Varney |
| 5,080,102 A | 1/1992 | Dory |
| 5,080,660 A | 1/1992 | Buelina |
| 5,100,388 A | 3/1992 | Behl et al. |
| 5,108,390 A | 4/1992 | Potocky et al. |
| 5,119,804 A | 6/1992 | Anstadt |
| 5,147,355 A | 9/1992 | Friedman et al. |
| 5,178,133 A | 1/1993 | Pena |
| 5,207,674 A | 5/1993 | Hamilton |
| 5,217,473 A | 6/1993 | Yoon |
| 5,217,860 A | 6/1993 | Fahy et al. |
| 5,222,501 A | 6/1993 | Ideker et al. |
| 5,224,943 A | 7/1993 | Goddard |
| 5,228,923 A | 7/1993 | Hed |
| 5,231,995 A | 8/1993 | Desai |
| 5,232,516 A | 8/1993 | Hed |
| 5,254,116 A | 10/1993 | Baust et al. |
| 5,263,493 A | 11/1993 | Avitall |
| 5,269,291 A | 12/1993 | Carter |
| 5,275,595 A | 1/1994 | Dobak, III |
| 5,277,201 A | 1/1994 | Stern |
| 5,281,213 A | 1/1994 | Milder et al. |
| 5,281,215 A | 1/1994 | Milder |
| 5,282,829 A | 2/1994 | Hermes |
| 5,295,484 A | 3/1994 | Marcus et al. |
| 5,306,234 A | 4/1994 | Johnson |
| 5,309,896 A | 5/1994 | Moll et al. |
| 5,316,000 A | 5/1994 | Chapelon et al. |
| 5,317,878 A | 6/1994 | Bradshaw et al. |
| 5,318,525 A | 6/1994 | West et al. |
| 5,322,520 A | 6/1994 | Milder |
| 5,323,781 A | 6/1994 | Ideker et al. |
| 5,324,255 A | 6/1994 | Passafaro et al. |
| 5,324,284 A | 6/1994 | Imran |
| 5,324,286 A | 6/1994 | Fowler |
| 5,334,181 A | 8/1994 | Rubinsky et al. |
| 5,334,193 A | 8/1994 | Nardella |
| 5,334,209 A | 8/1994 | Yoon |
| 5,336,252 A | 8/1994 | Cohen |
| 5,348,554 A | 9/1994 | Imran et al. |
| 5,353,783 A | 10/1994 | Nakao et al. |
| 5,354,258 A | 10/1994 | Dory |
| 5,361,752 A | 11/1994 | Moll et al. |
| 5,366,459 A | 11/1994 | Yoon |
| 5,383,917 A | 1/1995 | Desai et al. |
| 5,385,148 A | 1/1995 | Lesh et al. |
| 5,396,887 A | 3/1995 | Imran |
| 5,397,304 A | 3/1995 | Truckai |
| 5,400,770 A | 3/1995 | Nakao et al. |
| 5,400,783 A | 3/1995 | Pomeranz et al. |
| 5,403,309 A | 4/1995 | Coleman et al. |
| 5,403,311 A | 4/1995 | Abele et al. |
| 5,405,376 A | 4/1995 | Mulier et al. |
| 5,409,483 A | 4/1995 | Campbell et al. |
| 5,423,807 A | 6/1995 | Milder |
| 5,423,811 A | 6/1995 | Imran et al. |
| 5,425,740 A | 6/1995 | Hutchinson, Jr. |
| 5,427,119 A | 6/1995 | Swartz et al. |
| 5,431,649 A | 7/1995 | Mulier et al. |
| 5,433,708 A | 7/1995 | Nichols et al. |
| 5,435,308 A | 7/1995 | Gallup et al. |
| 5,437,651 A | 8/1995 | Todd et al. |
| 5,443,463 A | 8/1995 | Stern et al. |
| 5,443,470 A | 8/1995 | Stern et al. |
| 5,450,843 A | 9/1995 | Moll et al. |
| 5,452,582 A | 9/1995 | Longsworth |
| 5,452,733 A | 9/1995 | Sterman et al. |
| 5,462,545 A | 10/1995 | Wang et al. |
| 5,465,717 A | 11/1995 | Imran et al. |
| 5,469,853 A | 11/1995 | Law et al. |
| 5,472,876 A | 12/1995 | Fahy |
| 5,478,309 A | 12/1995 | Sweezer et al. |
| 5,478,330 A | 12/1995 | Imran et al. |

(56) References Cited

U.S. PATENT DOCUMENTS

| | | | |
|---|---|---|---|
| 5,486,193 A | 1/1996 | Bourne et al. |
| 5,487,385 A | 1/1996 | Avitall |
| 5,487,757 A | 1/1996 | Truckai et al. |
| 5,496,312 A | 3/1996 | Klicek |
| 5,497,774 A | 3/1996 | Swartz et al. |
| 5,498,248 A | 3/1996 | Milder |
| 5,500,012 A | 3/1996 | Brucker et al. |
| 5,505,730 A | 4/1996 | Edwards |
| 5,516,505 A | 5/1996 | McDow |
| 5,520,682 A | 5/1996 | Baust et al. |
| 5,522,870 A | 6/1996 | Ben-Zion |
| 5,536,267 A | 7/1996 | Edwards et al. |
| 5,545,195 A | 8/1996 | Lennox et al. |
| 5,545,200 A | 8/1996 | West et al. |
| 5,549,661 A | 8/1996 | Kordis et al. |
| 5,555,883 A | 9/1996 | Avitall |
| 5,558,671 A | 9/1996 | Yates |
| 5,560,362 A | 10/1996 | Sliwa, Jr. et al. |
| 5,562,720 A | 10/1996 | Stern et al. |
| 5,569,241 A | 10/1996 | Edwards |
| 5,571,088 A | 11/1996 | Lennox et al. |
| 5,571,215 A | 11/1996 | Sterman et al. |
| 5,573,532 A | 11/1996 | Chang et al. |
| 5,575,766 A | 11/1996 | Swartz et al. |
| 5,575,788 A | 11/1996 | Baker et al. |
| 5,575,810 A | 11/1996 | Swanson et al. |
| 5,578,007 A | 11/1996 | Imran |
| 5,582,609 A | 12/1996 | Swanson et al. |
| 5,588,432 A | 12/1996 | Crowley |
| 5,590,657 A | 1/1997 | Cain et al. |
| 5,595,183 A | 1/1997 | Swanson et al. |
| 5,607,462 A | 3/1997 | Imran |
| 5,617,854 A | 4/1997 | Munsif |
| 5,620,452 A | 4/1997 | Yoon |
| 5,630,837 A | 5/1997 | Crowley |
| 5,637,090 A | 6/1997 | McGee et al. |
| 5,643,197 A | 7/1997 | Brucker et al. |
| 5,656,029 A | 8/1997 | Imran et al. |
| 5,658,278 A | 8/1997 | Imran et al. |
| 5,667,518 A | 9/1997 | Pannell |
| 5,671,747 A | 9/1997 | Conner |
| 5,673,695 A | 10/1997 | McGee et al. |
| 5,676,662 A | 10/1997 | Fleischhacker et al. |
| 5,676,692 A | 10/1997 | Sanghvi et al. |
| 5,676,693 A | 10/1997 | Lafontaine |
| 5,678,550 A | 10/1997 | Bassen et al. |
| 5,680,860 A | 10/1997 | Imran |
| 5,681,278 A | 10/1997 | Igo et al. |
| 5,681,308 A | 10/1997 | Edwards et al. |
| 5,687,723 A | 11/1997 | Avitall |
| 5,687,737 A | 11/1997 | Branham et al. |
| 5,688,267 A | 11/1997 | Panescu et al. |
| 5,690,611 A | 11/1997 | Swartz et al. |
| 5,697,536 A | 12/1997 | Eggers et al. |
| 5,697,882 A | 12/1997 | Eggers et al. |
| 5,697,925 A | 12/1997 | Taylor |
| 5,697,927 A | 12/1997 | Imran et al. |
| 5,697,928 A | 12/1997 | Walcott et al. |
| 5,713,942 A | 2/1998 | Stern |
| 5,716,389 A | 2/1998 | Walinsky et al. |
| 5,718,241 A | 2/1998 | Ben-Haim et al. |
| 5,718,701 A | 2/1998 | Shai et al. |
| 5,720,775 A | 2/1998 | Lanard |
| 5,722,402 A | 3/1998 | Swanson et al. |
| 5,730,074 A | 3/1998 | Peter |
| 5,730,127 A | 3/1998 | Avitall |
| 5,730,704 A | 3/1998 | Avitall |
| 5,733,280 A | 3/1998 | Avitall |
| 5,735,280 A | 4/1998 | Sherman et al. |
| 5,735,290 A | 4/1998 | Sterman et al. |
| 5,755,760 A | 5/1998 | Maguire et al. |
| 5,766,216 A | 6/1998 | Gangal et al. |
| 5,769,846 A | 6/1998 | Edwards et al. |
| 5,782,828 A | 7/1998 | Chen et al. |
| 5,785,706 A | 7/1998 | Bednarek |
| 5,788,636 A | 8/1998 | Curley |
| 5,792,140 A | 8/1998 | Tu et al. |
| 5,797,960 A | 8/1998 | Stevens et al. |
| 5,800,428 A | 9/1998 | Nelson et al. |
| 5,800,482 A | 9/1998 | Pomeranz et al. |
| 5,810,802 A | 9/1998 | Panescu et al. |
| 5,824,032 A * | 10/1998 | Belden .................. A61N 1/057 |
| | | | 604/179 |
| 5,827,216 A | 10/1998 | Igo et al. |
| 5,836,947 A | 11/1998 | Fleischman et al. |
| 5,840,030 A | 11/1998 | Ferek-Petric et al. |
| 5,844,349 A | 12/1998 | Oakley et al. |
| 5,846,187 A | 12/1998 | Wells et al. |
| 5,846,191 A | 12/1998 | Wells et al. |
| 5,849,028 A | 12/1998 | Chen |
| 5,865,791 A | 2/1999 | Whayne et al. |
| 5,871,523 A | 2/1999 | Fleischman et al. |
| 5,871,525 A | 2/1999 | Edwards et al. |
| 5,873,845 A | 2/1999 | Cline et al. |
| 5,876,399 A | 3/1999 | Chia et al. |
| 5,879,295 A | 3/1999 | Li et al. |
| 5,879,296 A | 3/1999 | Ockuly et al. |
| 5,881,732 A | 3/1999 | Sung et al. |
| 5,882,346 A | 3/1999 | Pomeranz et al. |
| 5,885,278 A | 3/1999 | Fleischman |
| 5,893,848 A | 4/1999 | Negus et al. |
| 5,895,417 A | 4/1999 | Pomeranz et al. |
| 5,897,553 A | 4/1999 | Mulier |
| 5,897,554 A | 4/1999 | Chia et al. |
| 5,899,898 A | 5/1999 | Arless et al. |
| 5,899,899 A | 5/1999 | Arless et al. |
| 5,902,289 A | 5/1999 | Swartz et al. |
| 5,904,680 A | 5/1999 | Kordis et al. |
| 5,904,711 A | 5/1999 | Flom et al. |
| 5,906,580 A | 5/1999 | Kline-Schoder et al. |
| 5,906,587 A | 5/1999 | Zimmon |
| 5,906,606 A | 5/1999 | Chee et al. |
| 5,908,029 A | 6/1999 | Knudson et al. |
| 5,908,435 A | 6/1999 | Samuels |
| 5,916,213 A | 6/1999 | Haissaguerre et al. |
| 5,916,214 A | 6/1999 | Cosio et al. |
| 5,921,924 A | 7/1999 | Avitall |
| 5,921,982 A | 7/1999 | Lesh et al. |
| 5,927,284 A | 7/1999 | Borst et al. |
| 5,928,191 A | 7/1999 | Houser et al. |
| 5,931,810 A | 8/1999 | Grabek |
| 5,931,848 A | 8/1999 | Saadat |
| 5,954,661 A | 9/1999 | Greenspon et al. |
| 5,971,980 A | 10/1999 | Sherman |
| 5,971,983 A | 10/1999 | Lesh |
| 5,976,158 A * | 11/1999 | Adams ............. A61B 17/12013 |
| | | | 606/140 |
| 5,984,917 A | 11/1999 | Fleischman et al. |
| 5,993,447 A | 11/1999 | Blewett et al. |
| 6,007,499 A | 12/1999 | Martin et al. |
| 6,012,457 A | 1/2000 | Lesh |
| 6,016,811 A | 1/2000 | Knopp et al. |
| 6,042,556 A | 3/2000 | Beach et al. |
| 6,042,563 A | 3/2000 | Morejohn et al. |
| 6,059,778 A | 5/2000 | Sherman |
| 6,063,081 A | 5/2000 | Mulier |
| 6,071,279 A | 6/2000 | Whayne et al. |
| 6,071,281 A | 6/2000 | Burnside et al. |
| 6,088,894 A | 7/2000 | Oakley |
| 6,096,037 A | 8/2000 | Mulier |
| 6,113,592 A | 9/2000 | Taylor |
| 6,113,609 A | 9/2000 | Adams |
| 6,117,101 A | 9/2000 | Diederich et al. |
| 6,120,496 A | 9/2000 | Whayne et al. |
| 6,142,993 A | 11/2000 | Whayne et al. |
| 6,142,994 A | 11/2000 | Swanson et al. |
| 6,152,144 A | 11/2000 | Lesh et al. |
| 6,152,920 A | 11/2000 | Thompson et al. |
| 6,152,936 A | 11/2000 | Christy et al. |
| 6,161,543 A | 12/2000 | Cox et al. |
| 6,162,184 A | 12/2000 | Swanson et al. |
| 6,164,283 A | 12/2000 | Lesh |
| 6,165,174 A | 12/2000 | Jacobs et al. |
| 6,200,314 B1 | 3/2001 | Sherman |

(56) References Cited

U.S. PATENT DOCUMENTS

| | | |
|---|---|---|
| 6,217,528 B1 | 4/2001 | Koblish et al. |
| 6,217,576 B1 | 4/2001 | Tu et al. |
| 6,224,592 B1 | 5/2001 | Eggers et al. |
| 6,231,518 B1 | 5/2001 | Grabek et al. |
| 6,231,561 B1 | 5/2001 | Frazier et al. |
| 6,235,024 B1 | 5/2001 | Tu |
| 6,237,605 B1 | 5/2001 | Vaska et al. |
| 6,238,347 B1 | 5/2001 | Nix et al. |
| 6,238,393 B1 | 5/2001 | Mulier |
| 6,241,754 B1 | 6/2001 | Swanson et al. |
| 6,245,061 B1 | 6/2001 | Panescu et al. |
| 6,245,064 B1 | 6/2001 | Lesh et al. |
| 6,245,065 B1 | 6/2001 | Panescu et al. |
| 6,251,092 B1 | 6/2001 | Qin et al. |
| 6,251,128 B1 | 6/2001 | Knopp et al. |
| 6,270,471 B1 | 8/2001 | Hechel et al. |
| 6,280,415 B1 | 8/2001 | Johnson |
| 6,290,674 B1 | 9/2001 | Roue et al. |
| 6,293,943 B1 | 9/2001 | Panescu et al. |
| 6,296,619 B1 | 10/2001 | Brisken et al. |
| 6,302,880 B1 | 10/2001 | Schaer |
| 6,311,692 B1 | 11/2001 | Vaska et al. |
| 6,312,383 B1 | 11/2001 | Lizzi et al. |
| 6,314,962 B1 | 11/2001 | Vaska et al. |
| 6,314,963 B1 | 11/2001 | Vaska et al. |
| 6,325,797 B1 | 12/2001 | Stewart et al. |
| 6,328,736 B1 | 12/2001 | Mulier |
| 6,332,881 B1 | 12/2001 | Carner et al. |
| 6,358,248 B1 | 3/2002 | Mulier |
| 6,361,531 B1 | 3/2002 | Hissong |
| 6,364,876 B1 | 4/2002 | Erb et al. |
| 6,368,275 B1 | 4/2002 | Sliwa et al. |
| 6,371,955 B1 | 4/2002 | Fuimaono et al. |
| 6,379,366 B1 * | 4/2002 | Fleischman ...... A61B 17/00234 606/139 |
| 6,383,151 B1 | 5/2002 | Diederich et al. |
| 6,385,472 B1 | 5/2002 | Hall et al. |
| 6,398,792 B1 | 6/2002 | O'Connor |
| 6,401,720 B1 | 6/2002 | Stevens et al. |
| 6,409,722 B1 | 6/2002 | Hoey |
| 6,413,254 B1 | 7/2002 | Hissong et al. |
| 6,416,554 B1 | 7/2002 | Alferness et al. |
| 6,419,648 B1 | 7/2002 | Vitek et al. |
| 6,419,669 B1 | 7/2002 | Frazier et al. |
| 6,425,867 B1 | 7/2002 | Vaezy et al. |
| 6,428,548 B1 | 8/2002 | Durgin et al. |
| 6,430,426 B2 | 8/2002 | Avitall |
| 6,436,088 B2 | 8/2002 | Frazier et al. |
| 6,440,130 B1 | 8/2002 | Mulier |
| 6,443,952 B1 | 9/2002 | Mulier |
| 6,447,507 B1 | 9/2002 | Bednarek et al. |
| 6,458,100 B2 | 10/2002 | Roue et al. |
| 6,461,314 B1 | 10/2002 | Pant et al. |
| 6,461,356 B1 | 10/2002 | Patterson |
| 6,464,700 B1 | 10/2002 | Koblish et al. |
| 6,471,697 B1 | 10/2002 | Lesh |
| 6,471,698 B1 | 10/2002 | Edwards et al. |
| 6,474,340 B1 | 11/2002 | Vaska et al. |
| 6,475,216 B2 | 11/2002 | Mulier |
| 6,477,396 B1 | 11/2002 | Mest et al. |
| 6,484,727 B1 | 11/2002 | Vaska et al. |
| 6,485,407 B2 | 11/2002 | Alferness et al. |
| 6,488,678 B2 | 12/2002 | Sherman |
| 6,488,680 B1 | 12/2002 | Francischelli |
| 6,488,689 B1 | 12/2002 | Kaplan |
| 6,491,706 B1 | 12/2002 | Alferness et al. |
| 6,500,172 B1 | 12/2002 | Panescu et al. |
| 6,502,575 B1 | 1/2003 | Jacobs et al. |
| 6,503,247 B2 | 1/2003 | Swartz et al. |
| 6,514,250 B1 | 2/2003 | Jahns |
| 6,527,767 B2 | 3/2003 | Wang et al. |
| 6,537,248 B2 | 3/2003 | Mulier et al. |
| 6,537,272 B2 | 3/2003 | Christopherson et al. |
| 6,551,303 B1 | 4/2003 | Van Tassel et al. |
| 6,558,378 B2 | 5/2003 | Sherman et al. |
| 6,558,382 B2 | 5/2003 | Jahns et al. |
| 6,582,423 B1 | 6/2003 | Thapliyal et al. |
| 6,584,360 B2 | 6/2003 | Francischelli |
| 6,585,732 B2 | 7/2003 | Mulier |
| 6,605,084 B2 | 8/2003 | Acker et al. |
| 6,610,055 B1 | 8/2003 | Swanson et al. |
| 6,610,060 B2 | 8/2003 | Mulier et al. |
| 6,610,072 B1 | 8/2003 | Christy et al. |
| 6,613,048 B2 | 9/2003 | Mulier |
| 6,641,557 B1 | 11/2003 | Frazier et al. |
| 6,645,199 B1 | 11/2003 | Jenkins et al. |
| 6,648,883 B2 | 11/2003 | Francischelli et al. |
| 6,652,555 B1 | 11/2003 | Van Tassel et al. |
| 6,652,556 B1 | 11/2003 | Van Tassel et al. |
| 6,656,175 B2 | 12/2003 | Francischelli et al. |
| 6,663,627 B2 | 12/2003 | Francischelli et al. |
| 6,666,861 B1 | 12/2003 | Grabek |
| 6,689,150 B1 | 2/2004 | Van Tassel et al. |
| 6,692,450 B1 | 2/2004 | Coleman |
| 6,699,240 B2 | 3/2004 | Francischelli |
| 6,702,811 B2 | 3/2004 | Stewart et al. |
| 6,702,825 B2 | 3/2004 | Frazier et al. |
| 6,706,038 B2 | 3/2004 | Francischelli |
| 6,706,039 B2 | 3/2004 | Mulier et al. |
| 6,712,804 B2 | 3/2004 | Roue et al. |
| 6,716,211 B2 | 4/2004 | Mulier |
| 6,723,094 B1 | 4/2004 | Desinger |
| 6,730,108 B2 * | 5/2004 | Van Tassel ....... A61B 17/12022 604/104 |
| 6,736,810 B2 | 5/2004 | Hoey et al. |
| 6,755,827 B2 | 6/2004 | Mulier et al. |
| 6,764,487 B2 | 7/2004 | Mulier et al. |
| 6,773,433 B2 | 8/2004 | Stewart et al. |
| 6,776,780 B2 | 8/2004 | Mulier et al. |
| 6,793,664 B2 | 9/2004 | Mazzocchi et al. |
| 6,807,968 B2 | 10/2004 | Francischelli et al. |
| 6,827,715 B2 | 12/2004 | Francischelli et al. |
| 6,832,996 B2 | 12/2004 | Woloszko et al. |
| 6,849,073 B2 | 2/2005 | Hoey et al. |
| 6,849,075 B2 | 2/2005 | Bertolero et al. |
| 6,849,078 B2 | 2/2005 | Durgin et al. |
| 6,858,028 B2 | 2/2005 | Mulier et al. |
| 6,887,238 B2 | 5/2005 | Jahns et al. |
| 6,899,711 B2 | 5/2005 | Stewart et al. |
| 6,905,498 B2 | 6/2005 | Hooven |
| 6,911,019 B2 | 6/2005 | Mulier et al. |
| 6,916,318 B2 | 7/2005 | Francischelli et al. |
| 6,936,046 B2 | 8/2005 | Hissong et al. |
| 6,949,097 B2 | 9/2005 | Stewart et al. |
| 6,949,098 B2 | 9/2005 | Mulier et al. |
| 6,955,173 B2 | 10/2005 | Lesh |
| 6,960,205 B2 | 11/2005 | Jahns et al. |
| 6,962,589 B2 | 11/2005 | Mulier et al. |
| 6,966,908 B2 | 11/2005 | Maguire et al. |
| 7,013,169 B2 | 3/2006 | Bowe |
| 7,020,518 B2 * | 3/2006 | Zheng ................. A61N 1/0563 607/5 |
| 7,044,135 B2 | 5/2006 | Lesh |
| 7,048,734 B1 | 5/2006 | Fleischman et al. |
| 7,052,492 B2 | 5/2006 | Swanson et al. |
| 7,115,122 B1 | 10/2006 | Swanson et al. |
| 7,226,458 B2 * | 6/2007 | Kaplan ................. A61B 17/12 606/139 |
| 7,344,544 B2 | 3/2008 | Bender et al. |
| 7,429,261 B2 | 9/2008 | Kunis et al. |
| 8,097,015 B2 | 1/2012 | Devellian |
| 8,409,219 B2 | 4/2013 | Kelley et al. |
| 2001/0025132 A1 | 9/2001 | Alferness et al. |
| 2001/0039434 A1 | 11/2001 | Frazier et al. |
| 2001/0039435 A1 | 11/2001 | Roue et al. |
| 2001/0041914 A1 | 11/2001 | Frazier et al. |
| 2001/0041915 A1 | 11/2001 | Roue et al. |
| 2002/0022860 A1 | 2/2002 | Borillo et al. |
| 2002/0035374 A1 | 3/2002 | Borillo et al. |
| 2002/0049457 A1 | 4/2002 | Kaplan et al. |
| 2002/0062130 A1 | 5/2002 | Jugenheimer et al. |
| 2002/0072757 A1 | 6/2002 | Ahmed et al. |
| 2002/0099390 A1 | 7/2002 | Kaplan et al. |
| 2002/0103492 A1 | 8/2002 | Kaplan et al. |

(56) References Cited

U.S. PATENT DOCUMENTS

| | | |
|---|---|---|
| 2002/0111637 A1 | 8/2002 | Kaplan et al. |
| 2002/0111641 A1 | 8/2002 | Peterson et al. |
| 2002/0111647 A1 | 8/2002 | Khairkhahan et al. |
| 2002/0169377 A1 | 11/2002 | Khairkhahan et al. |
| 2002/0177859 A1 | 11/2002 | Monassevitch et al. |
| 2003/0018362 A1 | 1/2003 | Fellows et al. |
| 2003/0023266 A1 | 1/2003 | Borillo et al. |
| 2003/0045872 A1 | 3/2003 | Jacobs et al. |
| 2003/0055422 A1 | 3/2003 | Lesh |
| 2003/0069593 A1 | 4/2003 | Tremulis et al. |
| 2003/0120337 A1 | 6/2003 | Van Tassel et al. |
| 2003/0144656 A1 | 7/2003 | Ocel et al. |
| 2003/0158464 A1 | 8/2003 | Bertolero |
| 2003/0181942 A1 | 9/2003 | Sutton et al. |
| 2003/0191462 A1 | 10/2003 | Jacobs et al. |
| 2003/0191526 A1 | 10/2003 | Van Tassel et al. |
| 2003/0195555 A1 | 10/2003 | Khairkhahan et al. |
| 2003/0199923 A1 | 10/2003 | Khairkhahan et al. |
| 2003/0204203 A1 | 10/2003 | Khairkhaahan et al. |
| 2003/0212432 A1 | 11/2003 | Khairkhahan et al. |
| 2003/0216724 A1 | 11/2003 | Jahns |
| 2003/0220658 A1 | 11/2003 | Hatch et al. |
| 2003/0220667 A1 | 11/2003 | van der Burg et al. |
| 2004/0015106 A1 | 1/2004 | Coleman |
| 2004/0015219 A1 | 1/2004 | Francischelli |
| 2004/0030335 A1* | 2/2004 | Zenati .............. A61B 17/12013 606/51 |
| 2004/0034366 A1 | 2/2004 | van der Burg et al. |
| 2004/0044340 A1 | 3/2004 | Francischelli et al. |
| 2004/0044361 A1 | 3/2004 | Frazier et al. |
| 2004/0049179 A1 | 3/2004 | Francischelli et al. |
| 2004/0049210 A1 | 3/2004 | Van Tassel et al. |
| 2004/0064138 A1 | 4/2004 | Grabek |
| 2004/0073241 A1 | 4/2004 | Barry et al. |
| 2004/0078069 A1 | 4/2004 | Francischelli et al. |
| 2004/0082948 A1 | 4/2004 | Stewart et al. |
| 2004/0087940 A1 | 5/2004 | Jahns et al. |
| 2004/0092926 A1 | 5/2004 | Hoey et al. |
| 2004/0098031 A1 | 5/2004 | van der Burg et al. |
| 2004/0098047 A1 | 5/2004 | Frazier et al. |
| 2004/0122467 A1 | 6/2004 | Van Tassel et al. |
| 2004/0127935 A1 | 7/2004 | Van Tassel et al. |
| 2004/0138621 A1 | 7/2004 | Jahns et al. |
| 2004/0138656 A1 | 7/2004 | Francischelli et al. |
| 2004/0143260 A1 | 7/2004 | Francischelli |
| 2004/0147973 A1 | 7/2004 | Hauser |
| 2004/0186465 A1 | 9/2004 | Francischelli et al. |
| 2004/0186486 A1* | 9/2004 | Roue .............. A61B 17/00234 606/139 |
| 2004/0215183 A1 | 10/2004 | Hoey et al. |
| 2004/0215230 A1 | 10/2004 | Frazier et al. |
| 2004/0220560 A1 | 11/2004 | Briscoe |
| 2004/0225212 A1 | 11/2004 | Okerlund et al. |
| 2004/0230222 A1 | 11/2004 | van der Burg et al. |
| 2004/0236322 A1 | 11/2004 | Mulier et al. |
| 2004/0267326 A1 | 12/2004 | Ocel et al. |
| 2005/0004652 A1 | 1/2005 | van der Burg et al. |
| 2005/0010095 A1 | 1/2005 | Stewart et al. |
| 2005/0033280 A1 | 2/2005 | Francischelli et al. |
| 2005/0033287 A1 | 2/2005 | Sra |
| 2005/0038470 A1 | 2/2005 | van der Burg et al. |
| 2005/0049573 A1 | 3/2005 | Van Tassel et al. |
| 2005/0070925 A1 | 3/2005 | Shelton et al. |
| 2005/0070952 A1* | 3/2005 | Devellian .......... A61B 17/0057 606/200 |
| 2005/0085883 A1 | 4/2005 | Ollivier et al. |
| 2005/0090815 A1 | 4/2005 | Francischelli et al. |
| 2005/0137669 A1* | 6/2005 | Krishnan .............. A61N 1/056 607/122 |
| 2005/0143729 A1 | 6/2005 | Francischelli et al. |
| 2005/0149068 A1 | 7/2005 | Williams et al. |
| 2005/0149069 A1 | 7/2005 | Bertolero et al. |
| 2005/0165392 A1 | 7/2005 | Francischelli et al. |
| 2005/0177176 A1 | 8/2005 | Gerbi et al. |
| 2005/0209564 A1 | 9/2005 | Bonner et al. |
| 2005/0267454 A1 | 12/2005 | Hissong et al. |
| 2005/0277959 A1 | 12/2005 | Cosgrove et al. |
| 2006/0009756 A1 | 1/2006 | Francischelli et al. |
| 2006/0009759 A1 | 1/2006 | Chrisitian et al. |
| 2006/0020271 A1 | 1/2006 | Stewart et al. |
| 2006/0041300 A1 | 2/2006 | Zhang et al. |
| 2006/0111700 A1 | 5/2006 | Kunis et al. |
| 2006/0111701 A1 | 5/2006 | Oral et al. |
| 2006/0111702 A1 | 5/2006 | Oral et al. |
| 2006/0111703 A1 | 5/2006 | Kunis et al. |
| 2007/0129753 A1 | 6/2007 | Quinn et al. |
| 2007/0135826 A1 | 6/2007 | Zaver et al. |
| 2007/0197921 A1 | 8/2007 | Cohen et al. |
| 2007/0225734 A1* | 9/2007 | Bell ................ A61B 17/12013 606/139 |
| 2007/0270891 A1 | 11/2007 | McGuckin, Jr. |
| 2008/0033241 A1* | 2/2008 | Peh ...................... A61B 1/0008 600/109 |
| 2008/0033457 A1 | 2/2008 | Francischelli et al. |
| 2008/0039879 A1 | 2/2008 | Chin et al. |
| 2008/0125795 A1 | 5/2008 | Kaplan et al. |
| 2008/0243183 A1 | 10/2008 | Miller et al. |
| 2008/0294175 A1 | 11/2008 | Bardsley et al. |
| 2008/0312664 A1 | 12/2008 | Bardsley et al. |
| 2010/0042110 A1 | 2/2010 | Kelley et al. |
| 2010/0228221 A1* | 9/2010 | Kassab ............. A61B 17/0057 604/500 |
| 2011/0130744 A1* | 6/2011 | Kassab ............. A61B 17/0057 604/508 |

FOREIGN PATENT DOCUMENTS

| | | |
|---|---|---|
| WO | WO 98/18389 | 5/1998 |
| WO | WO 99/62409 | 12/1999 |
| WO | WO 00/74745 | 12/2000 |
| WO | WO 01/35832 | 5/2001 |
| WO | WO 01/97696 | 12/2001 |
| WO | WO 03/011150 | 2/2003 |
| WO | WO 03/096881 | 11/2003 |

OTHER PUBLICATIONS

Avitall et at., "New Monitoring Criteria for Transmural Ablation of Atrial Tissues," Circulation, 1996; 94(Supp 1):1-493, #2889.

Blackshear et al., "Appendage Obliteration to Reduce Stroke in Cardiac Surgical Patients with Atrial Fibrillation," Ann. Thorac. Surg., 1996; 61:755-759.

Bredikis and Bredikis; Surgery of Tachyarrhythmia: Intracardiac Closed Heart Cryoablation; PACE, Dec. 1990; 13:1980-1984.

Chitwood, "Will C. Sealy, MD: The Father of Arrhythmia Surgery—The Story of the Fisherman with a Fast Pulse," Annals of Thoracic Surgery, 58:1228-1239, 1994.

Cox et al., "Surgery for Atrial Fibrillation," Seminars in Thoracic and Cardiovascular Surgery, Jul. 1989; 1(1):67-73.

Cox et al., "Modification of the Maze Procedure for Atrial Flutter and Atrial Fibrillation. I. Rational and Surgical Results," The Journal of Thoracic Cardiovascular Surgery, 110:473-484, 1995.

Cox, "The Maze III Procedure for Treatment of Atrial Fibrillation," Sabiston DC, ed., Atlas of Cardiothoracic Surgery, Philadelphia, WB Saunders, 460-475, 1994.

Cox et al., "The Surgical Treatment of Atrial Fibrillation, IV Surgical Technique," J of Thorac Cardiovasc Surg, 1991; 101:584-593.

Cox, "Evolving Applications of the Maze Procedure for Atrial Fibrillation," Ann Thorac Surg, 1993; 55:578-580.

Cox et al. "Five-Year Experience with the Maze Procedure for Atrial Fibrillation," Ann Thorac Surg, 1993; 56:814-824.

Cox et al., "An 8 1/2 Year Clinical Experience with Surgery for Atrial Fibrillation," Annals of Surgery, 1996; 224(3):267-275.

Cox, et al., "Perinodal cryosurgery for atrioventricular node reentry tachycardia in 23 patients," Journal of Thoracic and Cardiovascular Surgery, Mar. 1990; 99(3):440-450.

Cox, "Anatomic-Electrophysiologic Basis for the Surgical Treatment of Refractory Ischemic Ventricular Tachycardia," Annals of Surgery, Aug. 1983; 198(2):119-129.

(56) References Cited

OTHER PUBLICATIONS

Cox, "Surgical Treatment of Atrial Fibrillation: A Review," Europace, 2004; 5 Suppl 1:S20-S29.

DiSesa et al., "Ligation of the Left Atrial Appendage using an Automatic Surgical Stapler," The Annals of Thoracic Surgery, Dec. 1988; 46(6):652-653.

Elvan et al., "Radiofrequency Catheter Ablation of the Atria Reduces Inducibility and Duration of Atrial Fibrillation in Dog," Circulation, 91:2235-2244, 1995.

Fischer, et al., "Left Atrial Appendage Occlusion to Prevent Stroke in Suboptimal Warfarin Candidates: Current Results of the European Multicenter Registry Trial," American College of Cardiology, Abstract presented at 2005 National Meeting, Mar. 6-9, 2005, Orlando, Florida. Published in JACC, Feb. 2005; 45(3) Supplement, p. 14A, Abstract No. 1116-6.

Gallagher et al., "Cryosurgical Ablation of Accessory Atrioventrical Connections: A Method for Correction of the Pre-excitation Syndrome," Circulation, 55(3): 471-479, 1977.

Gallagher et al., "Surgical Treatment of Arrhythmias," The American Journal of Cardiology, 61(2):A27-A44, 1988.

Graffigna et al., "Surgical Treatment of Wolff-Parkinson-White Syndrome: Epicardial Approach Without the Use of Cardiopulmonary Bypass," Journal of Cardiac Surgery, 8(2):108-116, 1993.

Guiraudon et al., "Surgical Repair of Wolff-Parkinson-White Syndrome: A New Closed-Heart Technique," The Annals of Thoracic Surgery, 37(1):67-71, 1984.

Guiraudon et al., "Surgical Ablation of Posterior Septal Accessory Pathways in the Wolf-Parkinson-White Syndrome by a Closed Heart Technique," Journal of Thoracic Cardiovascular Surgery, 92:406-413, 1986.

Haissaguerre et al., "Radiofrequency Catheter Ablation for Paroxysmal Atrial Fibrillation in Humans: Elaboration of a procedure based on electrophysiological data," Nonpharmacological Management of Atrial Fibrillation, 1997, pp. 257-279.

Haissaguerre et al., "Right and Left Atrial Radiofrequency Catheter Therapy of Paroxysmal Atrial Fibrillation," Journal of Cardiovascular Electrophysiology, 1996; 7(12):1132-1144.

Haissaguerre et al., "Role of Catheter Ablation for Atrial Fibrillation," Current Opinion in Cardiology, 1997; 12:18-23.

Jais et al., "Catheter Ablation for Paroxysmal Atrial Fibrillation: High Success Rates with Ablation in the Left Atrium," Circulation (Nov. 1996) 94:1-675, #3946.

Katz et al., "Surgical Left Atrial Appendage Ligation is Frequently Incomplete: A Transesophageal Echocardiographic Study," Journal of the American College of Cardiology, Aug. 2000; 36(2):468-471.

Kawaguchi et al., "Risks and Benefits of Combined Maze Procedure for Atrial Fibrillation Associated with Organic Heart Disease," JACC, 1996; 28(4):985-990.

Klein et al., "Surgical Correction of the Wolff-Parkinson-White Syndrome in the Closed Heart Using Cryosurgery: A Simplified Approach," JACC, 3(2):405-409, 1984.

Kosakai et al., "Cox Maze Procedure for Chronic Atrial Fibrillation Associated with Mitral Valve Disease," The Journal of Thoracic Cardiovascular Surgery, 108: 1049-1055, 1994.

Krum et al., "Visualization of Remnants of the Left Atrial Appendage following Epicardial Surgical Removal," Heart Rhythm, 2004; 1(2):249.

Krumsdorf et al., "Incidence and Clinical Course of Thrombus Formation on Atrial Septal Defect and Patient Foramen Ovale Closure Devices in 1,000 Consecutive Patients," J. Am. Coll. Cardio., Jan. 21, 2004; 43(2):302-309.

Mahomed et al., "Surgical Division of Wolff-Parkinson-White Pathways Utilizing the Closed-Heart Technique: A 2-Year Experience in 47 Patients," The Annals of Thoracic Surgery, 45(5):495-504, 1988.

McCarthy et al., "Combined Treatment of Mitral Regurgitation and Atrial Fibrillation with Valvuloplasty and the Maze Procedure," The American Journal of Cardiology, 71:483-486, 1993.

Nardella, "Radio Frequency Energy and Impedance Feedback," SPIE Proceedings, vol. 1068, 42 (Aug. 8, 1989); Catheter-Based Sensing and Imaging Technology Conference, Jan. 15, 1989, Los Angeles, California.

Odell, et al., "Thoracoscopic Obliteration of the Left Atrial Appendage: Potential for Stroke Reduction," Ann. Thorac. Surg., 1996, 61:565-569.

Olinger, "Carbon dioxide displacement of left heart chambers," J. Thorac. Cardiovasc. Surg., 1995, 109:187-188.

Randall et al., "Local Epicardial Chemical Ablation of Vagal Input to Sino-Atrial and Atrioventricular Regions of the Canine Heart," Journal of the Autonomic Nervous System, 11(2):145-159, 1984.

Scheinman, "Catheter-based Techniques for Cure of Cardiac Arrhythmias," Advances in Cardiovascular Medicine, 1996, ISSN 1075-5527, pp. 93-100.

Sealy, "Direct Surgical Treatment of Arrhythmias: The Last Frontier in Surgical Cardiology," Chest, 75(5):536-537, 1979.

Sealy, "The Evolution of the Surgical Methods for Interruption of Right Free Wall Kent Bundles," The Annals of Thoracic Surgery, 36(1):29-36, 1983.

Sharafuddin et al., "Transvenous Closure of Secundum Atrial Septal Defects: Preliminary Results With a New Self-Expanding Nitinol Prosthesis in a Swine Model," Circulation, 1997; 95:2162-2168.

Sie et at., "Radiofrequency Ablation of Atrial Fibrillation in Patients Undergoing Mitral Valve Surgery. First Experience," Circulation, Nov. 1996; 96:450, 1-675, #3946.

Sie et al., "Radiofrequency Ablation of Atrial Fibrillation in Patients Undergoing Valve Surgery," Circulation, Nov. 1997; 84:I450, #2519.

Siefert et al., "Radiofrequency Maze Ablation for Atrial Fibrillation," Circulation 90(4): I-594.

Sievert et al., "Percutaneous Left Atrial Appendage Transcatheter Occlusion to Prevent Stroke in High-Risk Patients with Atrial Fibrillation," Circulation, 2002, 105:1887-1889.

Sueda et al., "Simple Left Atrial Procedure for Chronic Atrial Fibrillation Associated with Mitral Valve Disease," The Annals of Thoracic Surgery, 62(6): 1796-1800, 1996.

Sueda et al., "Efficacy of a Simple Left Atrial Procedure for Chronic Atrial Fibrillation in Mitral Valve Operations," Ann Thorac Surg, 1997; 63:1070-1075.

Tsui et al., "Maze 3 for Atrial Fibrillation: Two Cuts Too Few?" PACE, 17:2163-2166, 1994.

Williams, et al., "Left atrial isolation," J Thorac Cardiovasc Surg, 1980; 80:373-380.

Yamauchi et al. "Use of Intraoperative Mapping to Optimize Surgical Ablation of Atrial Flutter," The Annals of Thoracic Surgery, 56: 337-342, 1993.

\* cited by examiner

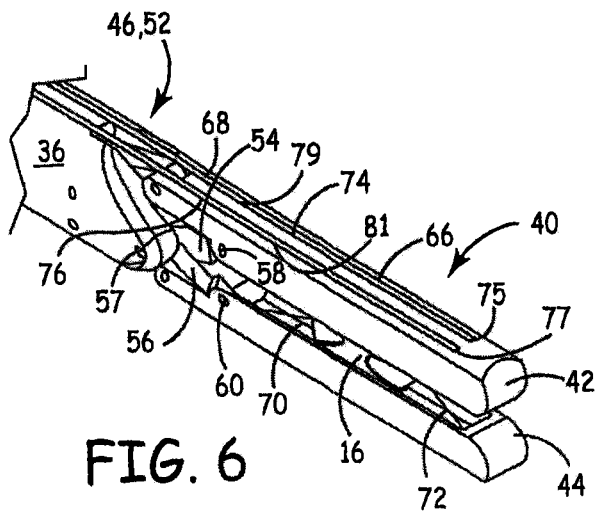
FIG. 6
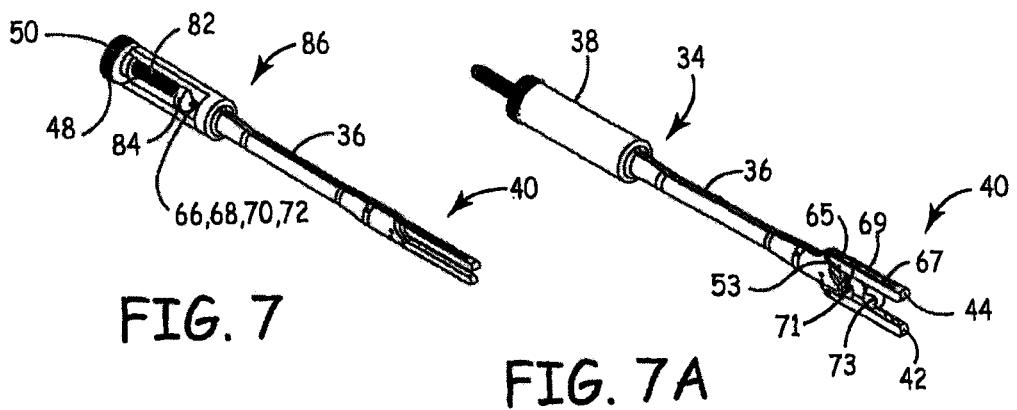
FIG. 7
FIG. 7A

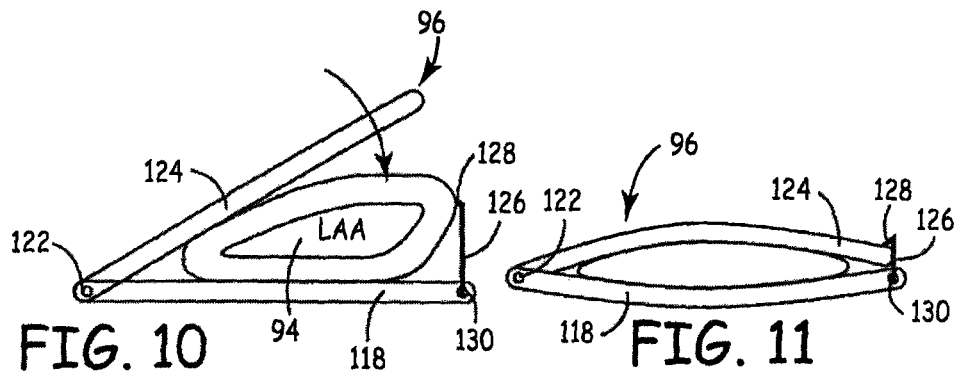
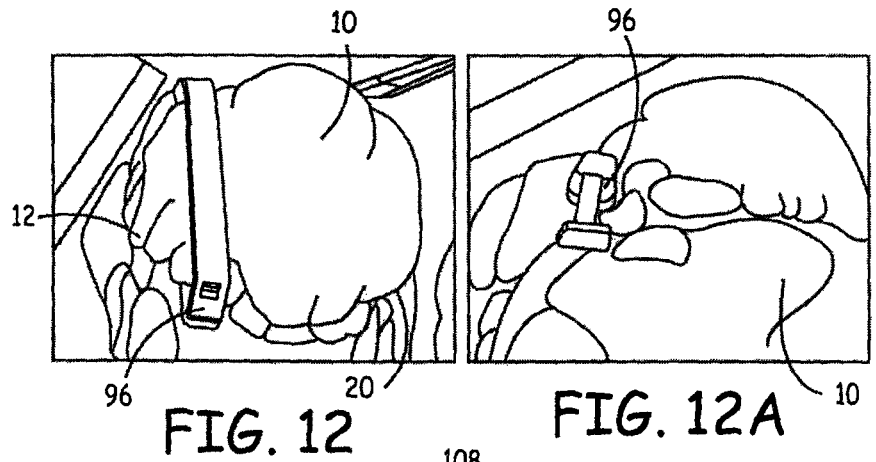
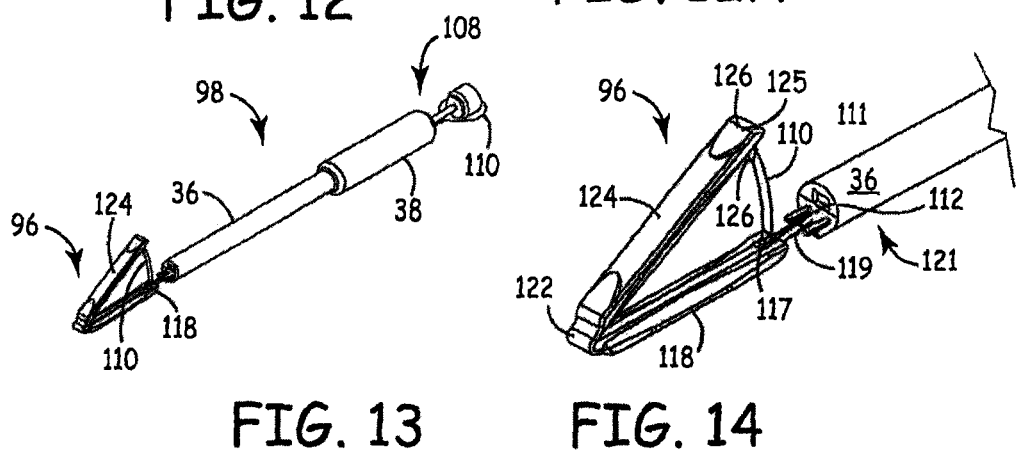

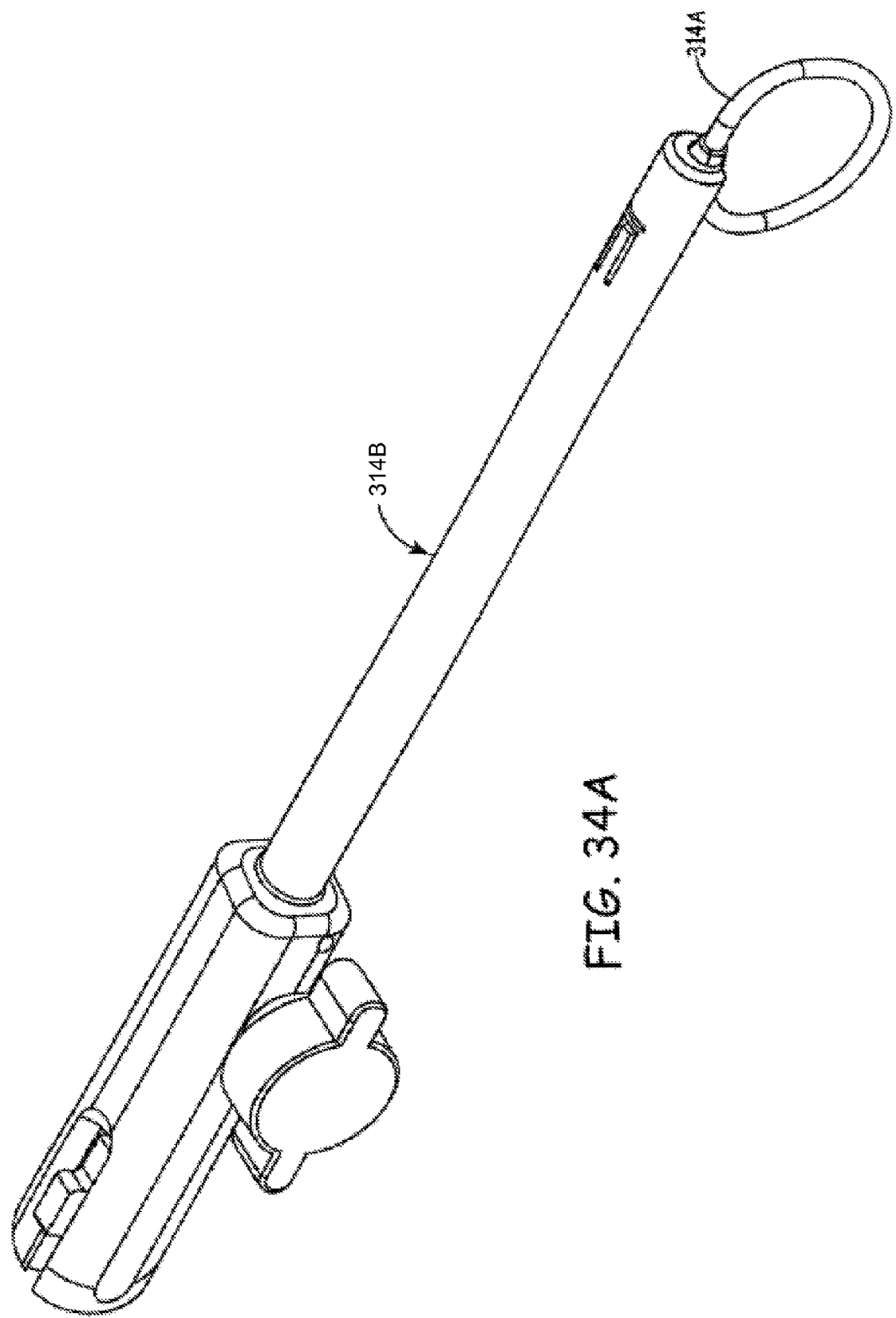

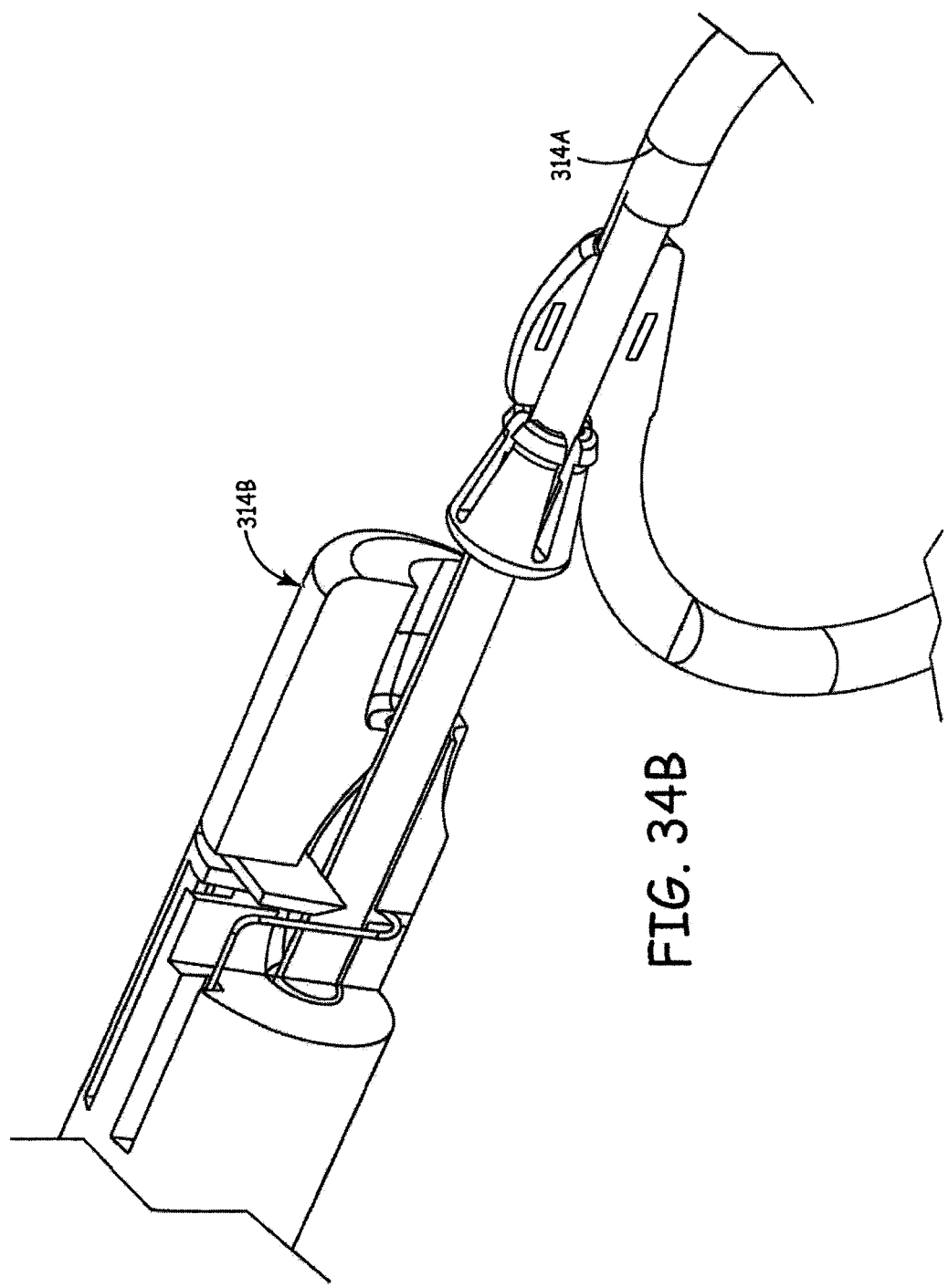

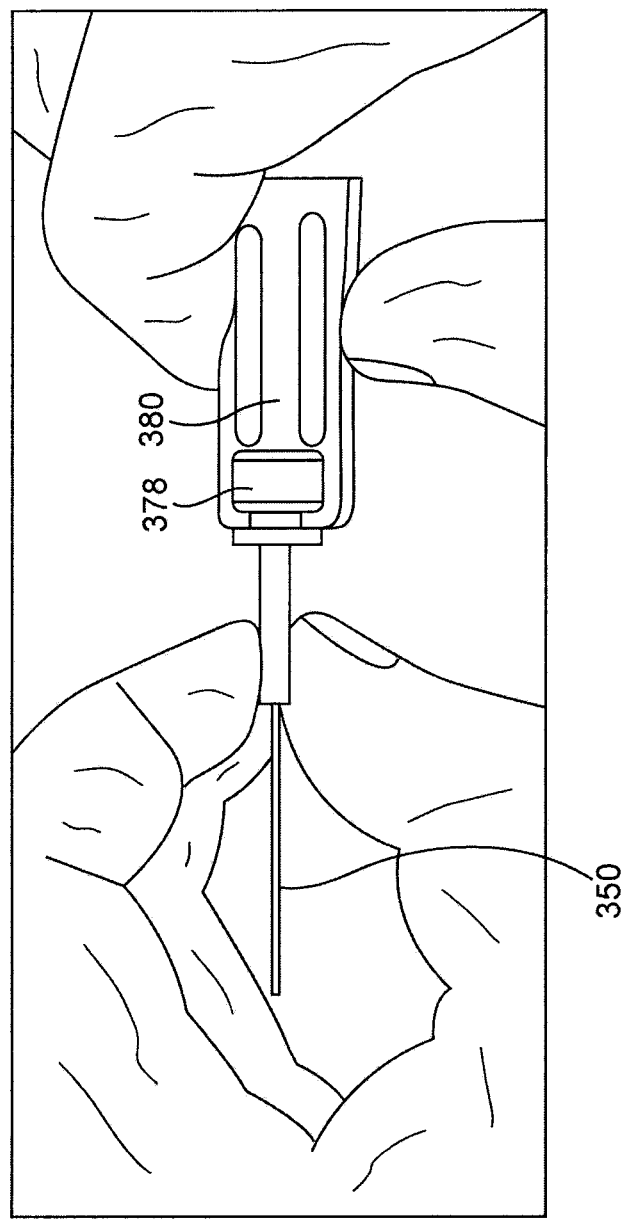

METHOD AND SYSTEM FOR PLACEMENT OF ELECTRICAL LEAD INSIDE HEART

CROSS-REFERENCE TO RELATED APPLICATIONS

This application is a continuation of U.S. application Ser. No. 12/570,390, filed Sep. 30, 2009 which is a continuation-in-part of U.S. application Ser. No. 11/788,261, filed on Apr. 19, 2007, which is a non-provisional of U.S. Provisional Application No. 60/795,752, filed Apr. 28, 2006, and which is a continuation-in-part of U.S. patent application Ser. No. 11/155,699, filed on Jun. 17, 2005, which is now abandoned and which claims the benefit of U.S. Provisional Application No. 60/685,681, filed May 27, 2005, and U.S. Provisional Application No. 60/581,223, filed Jun. 18, 2004. The entire disclosures of each of the above applications are incorporated herein by reference.

FIELD

The present disclosure relates to placement of an electrical lead and, more specifically, to a method and system for placement of an electrical lead inside a heart of a patient.

INTRODUCTION

Embolic stroke is the nation's third leading killer for adults. Embolic stroke is also a major cause of disability. The most common cause of embolic stroke is thrombus formation in the left appendage on the atrium. In almost all atrial fibrillation (AF) patients suffering from embolic stroke, a thrombus clot forms in the appendage of the left atrium.

The primary therapy for the prevention of stroke in AF patients is the administration of oral anticoagulants. Although somewhat effective, there are numerous side effects, including bleeding and lifestyle compromises. Pharmacological therapies (such as Warfarin®) are not well tolerated by patients. The introduction of biomaterials into the left atrial appendage has resulted in the biomaterials eventually breaking down resulting in clot formation. The left atrial appendage has been removed by others via open chest and thoroscopic surgical approaches. Such a procedure is described by Johnson in U.S. Pat. No. 5,306,234 entitled "Method for Closing an Atrial Appendage." The '234 patent discloses a method for grasping the left atrial appendage and manipulating it into position in order to sever the tissue and remove the appendage. The wound on the heart is then sewn or clamped shut.

Appriva Medical, Inc. disclosed concepts for occluding the left atrial appendage from a percutaneous endocardial approach. In U.S. Pat. No. 6,152,144 entitled "Method and Device for Left Atrial Appendage Occlusion" assigned to Appriva Medical, a device and method for isolating the left atrial appendage from the inside of the heart is disclosed. A barrier or other device is anchored in the chamber of the left atrial appendage to prevent the passage of blood into and out of the chamber and thereby prevent clot formation. However, any foreign device left in the chamber of the heart is a potential thrombosis-generating site. In addition, biomaterials are known to eventually break down and result in clotting.

Some surgeons will remove or oversew the left atrial appendage as a concomitant procedure during other cardiac surgery. This is done under general anesthesia and may result in additional trauma to the patient.

While endoscopic or percutaneous approaches reduce the invasiveness of the surgical procedure, the above-described approaches have inherent limitations. Surgical removal of the left atrial appendage is very invasive and often results in loss of atrial hormones, such as atrial natriuretic peptide (ANP), and significant bleeding. In U.S. Pat. No. 6,666,861 issued to Grabek and entitled "Atrial Remodeling Device and Method," a method is disclosed for applying a suture lasso placed endoscopically around the left atrial appendage to isolate it from the atrium. The '861 patent describes using either wet cauterization to remove the tissue or leaving the isolated appendage in place.

Endoscopic stapling devices, suture loops tied to the base of the appendage, and clips pinching the appendage from the outside surface to the base to close the appendage are used by physicians to isolate and remove the left atrial appendage. In U.S. Pat. No. 6,488,689 issued to Kaplan and entitled "Methods and Apparatus for Transpericardial Left Atrial Appendage Closure," a method and apparatus to close the left atrial appendage is disclosed. The '689 patent describes using a grasper and a closing loop or clip applied to the outside of the left atrial appendage. The clip is applied extending toward the chamber of the atrial appendage and extending over the outside edge of the appendage. The clips of the '689 patent are a U-shaped metal clip, having a spring tendency to hold its shape, being deformed to open while positioned to extend over the tissue, before the clip is allowed to return to its resting shape, having the tissue pinched between the ends of the clip.

Moreover, electrical leads (e.g., pacemaker leads, defibrillator leads, cardiac resynchronization leads, etc.) are often mechanically and electrically connected to cardiac tissue in order to maintain a predetermined heartbeat. For instance, an electrical lead can be routed through the superior vena cava to be connected to endocardial tissue on the right side of the heart. However, access to the left side of the heart can be limited. Thus, an electrical lead can be routed through branch blood vessels and connected to cardiac tissue on the outer portion of the left side of the heart.

Care is taken so that the electrical lead does not inadvertently interfere with function of nerves adjacent the heart. For instance, the physician connects the lead on the outer portion of the left side of the heart, avoiding electrical contact with the phrenic nerve. Since access on the outer cardiac tissue is limited, this can be a difficult and time consuming process.

What follows will include a description of a system and a method for connecting an electrical lead inside a heart. The system and the related method facilitate connection of the electrical lead and ensure that the lead will not inadvertently interfere with surrounding structures, such as the phrenic nerve.

SUMMARY

This section provides a general summary of the disclosure, and is not a comprehensive disclosure of its full scope or all of its features.

A method of placing an electrical lead of an implantable cardiac device inside a heart of a patient is disclosed. The method includes securing a tool to an atrial appendage of the heart to hold onto the atrial appendage, piercing the atrial appendage, and creating an aperture in the atrial appendage while holding the atrial appendage with the tool. The method also includes moving a distal end of the electrical lead into the heart through the aperture in the atrial appendage and into a ventricle of the heart. Furthermore, the method includes coupling the distal end of the electrical lead to cardiac tissue in the ventricle and delivering an electrical signal to the cardiac tissue in the ventricle of the heart to maintain a predetermined heartbeat of the heart.

A system for delivering an electrical lead to a ventricle of a heart of a patient is also disclosed. The system includes a securing member for securing and holding onto an atrial appendage of the heart and a piercing member for piercing and forming an aperture in the atrial appendage while the securing member holds onto the atrial appendage. The system further includes an electrical lead having a distal end. The distal end is insertable through the aperture in the atrial appendage and into the left ventricle of the heart. Also, the electrical lead is connectable to an implantable cardiac device. The electrical lead delivers an electrical signal to the cardiac tissue to maintain a predetermined heartbeat. Moreover, the system includes an abutment member that is implantable in the heart, and the abutment member surrounds the electrical lead and is positionable between the heart and the electrical lead to inhibit direct contact between the heart and the electrical lead.

Furthermore, a method of placing a distal end of an electrical lead inside a heart of a patient is disclosed. The method includes securing a tool to a left atrial appendage of the heart to hold onto the left atrial appendage and piercing the atrial appendage with a piercing tool that is operably coupled to the tool to create an aperture in the left atrial appendage while holding onto the left atrial appendage. The method also includes moving the distal end of the electrical lead through a passage in the tool, through the aperture in the left atrial appendage, and into the left ventricle of the heart, while holding onto the left atrial appendage. Additionally, the method includes implanting a sleeve in the heart, and the sleeve receives the electrical lead and prevents direct contact between the heart and the electrical lead. Moreover, the method includes compressing the sleeve to hold the electrical lead in place relative to the sleeve. Moreover, the method includes connecting the distal end of the electrical lead to cardiac tissue inside the left ventricle of the heart, connecting the electrical lead to an implantable cardiac device, and delivering an electrical signal to the cardiac tissue via the electrical lead to maintain a predetermined heartbeat of the heart. Still further, the method includes manipulating the tool to resiliently stretch a resilient ring over an outer surface of the left atrial appendage and manipulating the tool to release the resilient ring to resiliently recover and occlude the left atrial appendage.

Further areas of applicability will become apparent from the description provided herein. The description and specific examples in this summary are intended for purposes of illustration only and are not intended to limit the scope of the present disclosure.

DRAWINGS

FIG. 6 is a perspective view of an applicator head of the ring occluder applicator of FIG. 5.

FIG. 7 is a perspective view of the handle mechanism of the ring occluder applicator of FIG. 5.

FIG. 7A is a perspective view of the ring occluder applicator in FIG. 5 with a ring occluder attached.

FIG. 10 is a cross-sectional schematic illustration of a left atrial appendage occlusion device according to one embodiment of the invention, before being clamped around the left atrial appendage.

FIG. 11 is a cross-sectional schematic illustration of the occlusion device of FIG. 10, after being clamped around the left atrial appendage.

FIG. 12 is a perspective view of the occlusion device of FIG. 10 applied to a patent's heart.

FIG. 12A is an end view of the occlusion device of FIG. 10 applied to a patient's heart.

FIG. 13 is a perspective view of a clip applicator according to one embodiment of the invention.

FIG. 14 is a perspective view of an applicator head of the clip applicator of FIG. 13.

FIG. 34A is a perspective view of an adjustable band occluder and a device for implanting the adjustable band occluder.

FIG. 34B is an enlarged view of portions of the adjustable band occluder and the device of FIG. 34A with portions broken away to illustrate additional details.

FIGS. 36A-E are perspective views of an endoloop left atrial appendage ligation procedure.

FIGS. 37A-E are side and perspective views of an atrial septal defect repair device.

Figure 38:
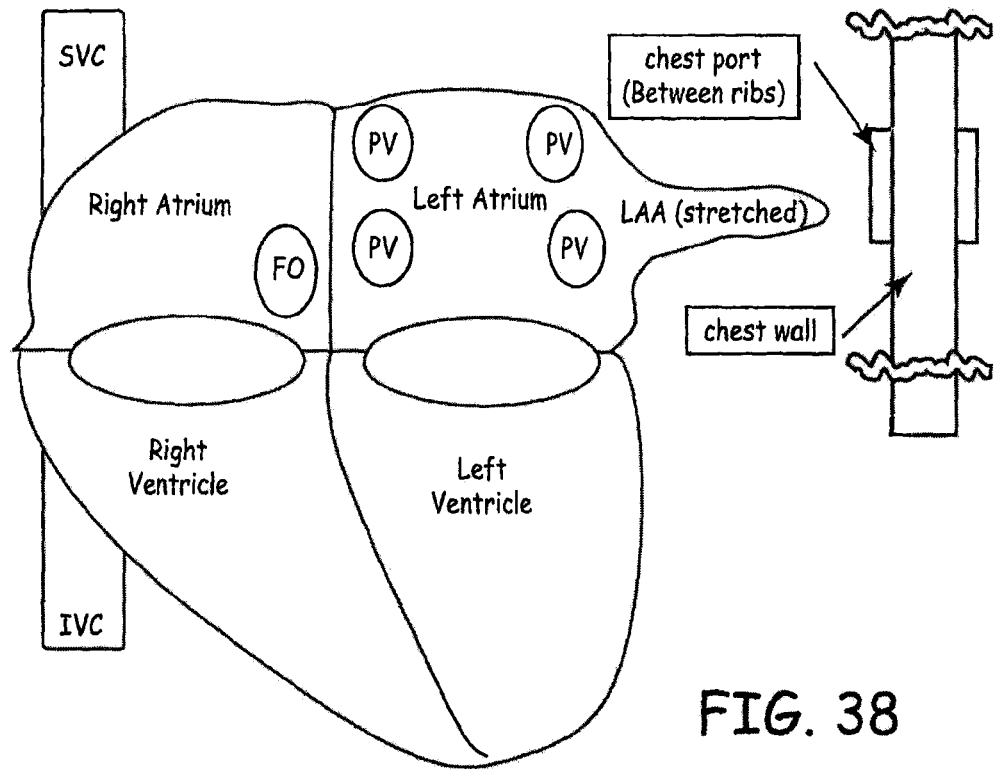

FIG. 38 is a schematic cross-sectional representation of a heart and a chest wall.

Figure 39:
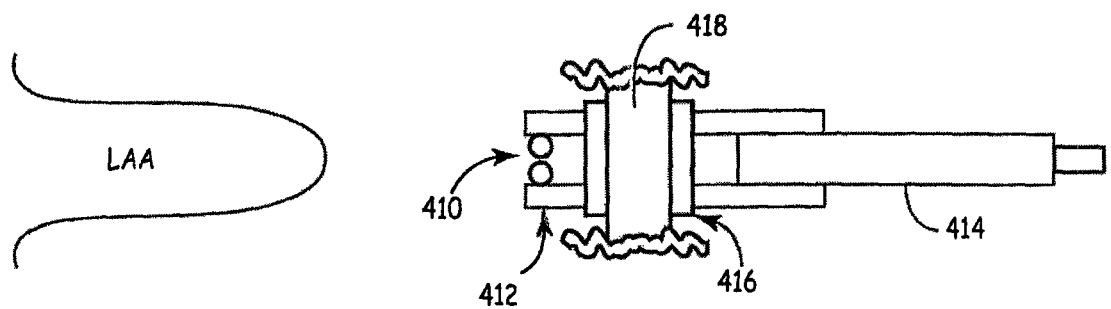

FIG. 39 is a side view of a device according to one embodiment of the invention passed through a port placed between the ribs.

Figure 40:
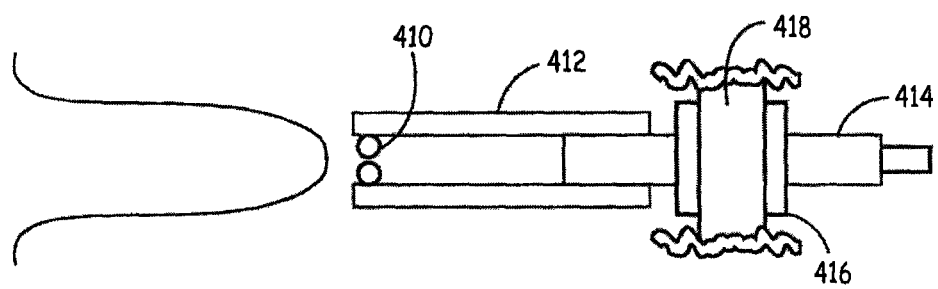

FIG. 40 is a side view of the device of FIG. 39 advanced toward the left atrial appendage.

Figure 41:
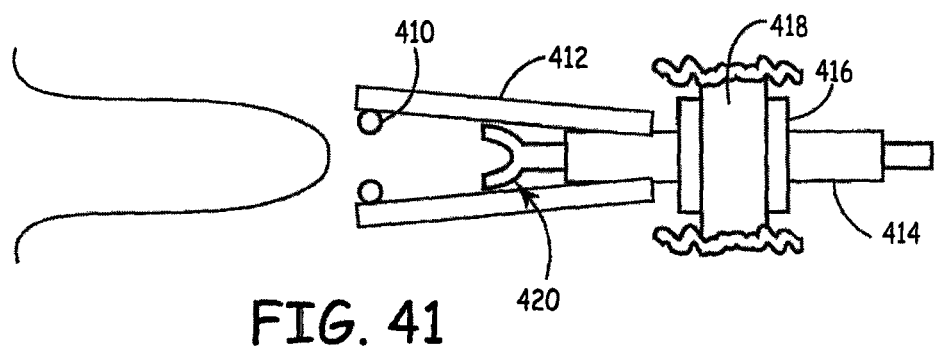

FIG. 41 is a side view of the device of FIG. 39 including a suction cup or grasper probe being advanced through portal tube.

Figure 42:
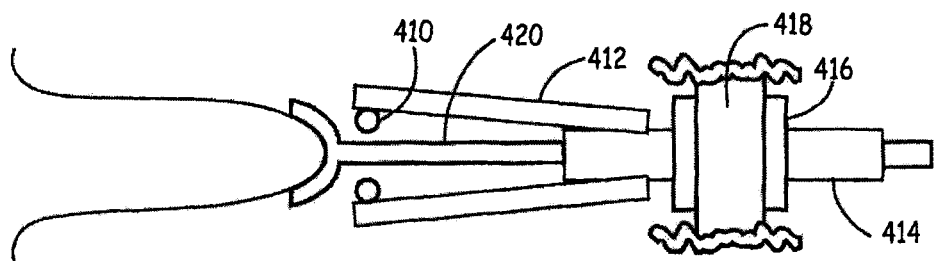

FIG. 42 is a side view of the device of FIG. 41 with the suction cup or grasper probe attached to an end of the left atrial appendage.

Figure 43:
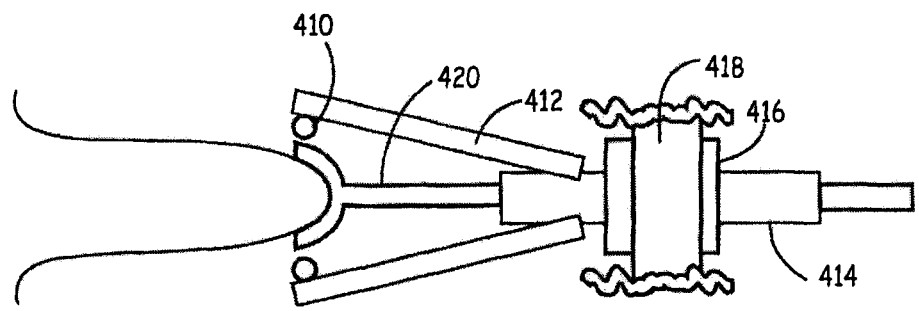

FIG. 43 is a side view the device of FIG. 41 with cinch-ring support arms expanded and the left atrial appendage pulled toward a portal tube.

Figure 44:
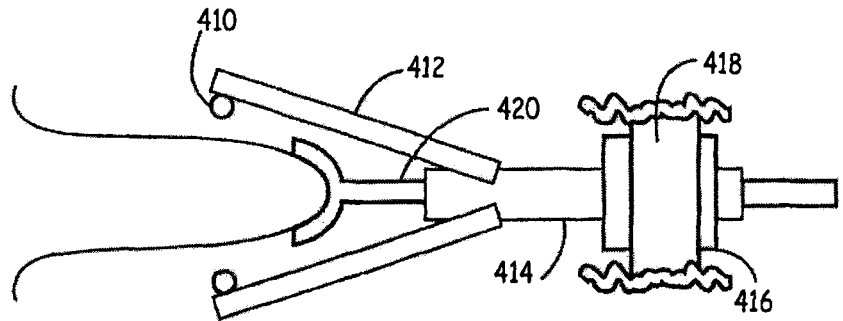

FIG. 44 is a side view of the device of FIG. 41 with the cinch-ring support arms advanced over the left atrial appendage.

Figure 45:
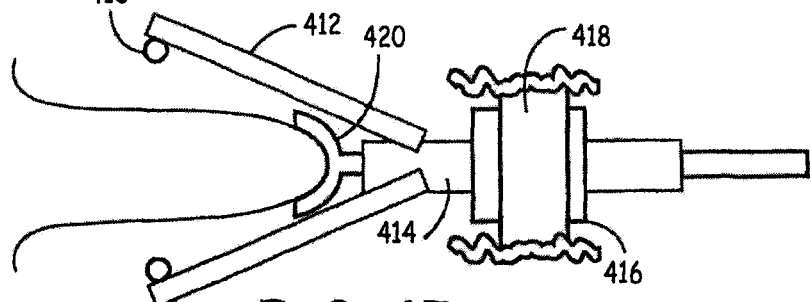

FIG. 45 is a side view of the device of FIG. 41 with the cinch-ring support arms positioned over a mid to proximal left atrial appendage.

Figure 46:
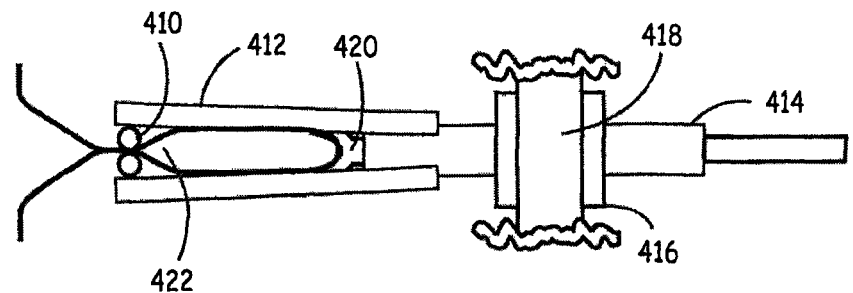

FIG. 46 is a side view of the device of FIG. 41 with the cinch-ring support arms allowed to contract over the left atrial appendage and occlude a lumen of the left atrial appendage.

Figure 47:
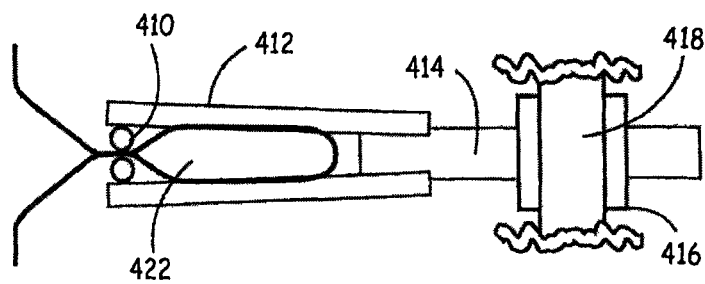

FIG. 47 is a side view of the device of FIG. 41 with the suction cup or grasper probe removed from the portal tube.

Figure 48:
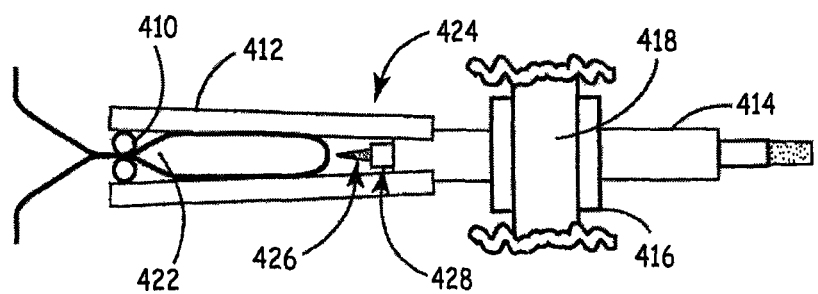

FIG. 48 is a side view of a dilator/sheath assembly advanced through the portal tube.

Figure 49:
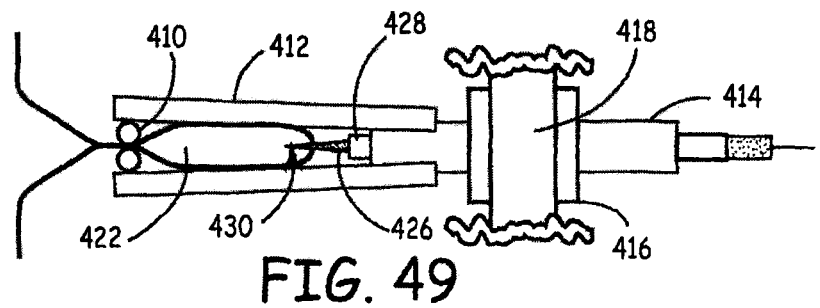

FIG. 49 is a side view of the dilator/sheath assembly of FIG. 48 with a needle or sharp wire advanced through a lumen of the dilator to puncture into the left atrial appendage lumen.

Figure 50:
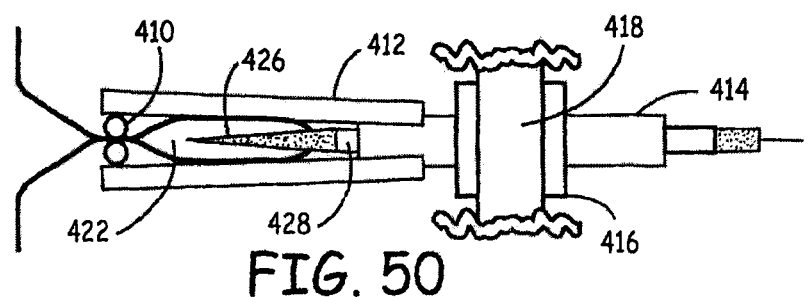

FIG. 50 is a side view of the dilator of FIG. 49 advanced into the lumen of left atrial appendage and the needle retracted.

Figure 51:
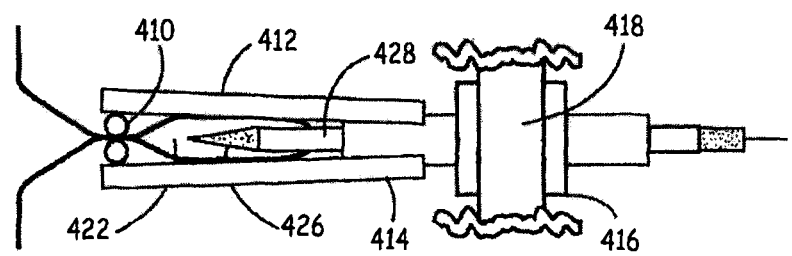

FIG. 51 is a side view of the dilator of FIG. 49 with the sheath advanced over the dilator into left atrial appendage lumen.

Figure 52:
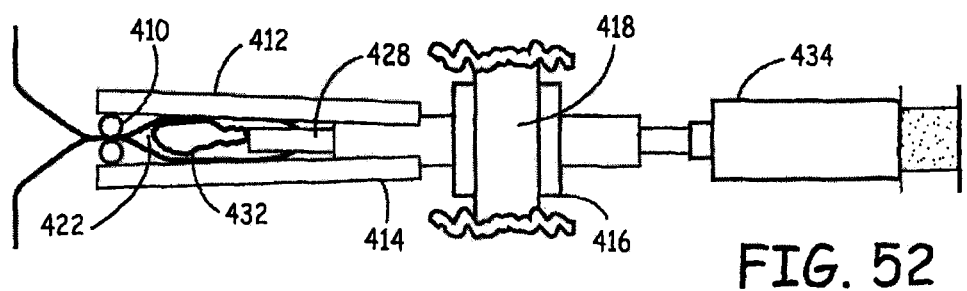

FIG. 52 is a side view of the dilator of FIG. 51 with the left atrial appendage lumen being aspirated of blood and flushed with heparinized saline to prevent thrombus formation.

Figure 53:
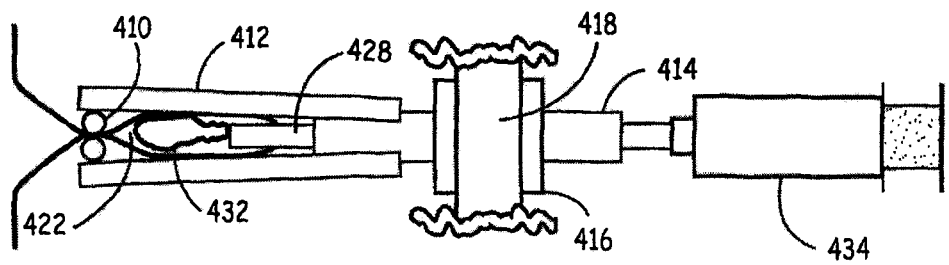

FIG. 53 is a side view of the dilator of FIG. 51 with the left atrial appendage being filled with heparinized saline as blood and air are removed.

Figure 54:
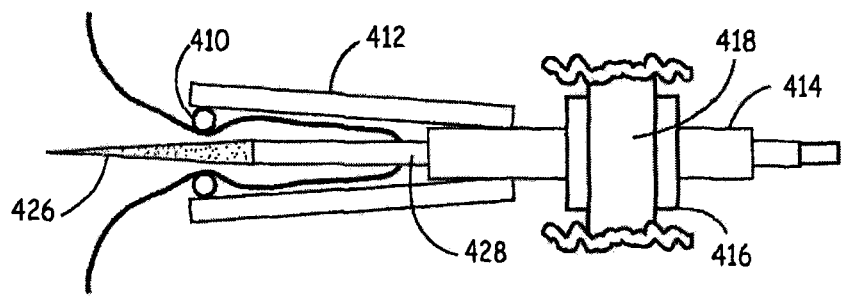

FIG. 54 is a side view of the dilator of FIG. 51 being advanced past the cinch ring and into the left atrium.

Figure 55:
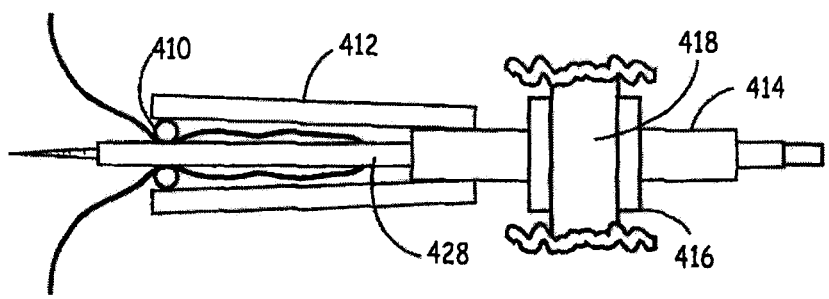

FIG. 55 is a side view of the sheath of FIG. 51 being advanced over the dilator past the cinch ring and into the left atrium.

Figure 56:
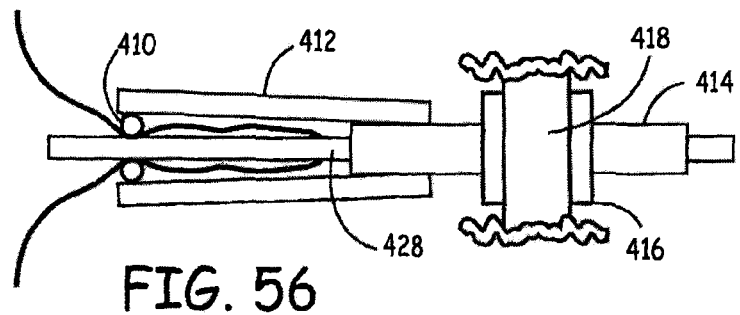

FIG. 56 is a side view of the sheath of FIG. 51 with the dilator removed.

Figure 57:
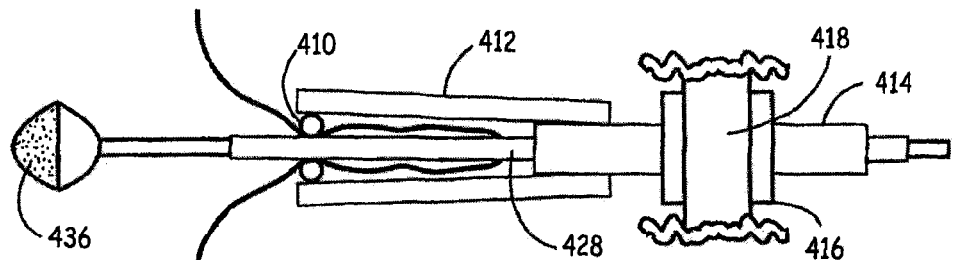

FIG. 57 is a side view the sheath of FIG. 56 with therapeutic implements being advanced into the left atrium.

Figure 58:
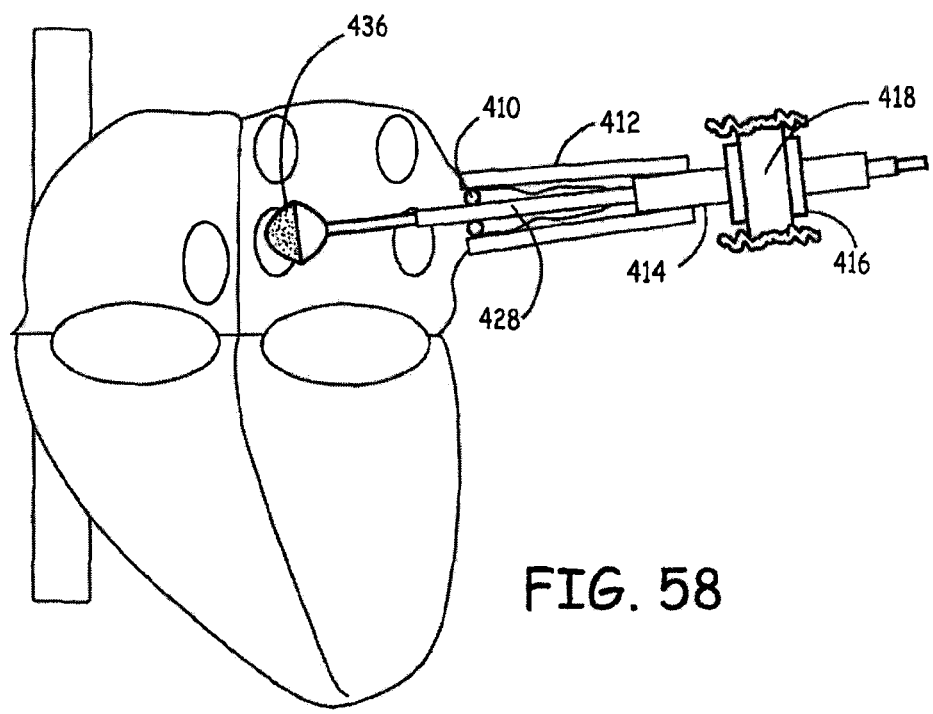

FIG. 58 is a side view of a balloon ablation device according to one embodiment of the invention at the right inferior pulmonary vein ostium.

Figure 59:
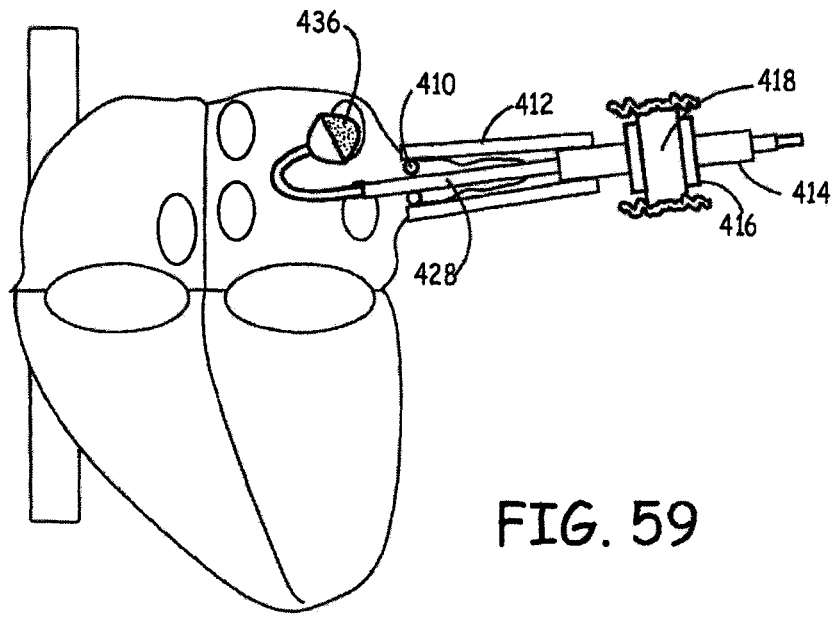

FIG. 59 is a side view of the balloon ablation device of FIG. 58 at the left superior pulmonary vein ostium.

Figure 60:
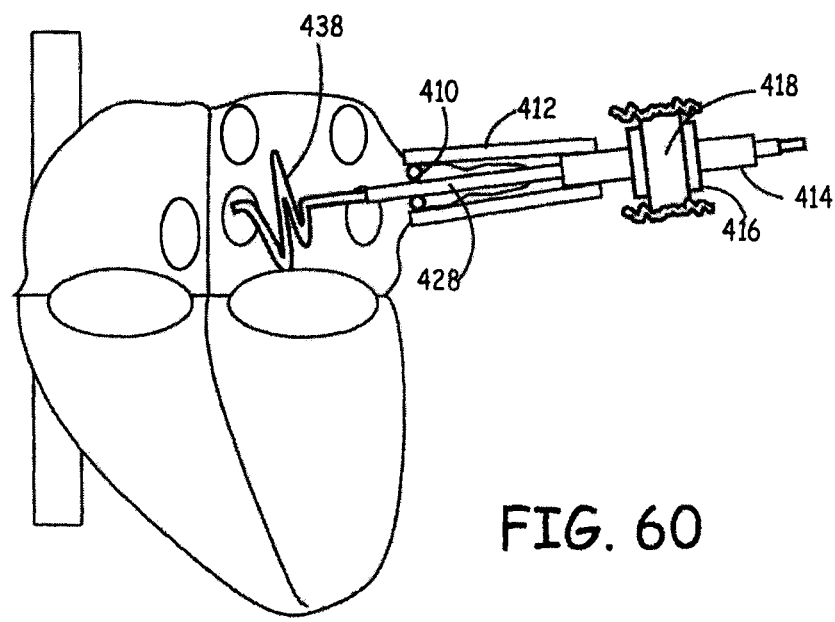

FIG. 60 is a side view of an encircling ablation device according to one embodiment of the invention approaching the left superior pulmonary vein ostium.

Figure 61:
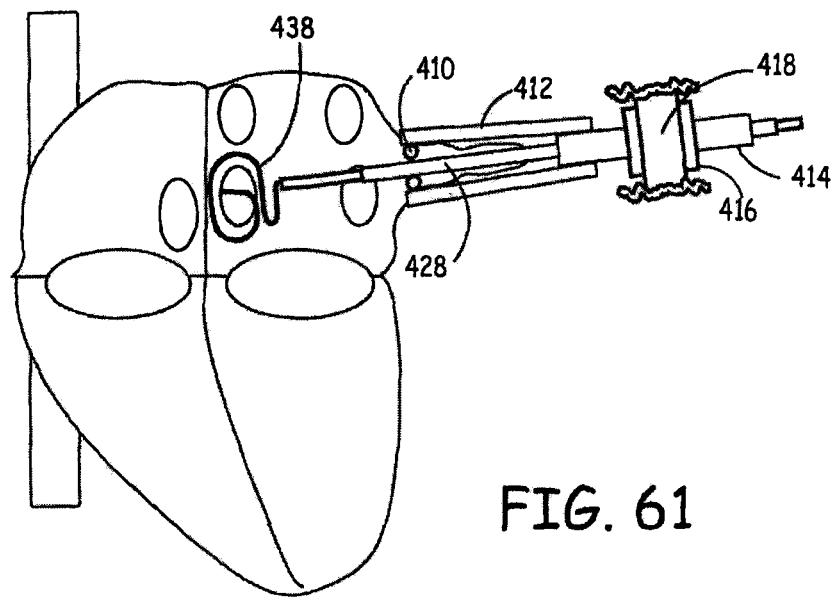

FIG. 61 is a side view of the encircling ablation device of FIG. 60 placed around the left superior pulmonary vein ostium.

Figure 62:
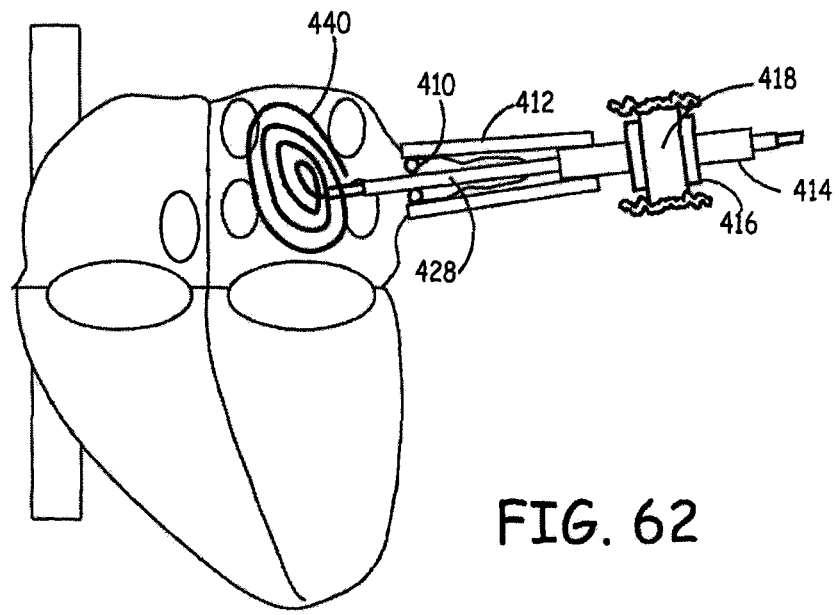

FIG. 62 is a side view of a left atrial de-bulking spiral ablation device according to one embodiment of the invention placed against the posterior left atrium.

Figure 63:
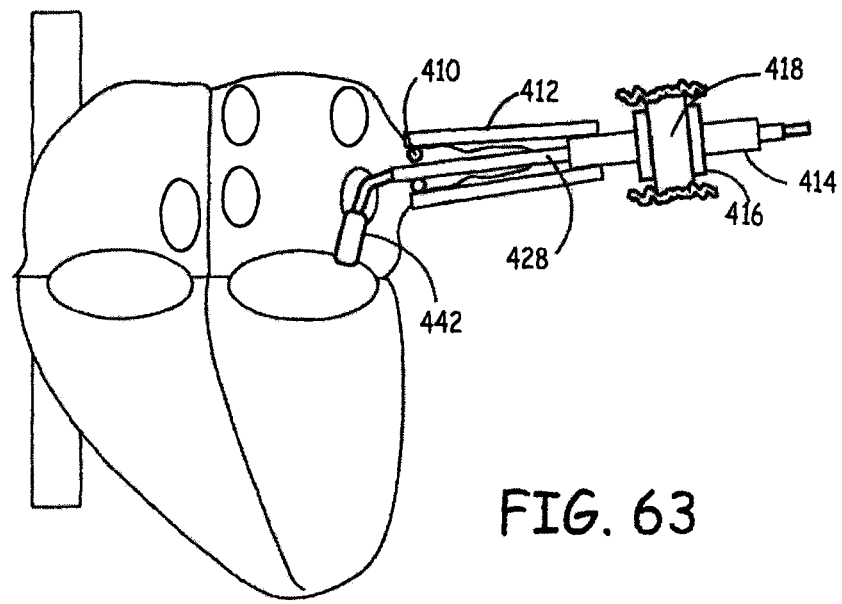

FIG. 63 is a side view of a high intensity focused ultrasound ablation device according to one embodiment of the invention creating a lesion over the left atrial isthmus.

Figure 64:
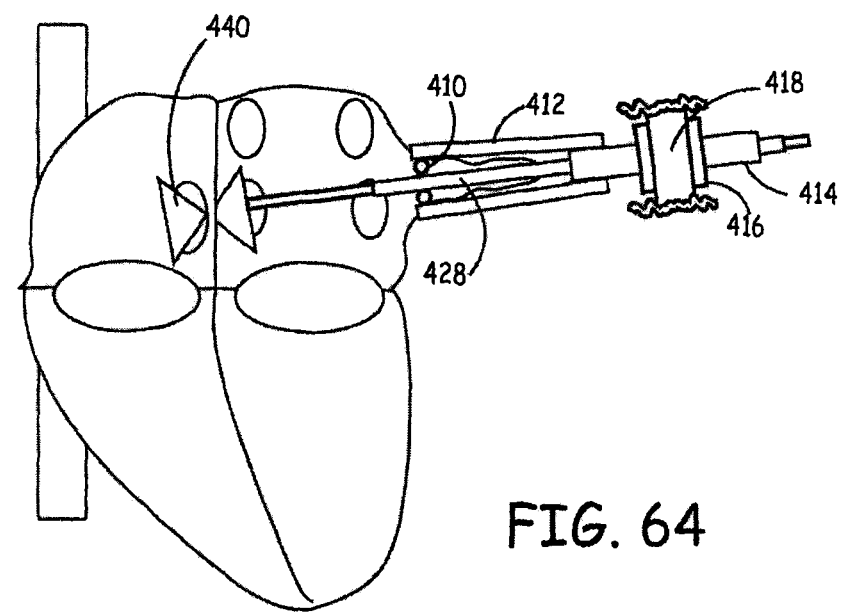

FIG. 64 is a side view of a PFO or ASD closure device according to one embodiment of the invention being deployed in the fossa ovalis of the inter-atrial septum.

Figure 65:
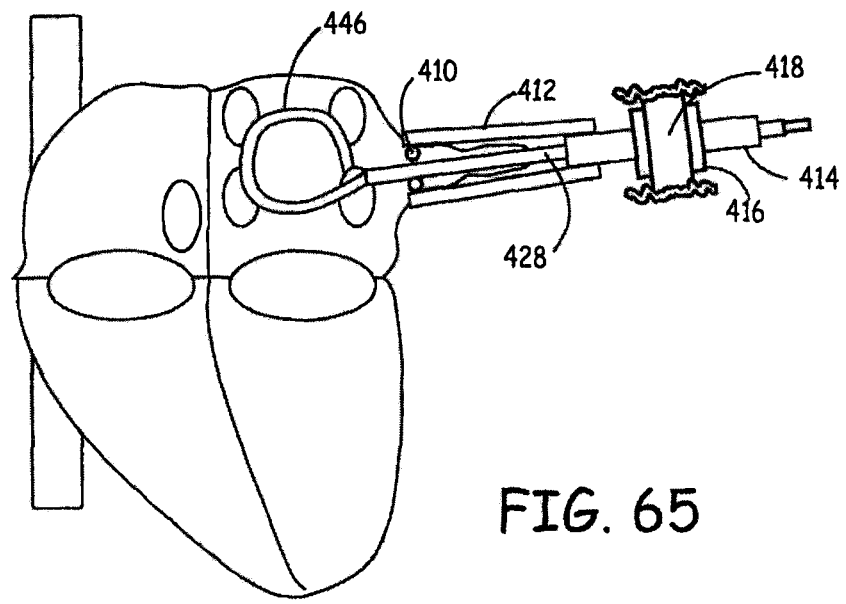

FIG. 65 is a side view of a linear ablation device according to one embodiment of the invention forming connecting lesions between pulmonary veins.

Figure 66:
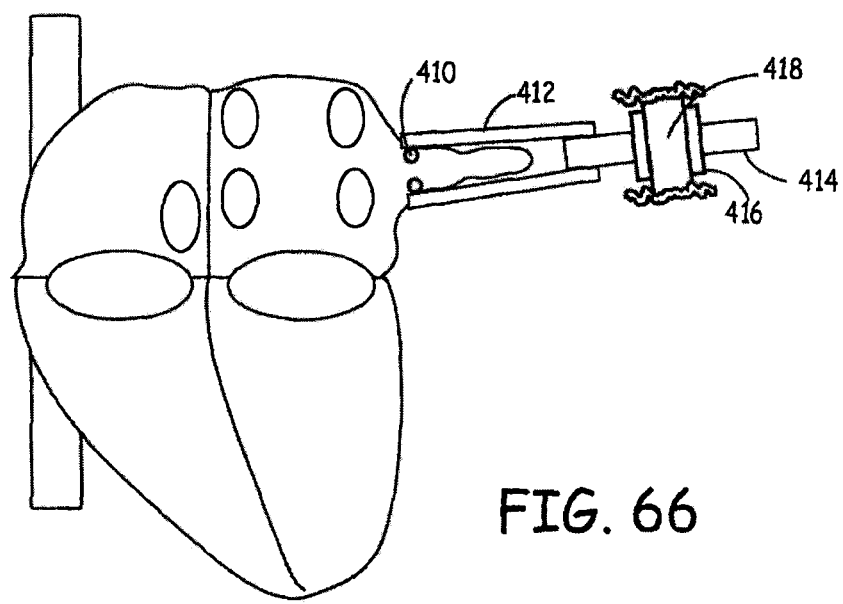

FIG. 66 is a side view of an elastic cinch ring according to one embodiment of the invention allowed to constrict down around the base of the left atrial appendage.

Figure 67:
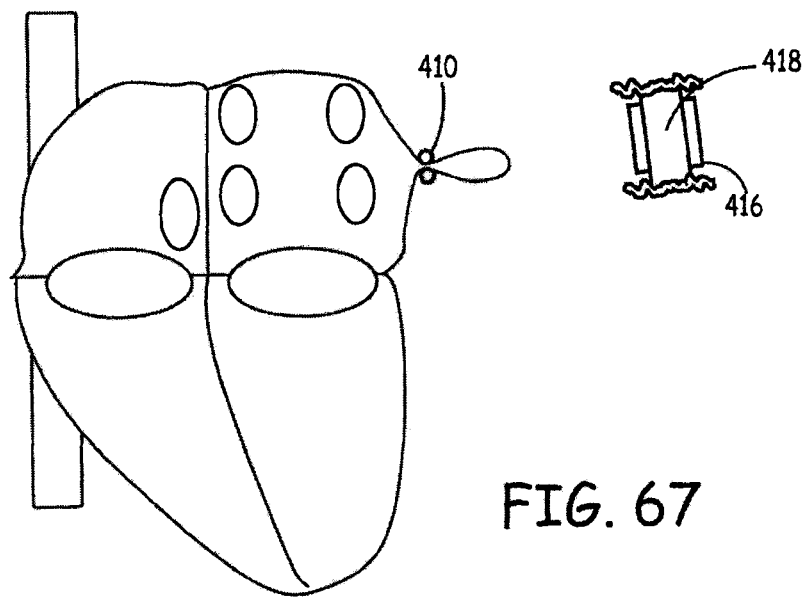

FIG. 67 is a side view of the elastic cinch ring of FIG. 66 immediately following the procedure.

Figure 68:
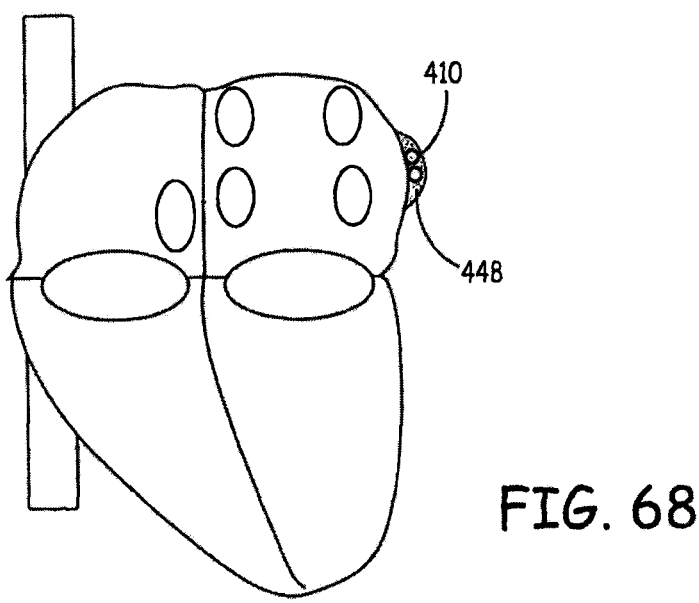

FIG. 68 is a side view of the elastic cinch ring of FIG. 66 after approximately 12 weeks.

Figure 69:
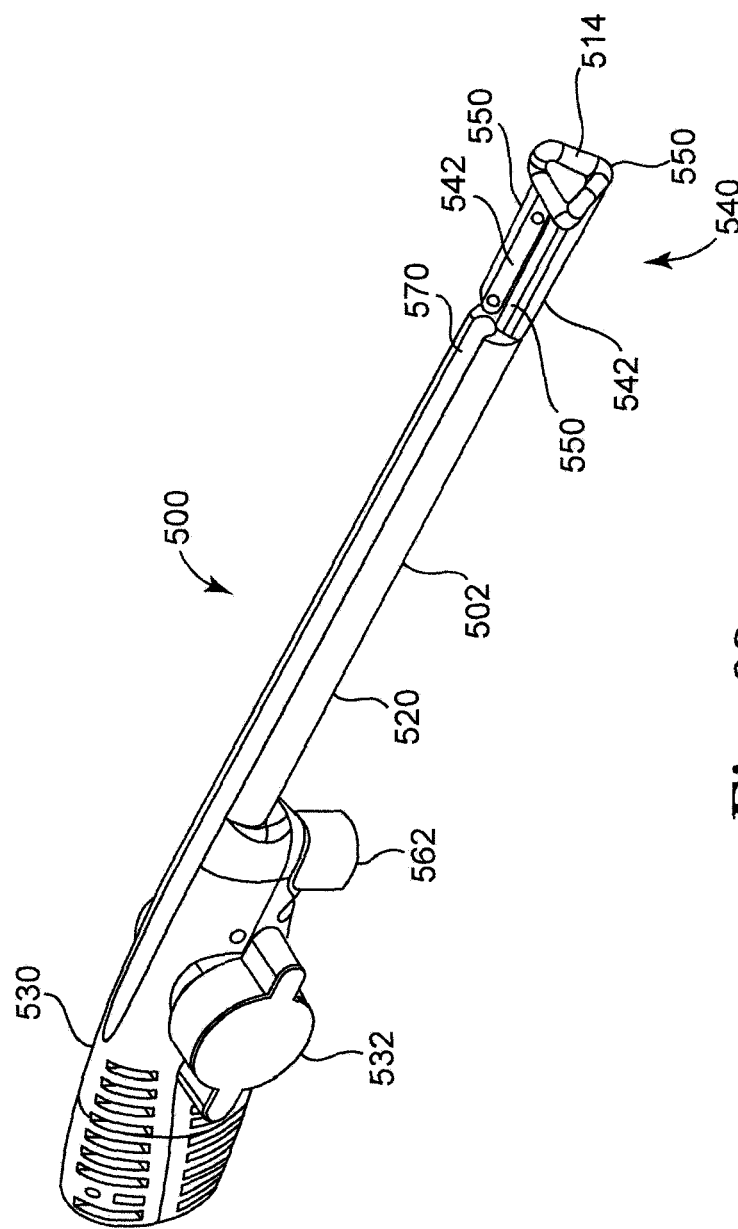

FIG. 69 is a perspective view of one embodiment of a device according to one embodiment of the invention.

Figure 70:
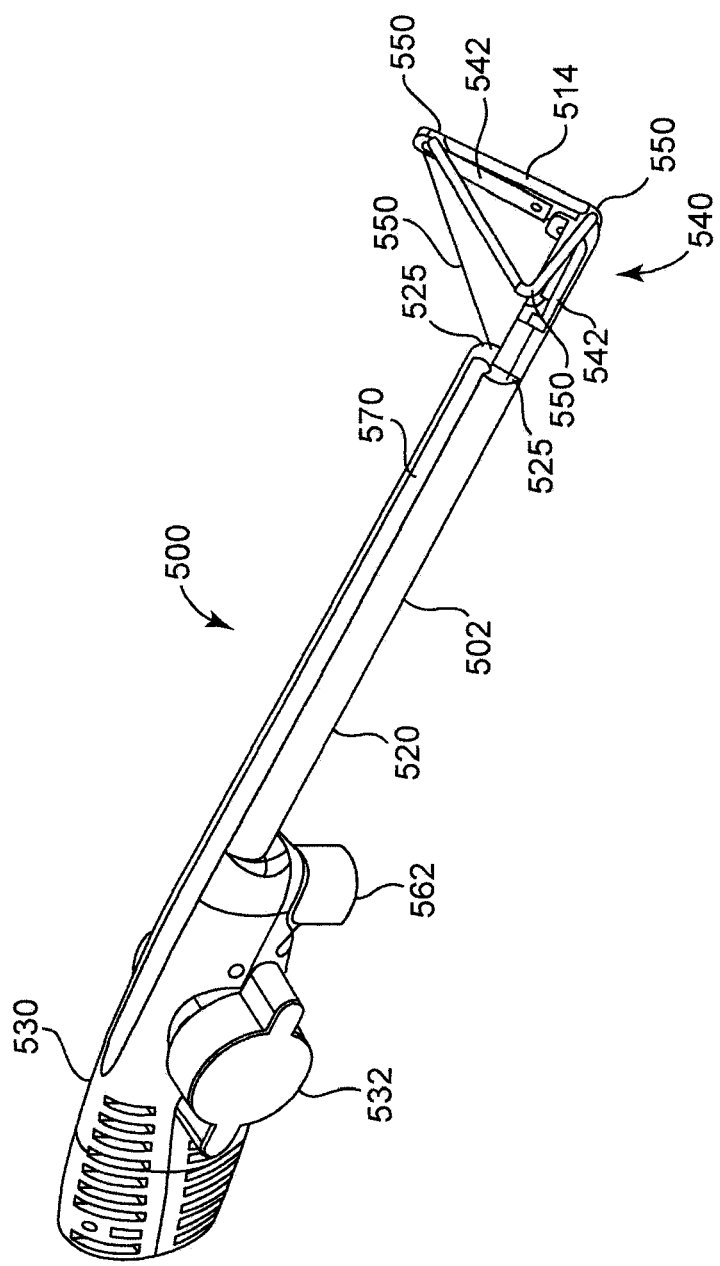

FIG. 70 is a perspective view of one embodiment of a device according to one embodiment of the invention.

Figure 71:
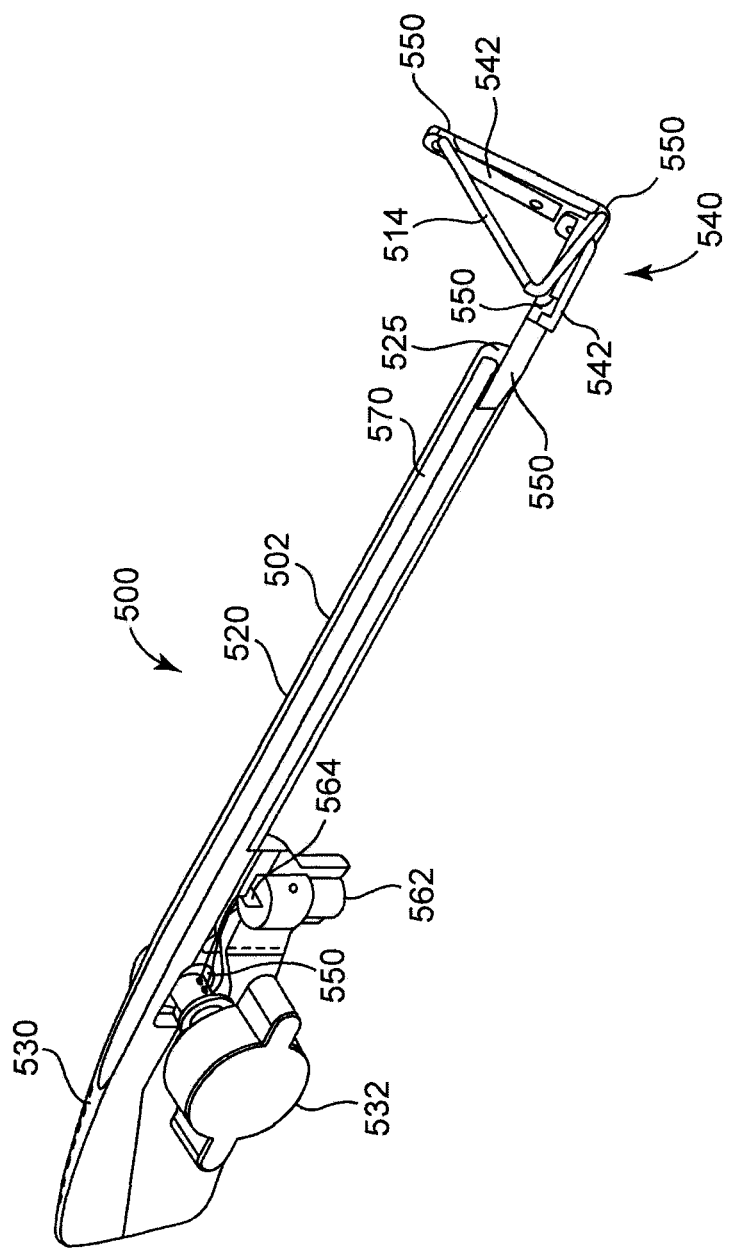

FIG. 71 is a partial cross-sectional view of one embodiment of a device according to one embodiment of the invention.

Figure 72:
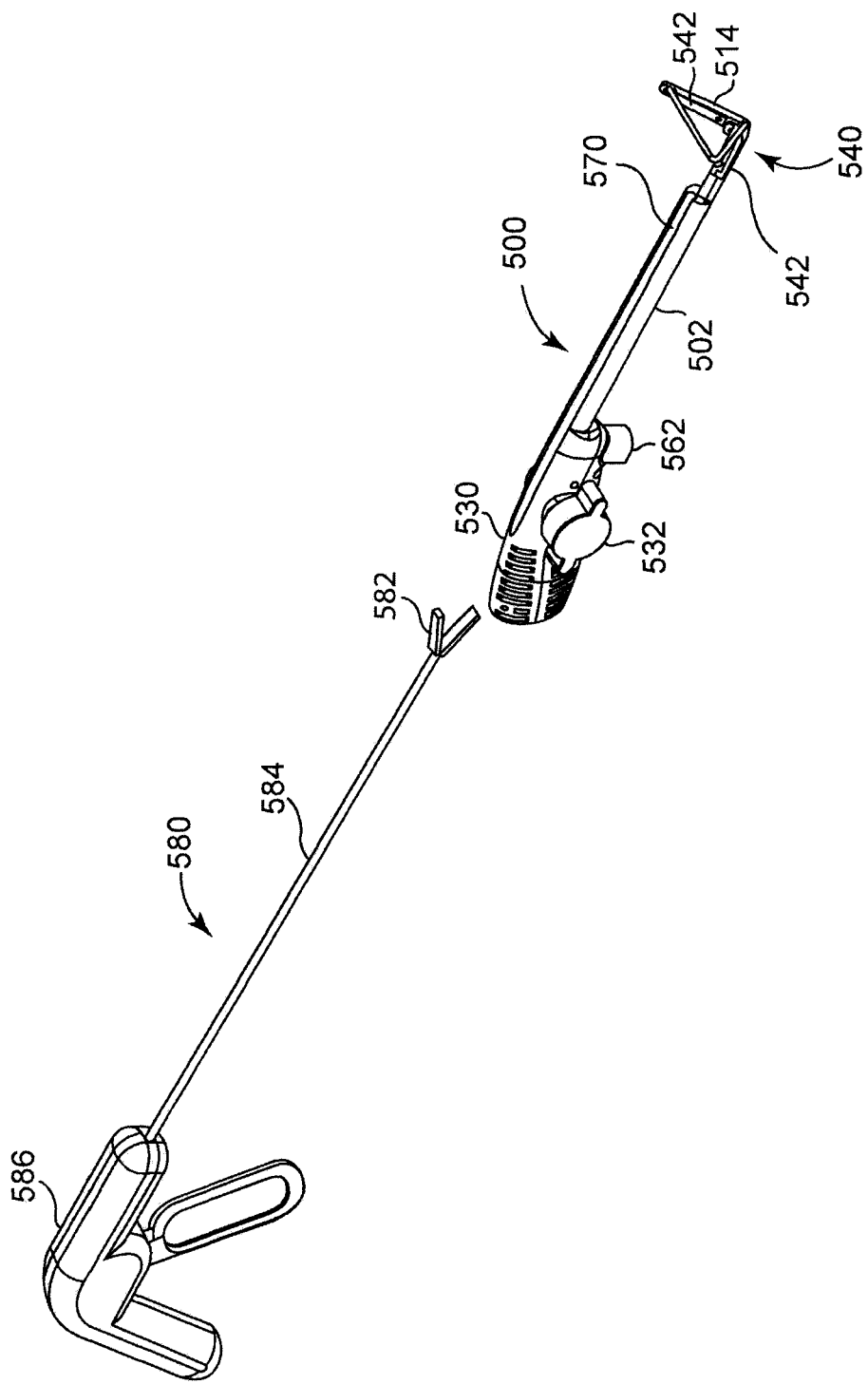

FIG. 72 is a perspective view of one embodiment of a pair of devices according to one embodiment of the invention.

Figure 73:
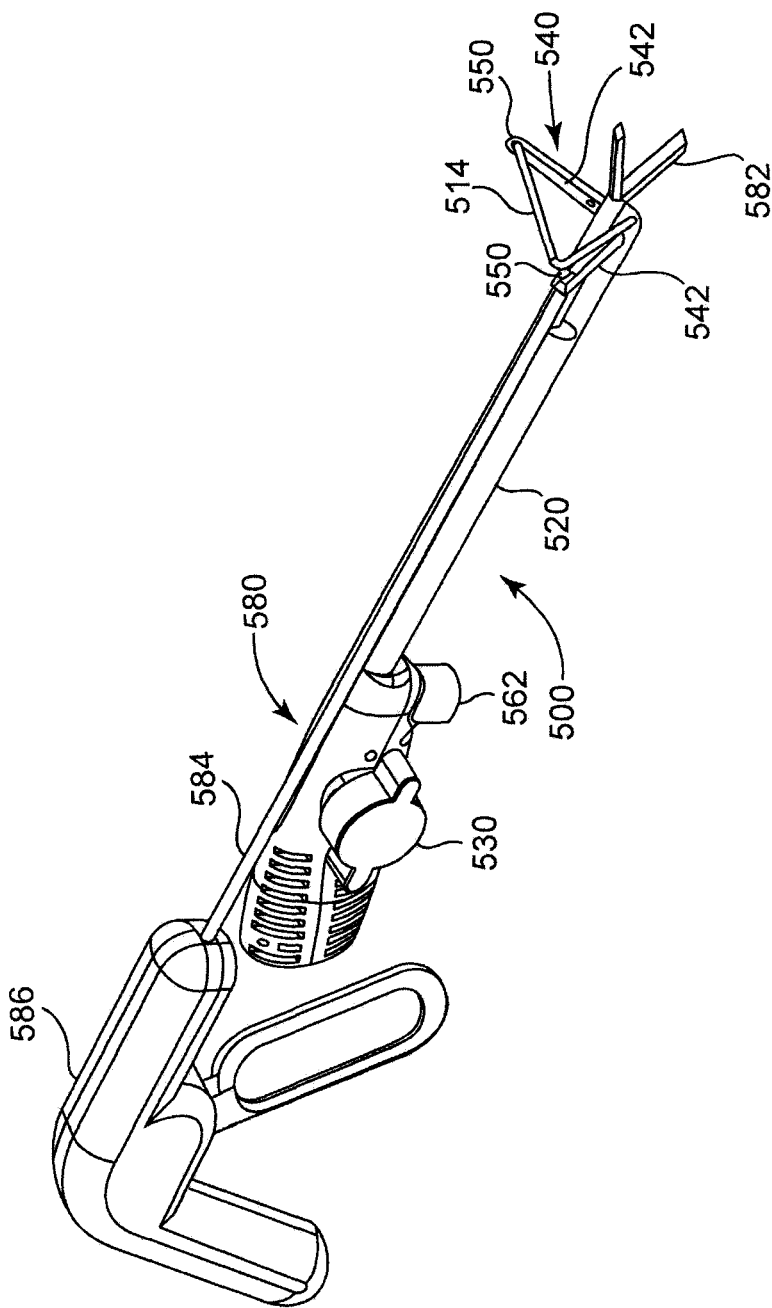

FIG. 73 is a perspective view of one embodiment of a pair of devices according to one embodiment of the invention.

Figure 74:
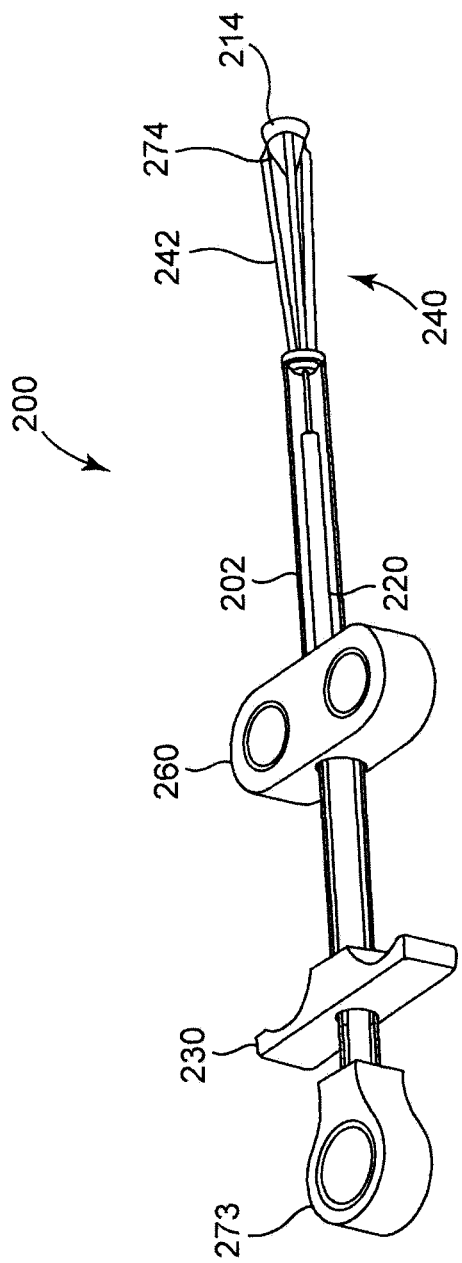

FIG. 74 is a perspective view of one embodiment of a device according to one embodiment of the invention.

Figure 75:
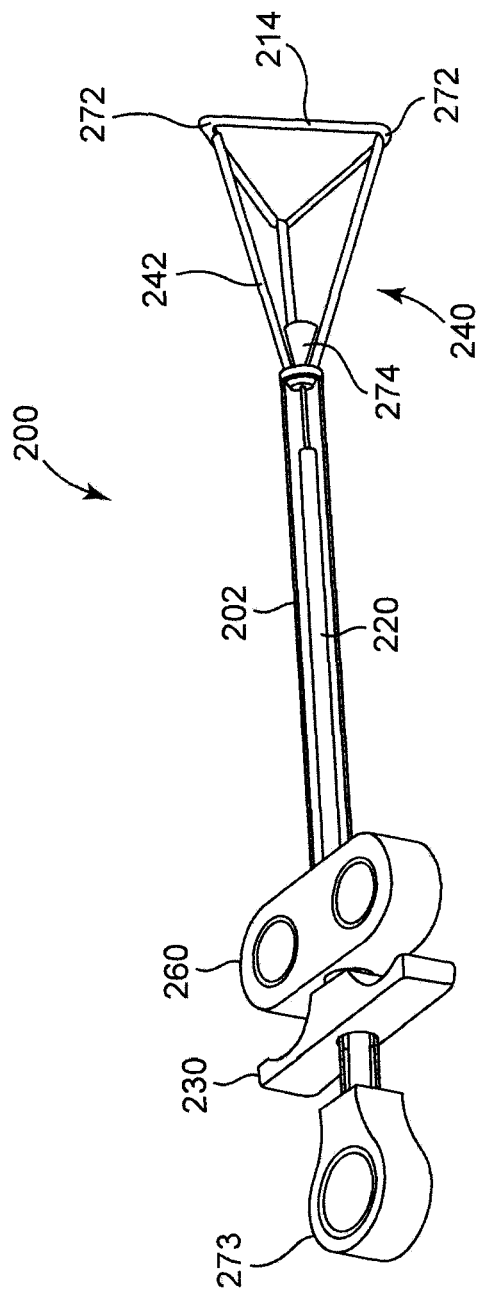

FIG. 75 is a perspective view of one embodiment of a device according to one embodiment of the invention.

Figure 76:
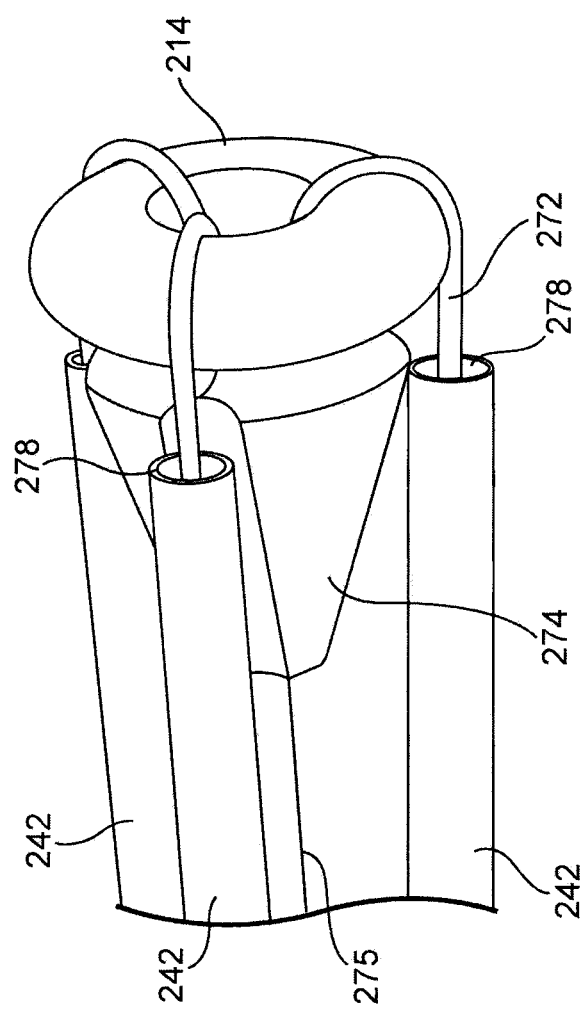

FIG. 76 is a perspective view of a distal portion of one embodiment of a device according to one embodiment of the invention.

Figure 77:
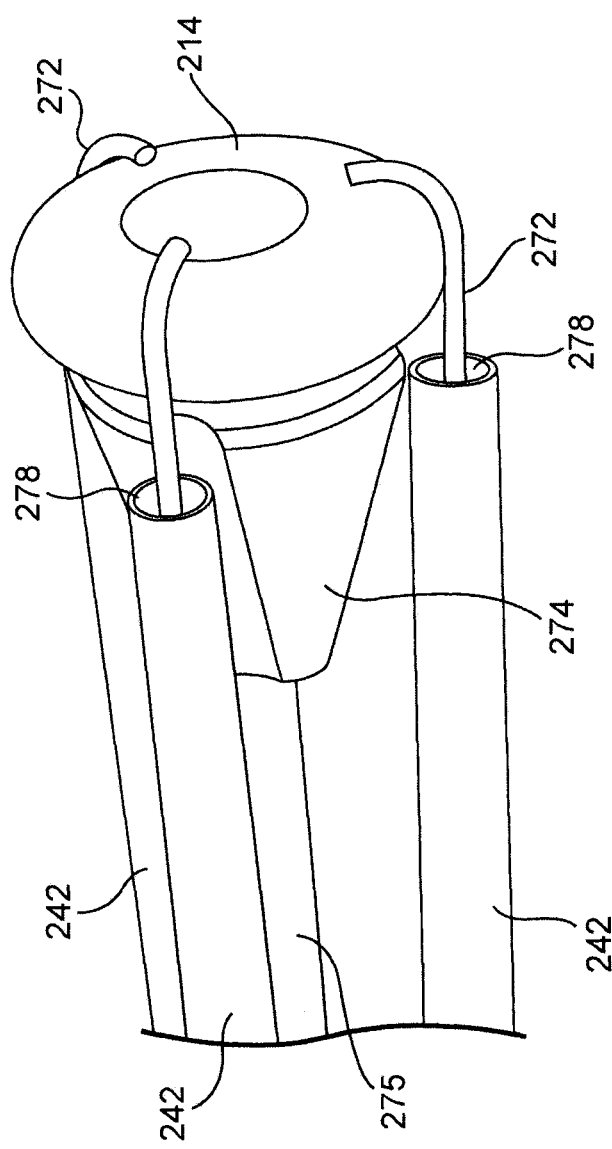

FIG. 77 is a perspective view of a distal portion of one embodiment of a device according to one embodiment of the invention.

Figure 78:
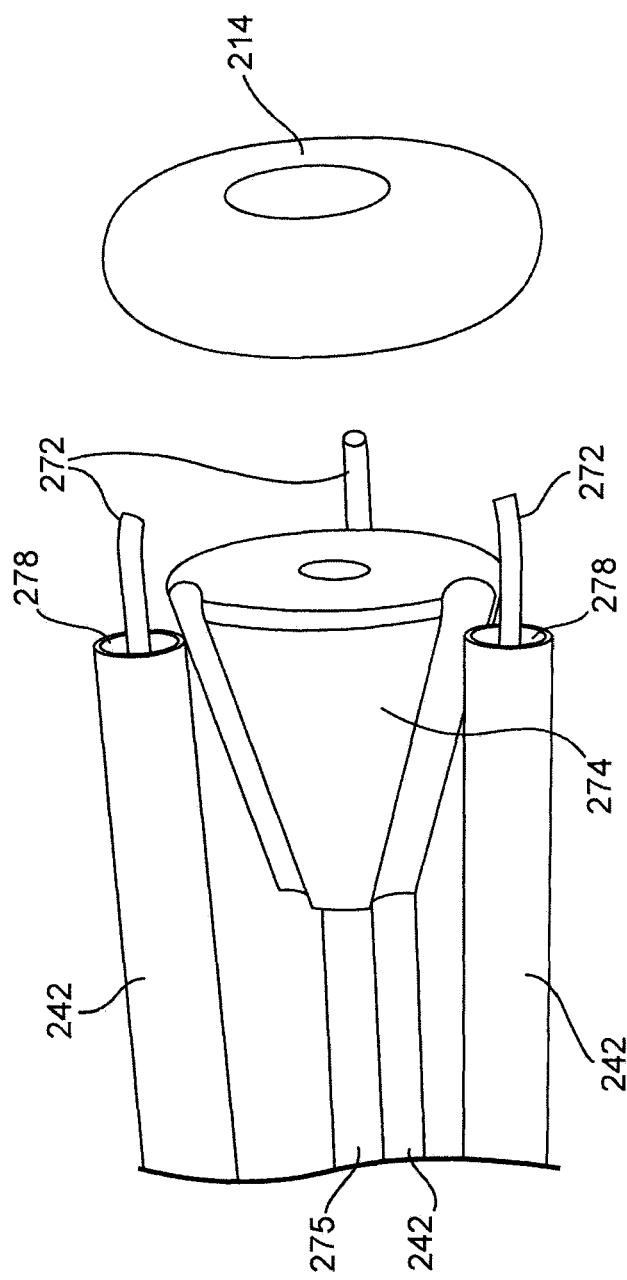

FIG. 78 is a perspective view of a distal portion of one embodiment of a device according to one embodiment of the invention.

Figure 79:
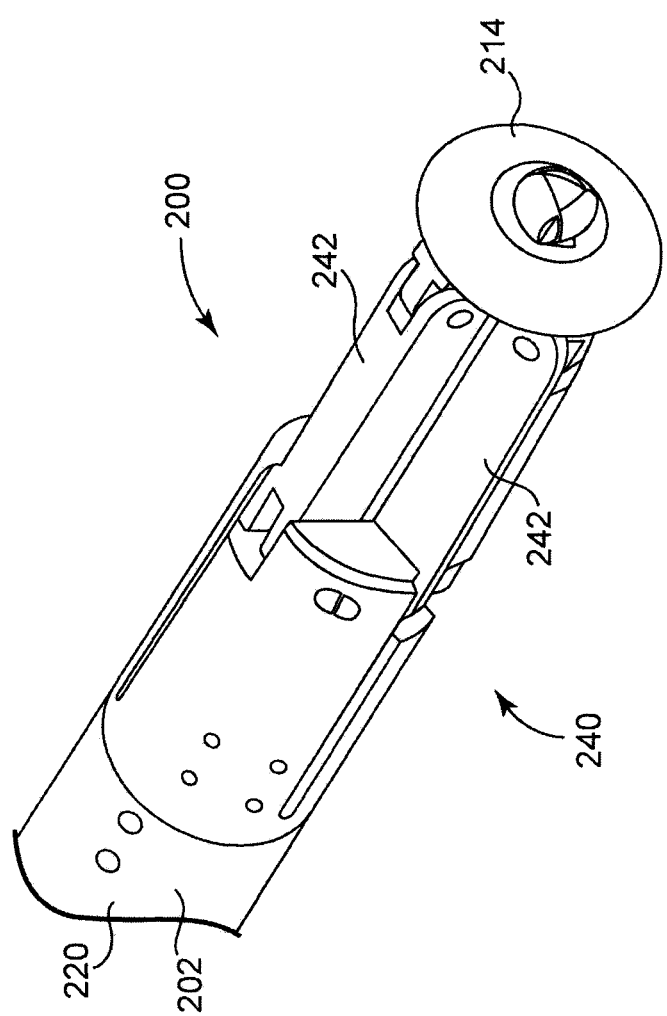

FIG. 79 is a perspective view of a distal portion of one embodiment of a device according to one embodiment of the invention.

Figure 80:
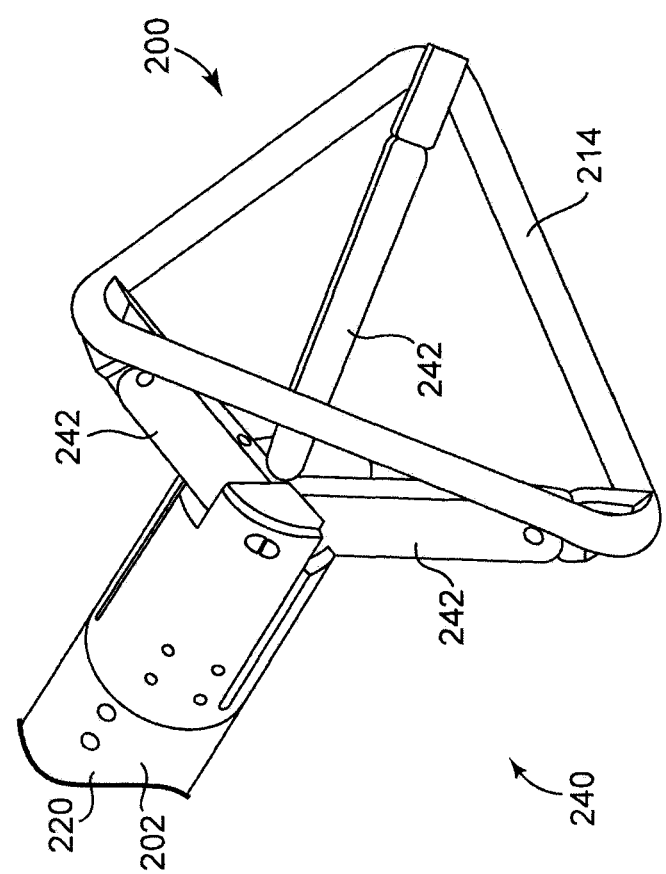

FIG. 80 is a perspective view of a distal portion of one embodiment of a device according to one embodiment of the invention.

Figure 81:
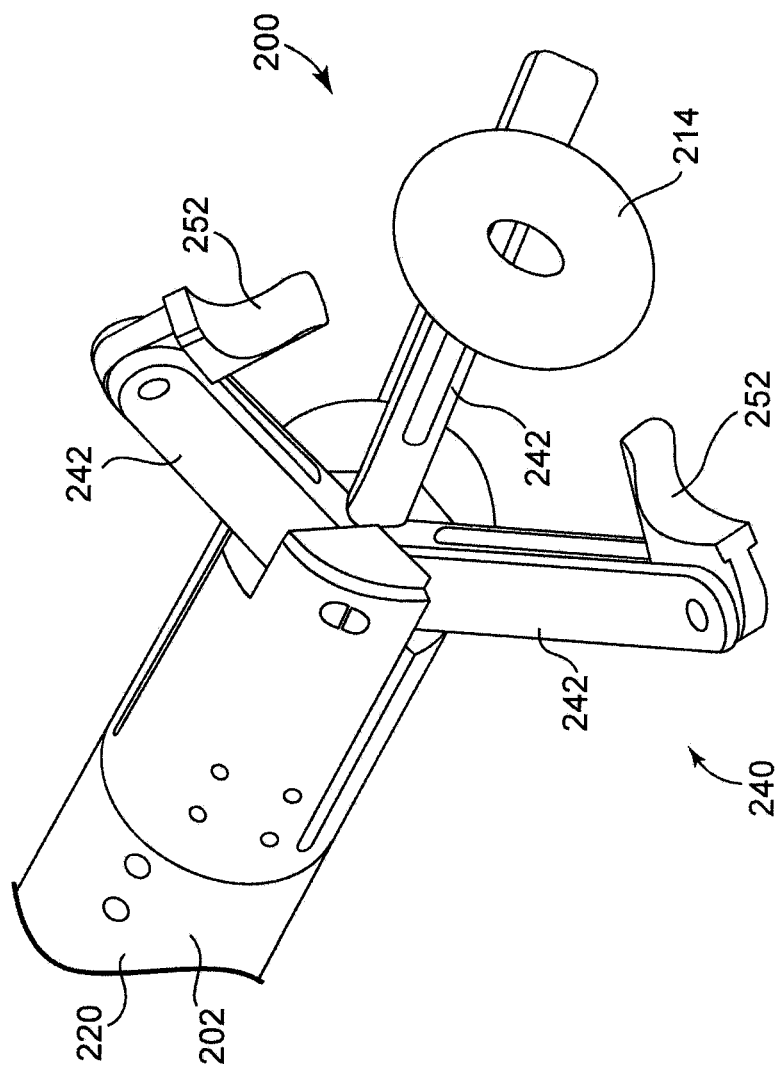

FIG. 81 is a perspective view of a distal portion of one embodiment of a device according to one embodiment of the invention.

Figure 82:
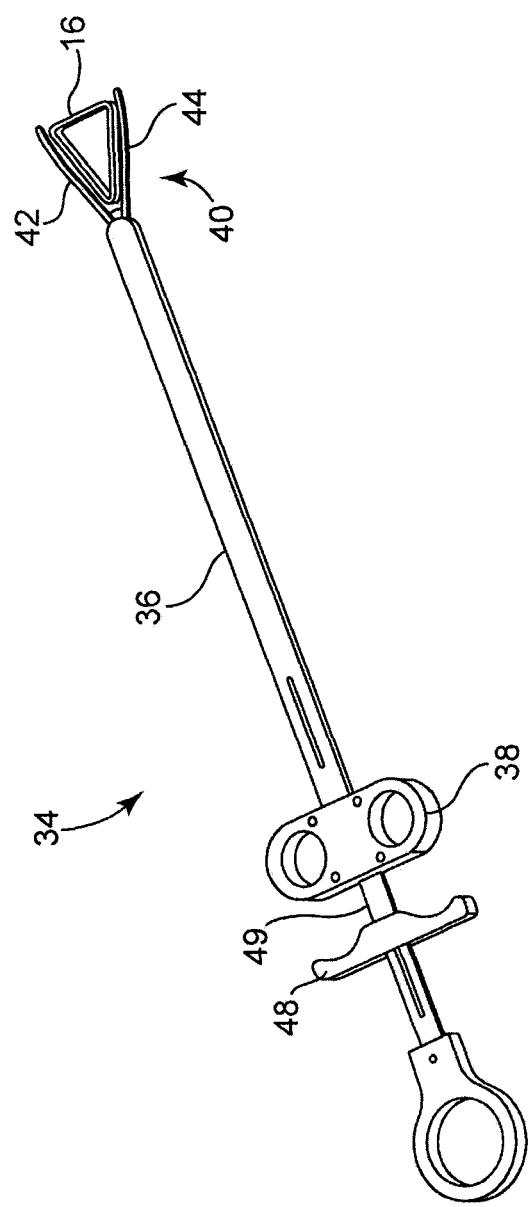

FIG. 82 is a perspective view of one embodiment of a device according to one embodiment of the invention.

Figure 83:
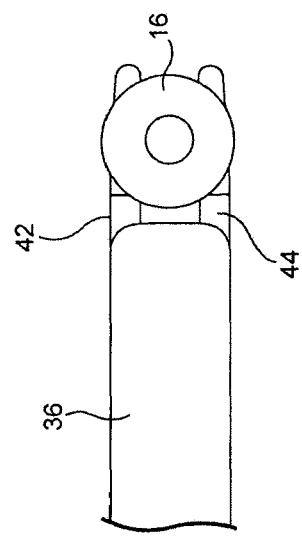

FIG. 83 is a perspective view of a distal portion of one embodiment of a device according to one embodiment of the invention.

Figure 84:
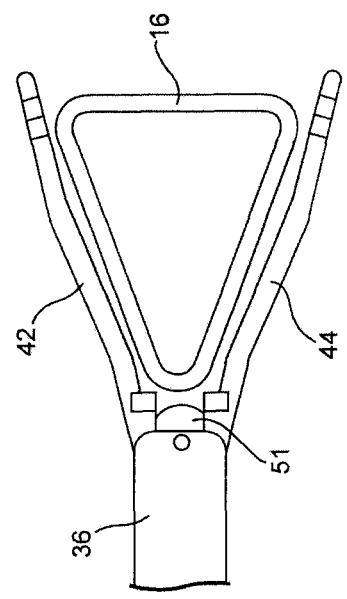

FIG. 84 is a perspective view of a distal portion of one embodiment of a device according to one embodiment of the invention.

Figure 85:
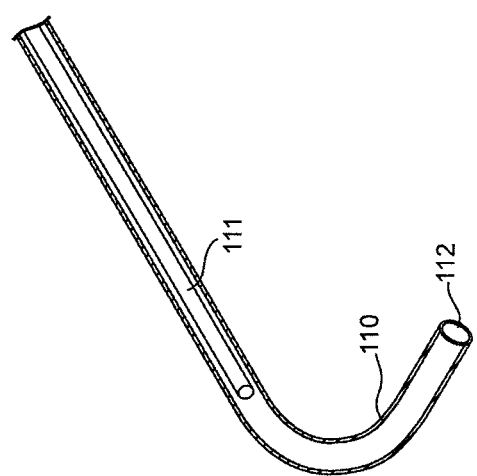

FIG. 85 is a perspective view of a portion of one embodiment of a device according to one embodiment of the invention.

Figure 86:
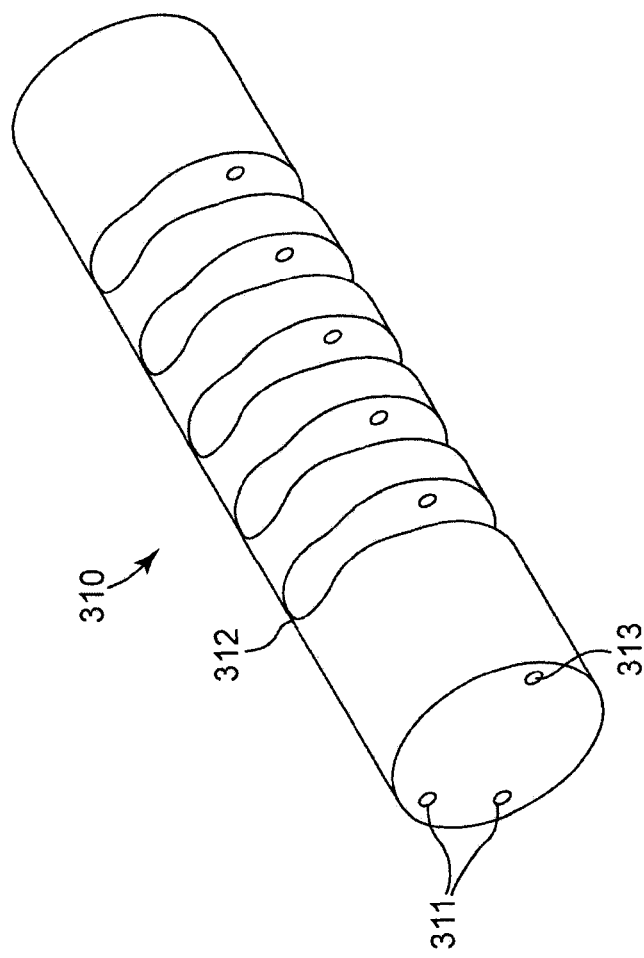

FIG. 86 is a perspective view of a portion of one embodiment of a device according to one embodiment of the invention.

Figure 87:
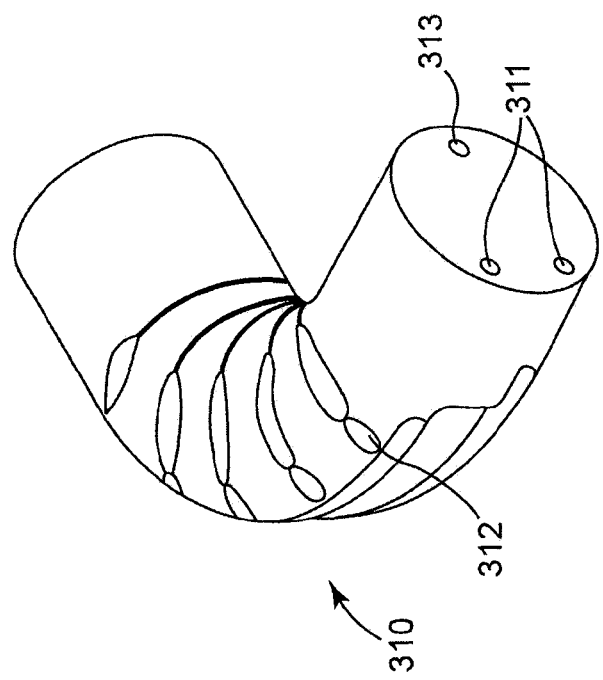

FIG. 87 is a perspective view of a portion of one embodiment of a device according to one embodiment of the invention.

Figure 88:
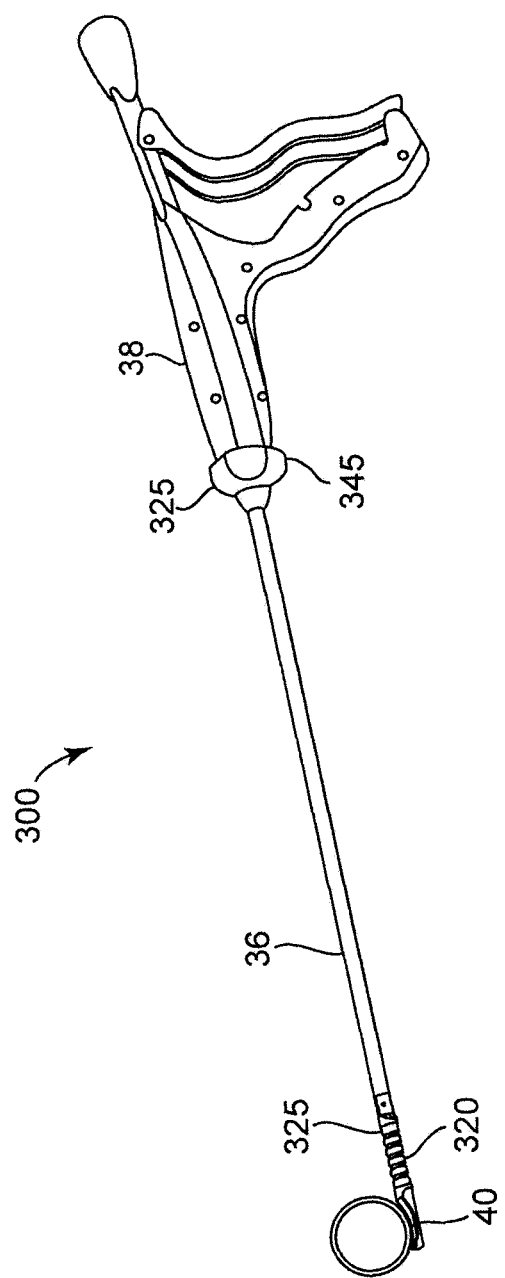

FIG. 88 is a perspective view of one embodiment of a device according to one embodiment of the invention.

Figure 89:
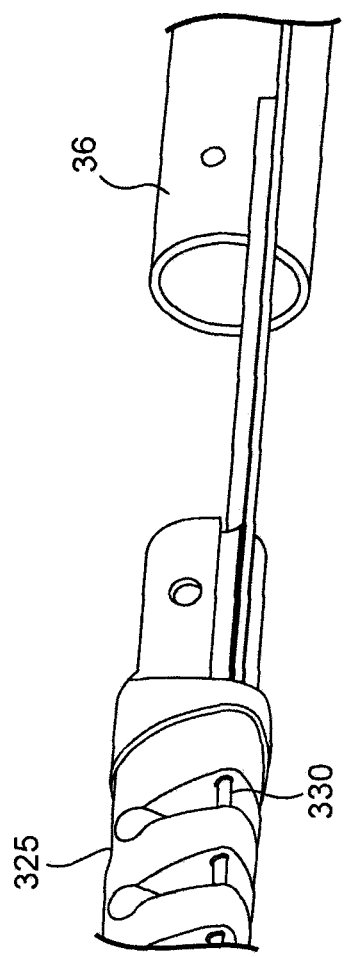

FIG. 89 is a perspective view of a portion of a subassembly of one embodiment of a device according to one embodiment of the invention.

Figure 90:
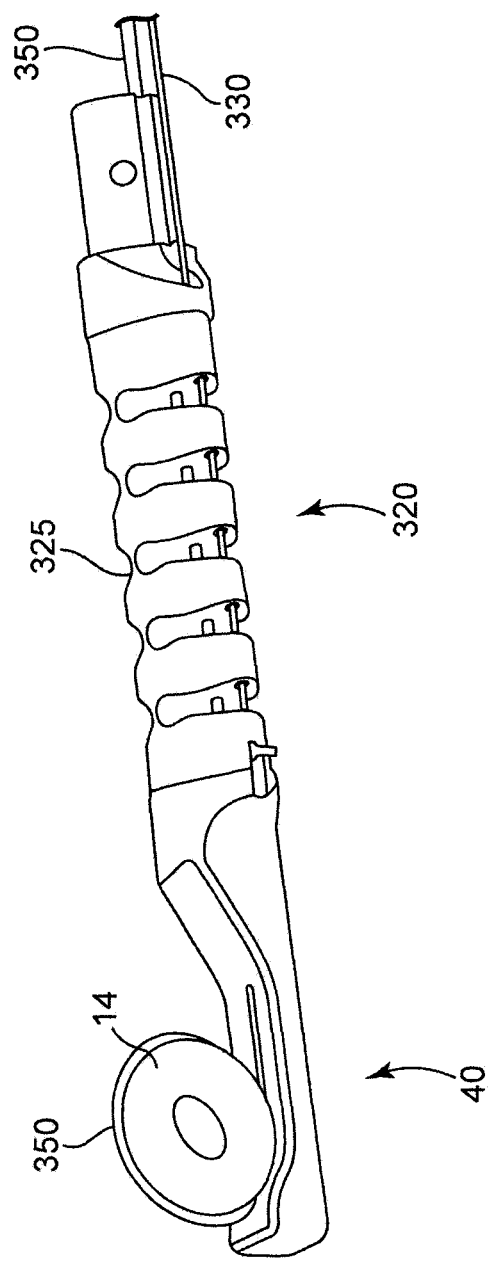

FIG. 90 is a perspective view of a portion of a subassembly of one embodiment of a device according to one embodiment of the invention.

Figure 91:
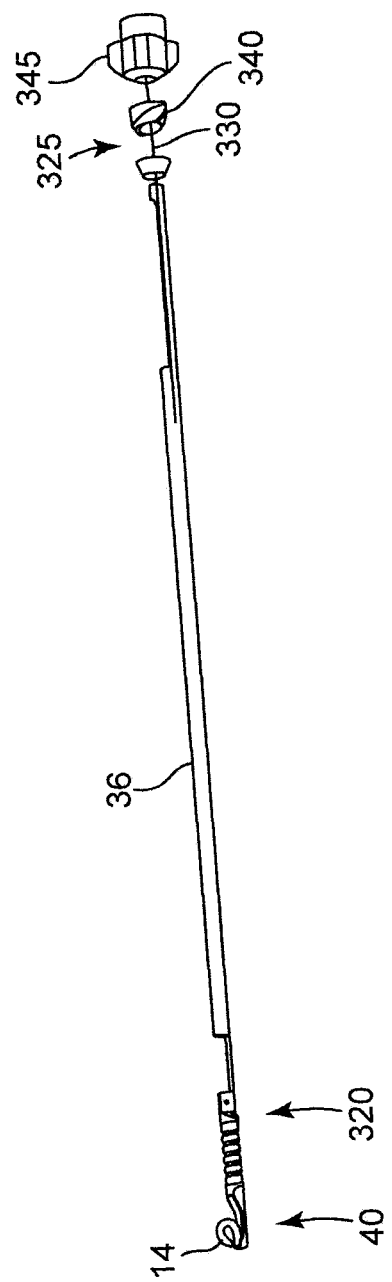

FIG. 91 is a perspective view of a portion of a subassembly of one embodiment of a device according to one embodiment of the invention.

Figure 92:
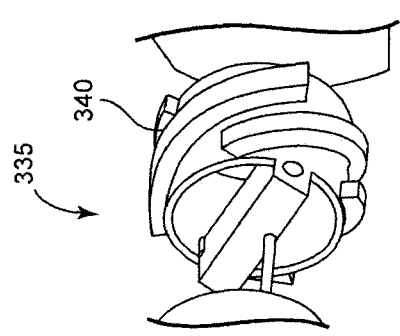

FIG. 92 is a perspective view of a portion of a subassembly of one embodiment of a device according to one embodiment of the invention.

Figure 93:
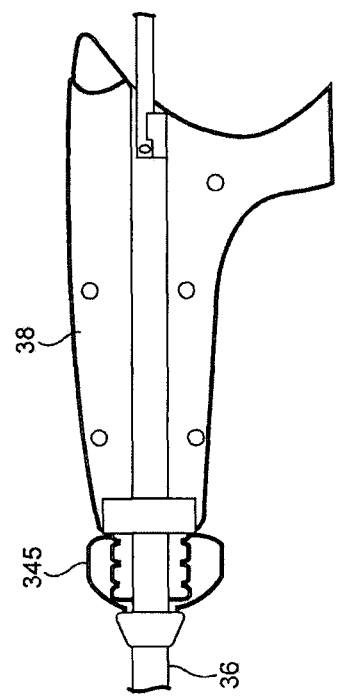

FIG. 93 is a cross-sectional view of a portion of one embodiment of a device according to one embodiment of the invention.

Figure 94:
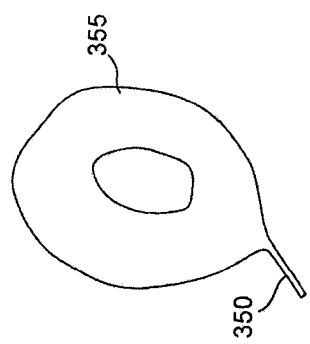

FIG. 94 is a perspective view of one embodiment of a device according to one embodiment of the invention.

Figure 95:
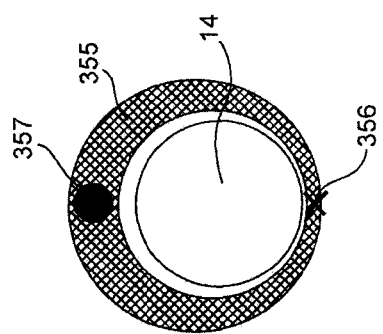

FIG. 95 is a cross-sectional view of one embodiment of a device according to one embodiment of the invention.

Figure 96:
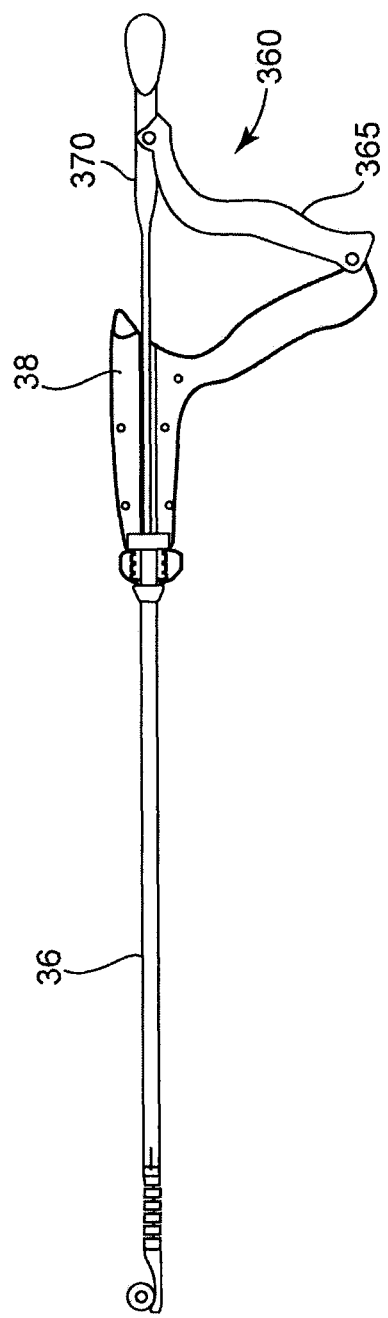

FIG. 96 is a perspective view of one embodiment of a device according to one embodiment of the invention.

Figure 97:
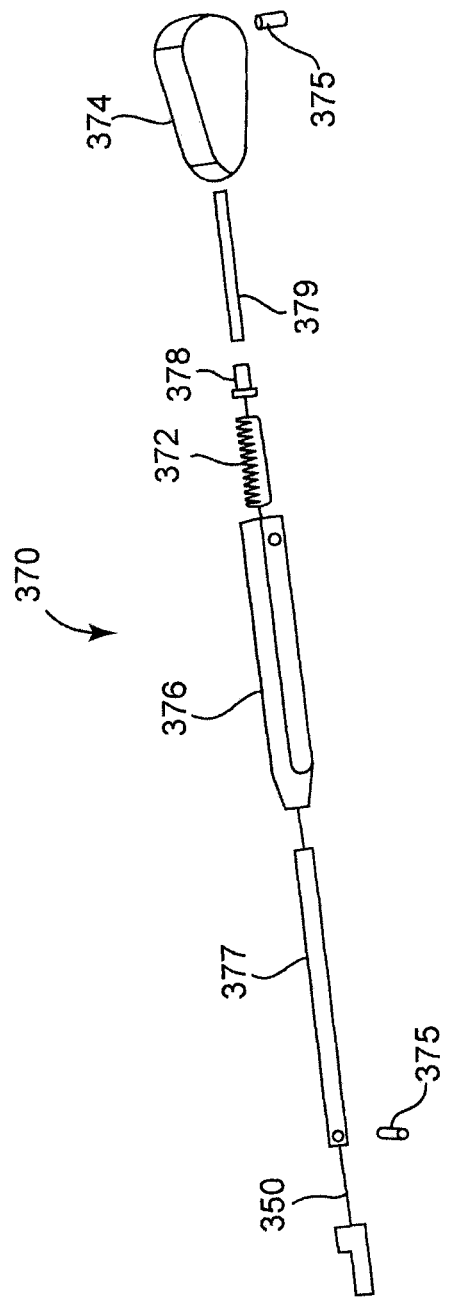

FIG. 97 is a perspective view of a portion of a subassembly of one embodiment of a device according to one embodiment of the invention.

FIG. 98A is a perspective view of a portion of a subassembly of one embodiment of a device according to one embodiment of the invention.

Figure 98B:
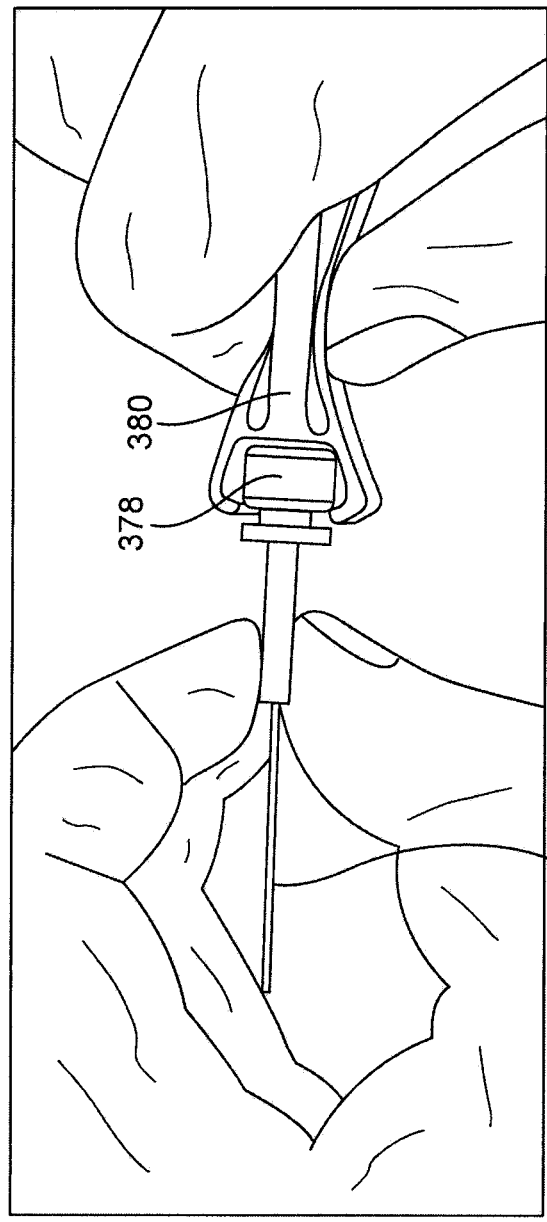

FIG. 98B is a perspective view of a portion of a subassembly of one embodiment of a device according to one embodiment of the invention.

Figure 98C:
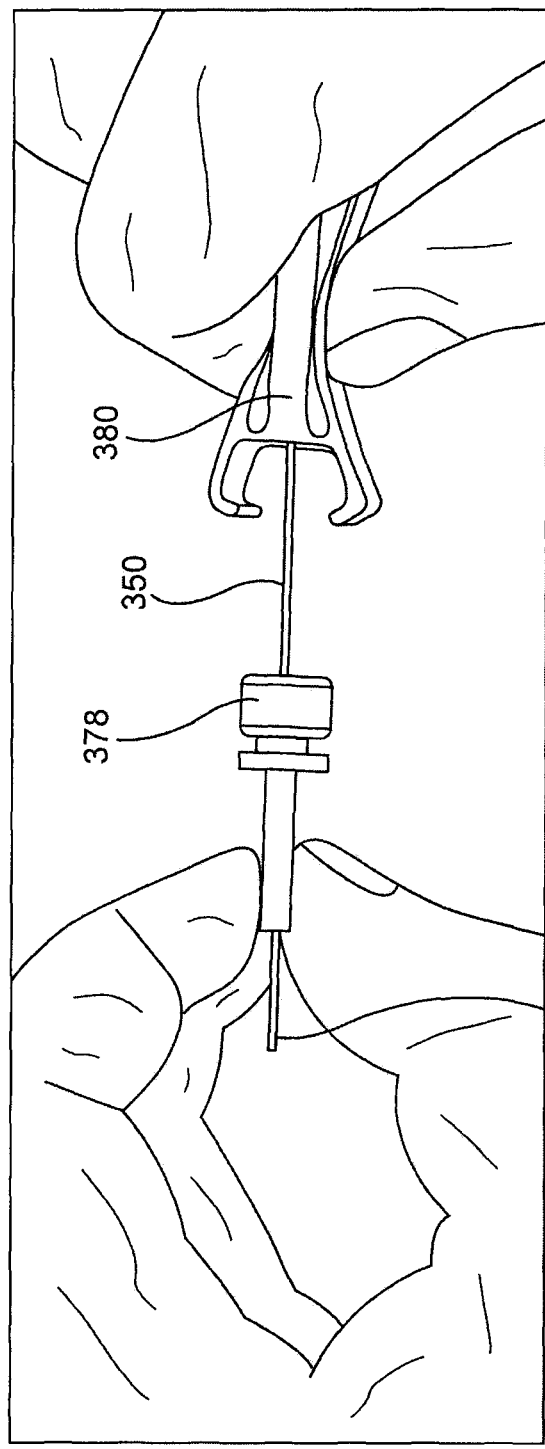

FIG. 98C is a perspective view of a portion of a subassembly of one embodiment of a device according to one embodiment of the invention.

Figure 99:
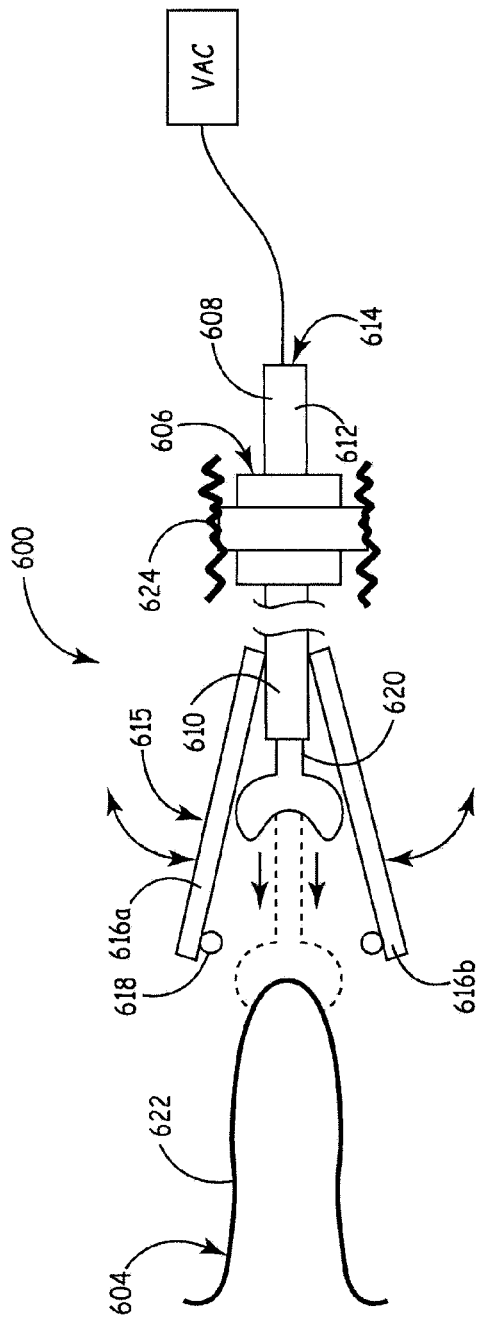

FIG. 99 is a side view of an embodiment of a system for electrically connecting an electrical lead inside a heart.

Figure 100:
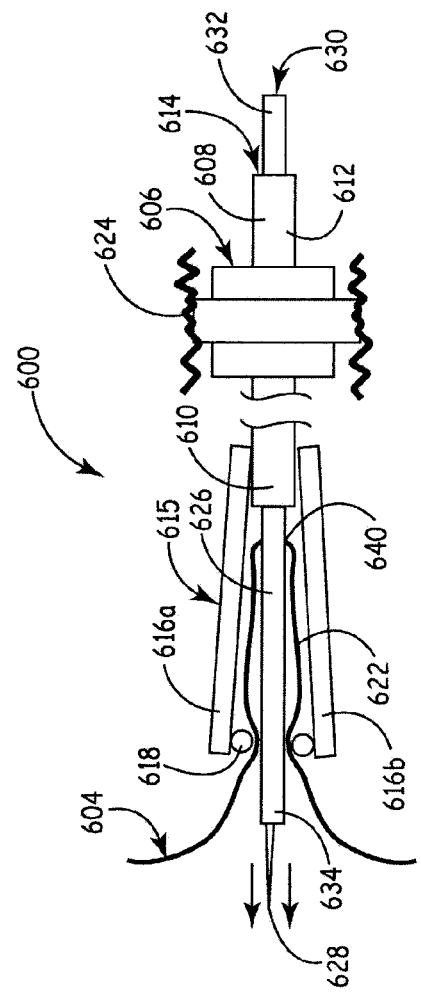

FIG. 100 is a side view of the system of FIG. 99 shown piercing the atrial appendage of the heart.

Figure 101:
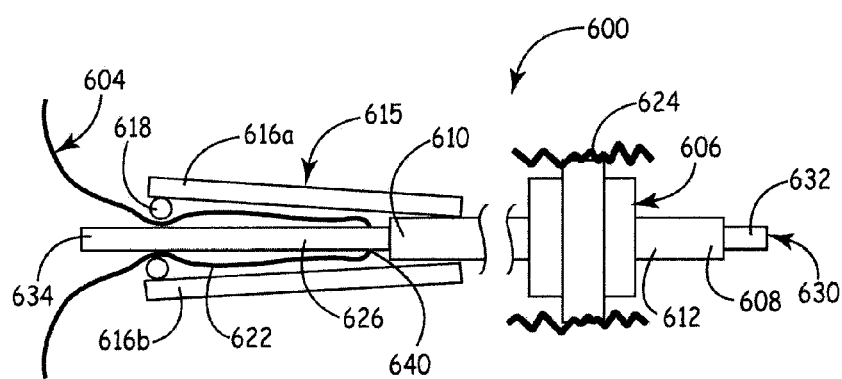

FIG. 101 is a side view of the system of FIG. 99 shown with a lumen extending through the atrial appendage of the heart.

Figure 102:
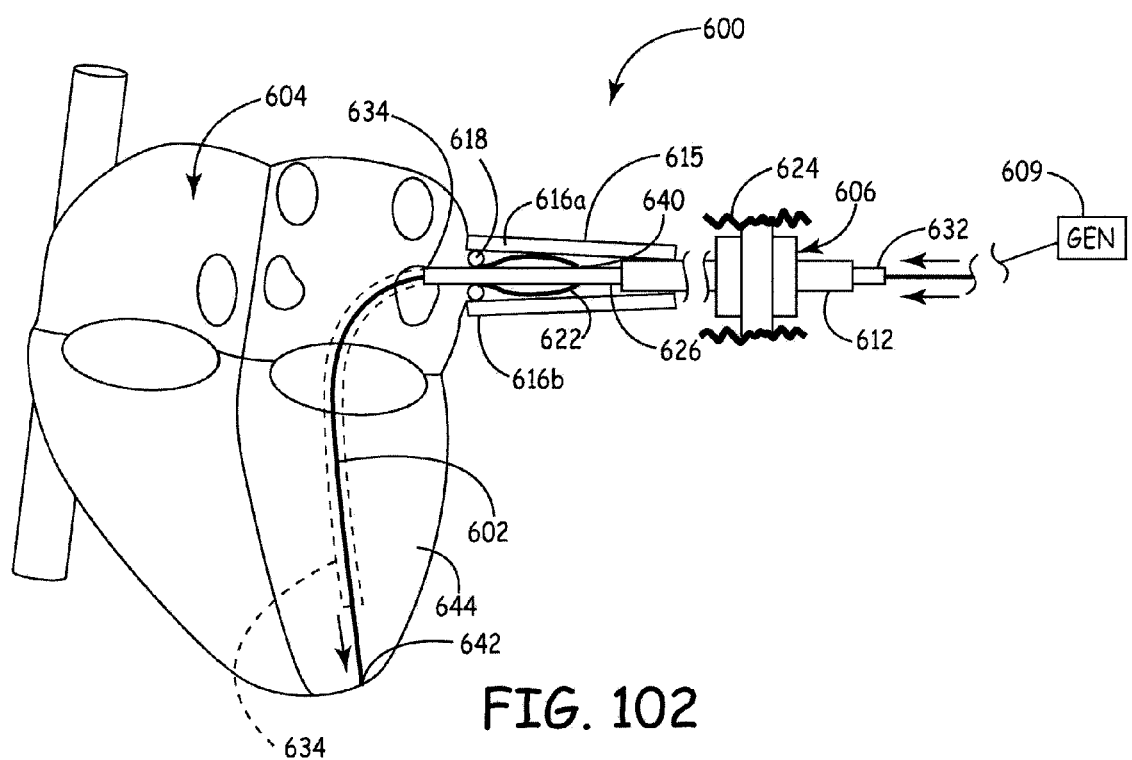

FIG. 102 is a side view of the system of FIG. 99 shown with the electrical lead passing through the system and into the heart.

Figure 103:
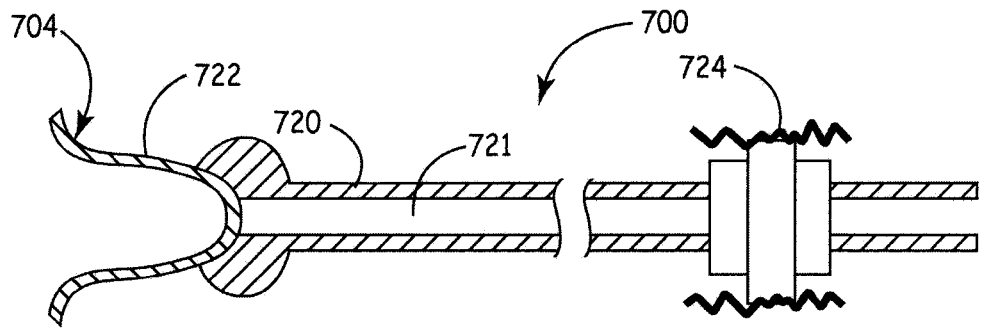

FIG. 103 is a cross-sectional view of another embodiment of a system for electrically connecting an electrical lead inside a heart.

Figure 104:
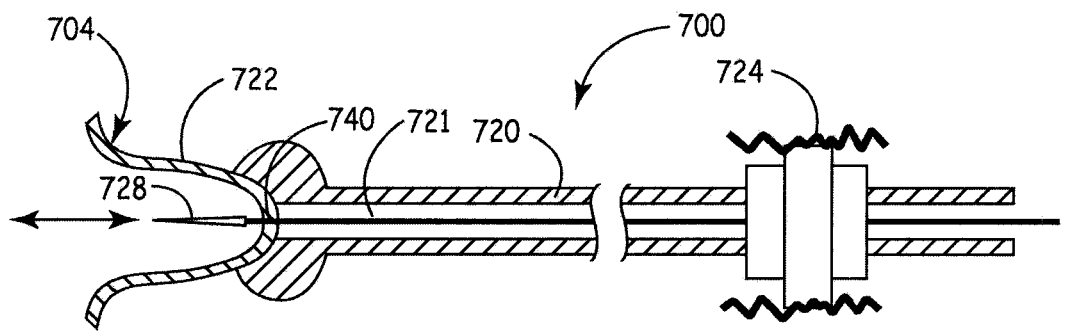

FIG. 104 is a cross-sectional view of the system of FIG. 103 shown piercing the atrial appendage of the heart.

Figure 105:
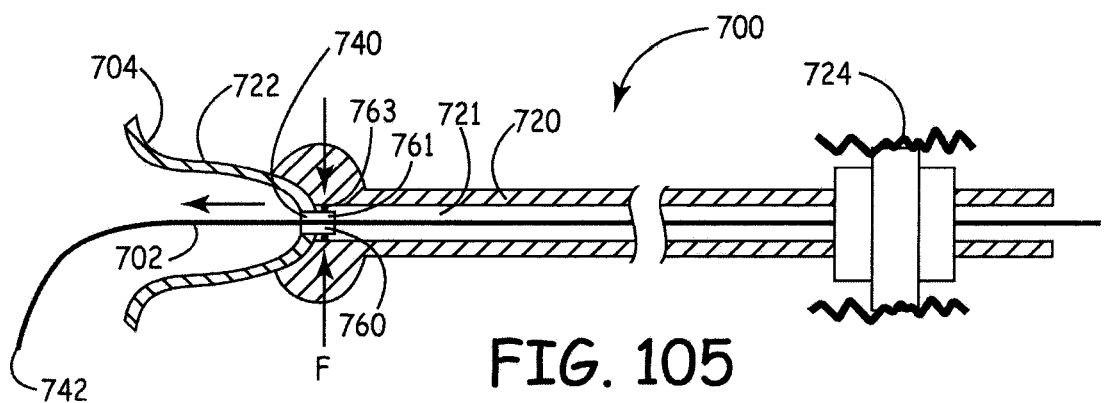

FIG. 105 is a cross-sectional view of the system of FIG. 103 shown with the electrical lead passing through the system and into the heart.

Figure 106:
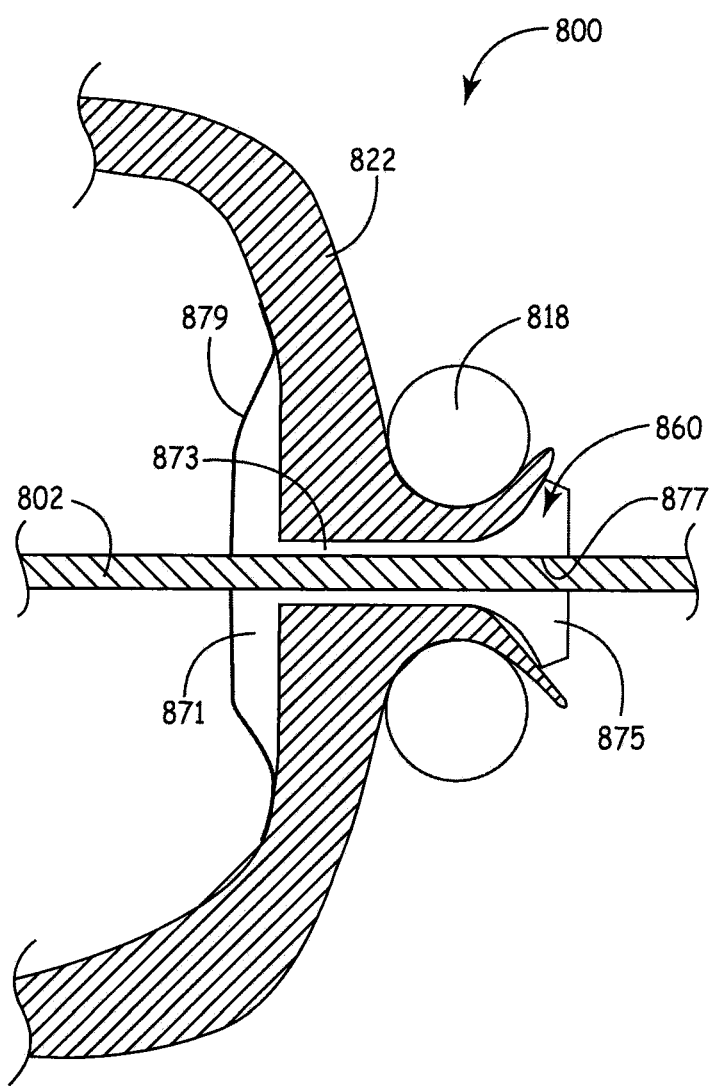

FIG. 106 is a cross-sectional view of another embodiment of a system for electrically connecting an electrical lead inside a heart.

DETAILED DESCRIPTION

Figure 1:
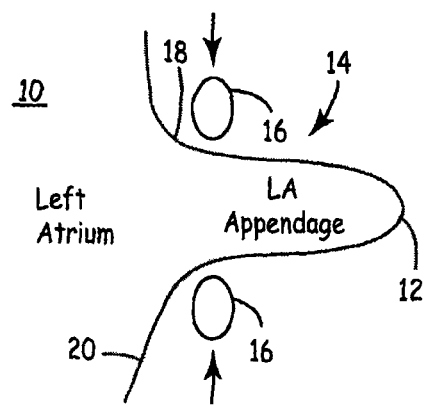
FIG. 1 is a schematic illustration of a left atrial appendage occlusion device according to one embodiment of the invention placed around the left atrium before compressing the tissue of the left atrial appendage.
Figure 2:
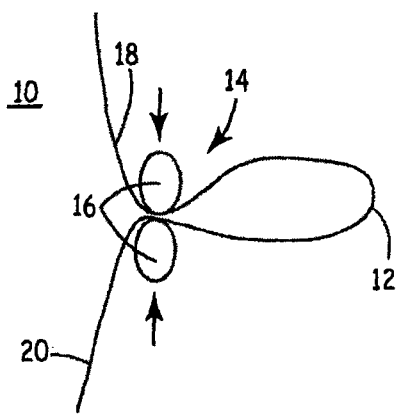
FIG. 2 is a schematic illustration of the left atrial appendage occlusion device of FIG. 1 clamped around the left atrial appendage.

FIG. 1 illustrates an outline of the atrium 10 of the heart with the left atrial appendage 12 protruding therefrom. FIG. 1 also illustrates one embodiment of an occluder 14 forming a ring 16 that is placed in a position to surround the left atrial appendage 12 adjacent to a left atrial appendage base 18, where the left atrial appendage 12 is attached to the heart 20. In some embodiments, the ring 16 can be constructed of an elastic material to allow it to be stretched into an open position, as shown in FIG. 1. The ring 16 can be allowed to return to a closed position, as shown in FIG. 2, to bear against the tissue of the left atrial appendage 12 in order to close off any interior connection between the atrium 10 and the left atrial appendage 12.

Figure 3:
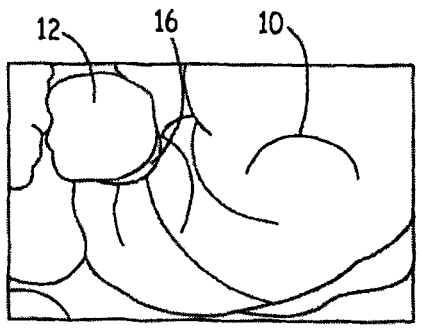
FIG. 3 is a perspective view of a ring occluder on a patient's heart isolating the left atrial appendage.

FIG. 3 illustrates the ring 16 attached to a patient's heart 20 to isolate the left atrial appendage 12 from the atrium 10. In some embodiments, the material of the ring 16 can be biocompatible to allow the ring 16 to be left on the heart 20 permanently. Optionally, the ring 16 may have tissue engaging surfaces for enhanced positionability and/or tissue engagement. The tissue engagement surfaces may comprise bumps, detents, grooves, ridges, ribs or the like. The ring 16 may also include biocompatible coatings for any of the predetermined purposes disclosed herein. The biocompatible coatings may include a pharmacological agent (e.g. a controlled-release agent) for purposes of encouraging tissue ingrowth, affording local apoptosis for therapeutic reasons, local necrosis, revascularizationi, arrhythmia control, infection control, anti-bacterial, fluid balance (i.e. atrial natritic peptide replacement), etc.

Figure 4:
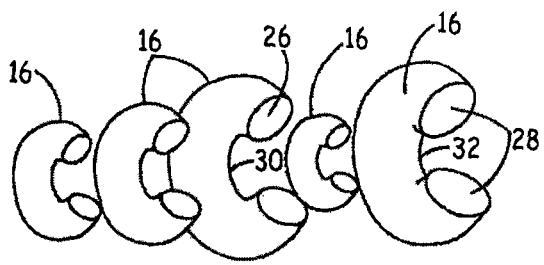
FIG. 4 is a perspective view of a variety of ring occluders illustrating the relative size differences that are available.

FIG. 4 illustrates different relative sizes of rings 16 that can be used to accommodate different anatomy requirements of the patient. In one embodiment, the ring 16 can be manufactured with radio opaque qualities, such as microsized glass beads 26 molded into the material of the ring 16. Alternatively, the ring 16 can be made radio opaque by the addition of glass or metallic fibers 28 in the material of the ring 16. In some embodiments, the ring 16 can be entirely biocompatible to allow for use for the life of the patient. The ring 16 can have size variations in its inner diameter 30 along a contact surface 32. The ring 16 can also have different cross-sectional shapes, such as oval, rectangular, square, etc.

Figure 5:
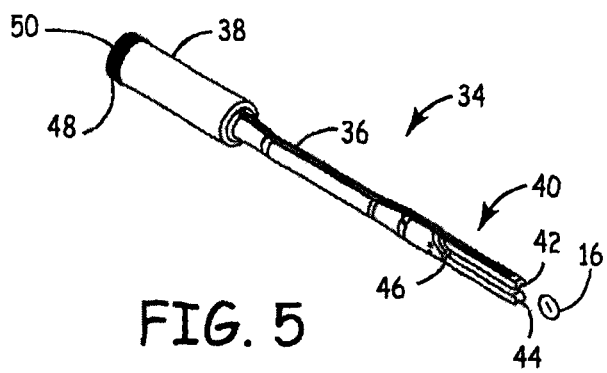
FIG. 5 is a perspective view of a ring occluder applicator according to one embodiment of the invention.

To apply the ring 16 to a patient, a ring applicator 34, as shown in FIG. 5, can be used. In some embodiments, the ring applicator 34 can include a shaft 36 with a handle 38 on a proximal end and a ring spreader 40 on a distal end. The ring spreader 40 can include an upper spreader jaw 42 and a lower spreader jaw 44, each connected to a spreader hinge 46. A jaw actuator 48 on the handle 38 can include a knob 50.

In some embodiments, the spreader hinge 46 can include a four-bar assembly 52 for use in moving the upper spreader jaw 42 and the lower spreader jaw 44 substantially in parallel. The four-bar assembly 52 can include a first distal link 54 and a second distal link 56, as shown in FIG. 6. The first distal link 54 can include a distal end pivotally attached to the upper spreader jaw 42 at a top distal pivot 58. The second distal link 56 can include a distal end pivotally attached to the lower spreader jaw 44 at a lower distal pivot 60. The first distal link 54 can include a proximal end pivotally attached to the shaft 36 and to a proximal end of the second distal link 56 at a distal shaft pivot 57. As a result, the first distal link 54 can be pivotally linked to the second distal link 56.

Figure 8:
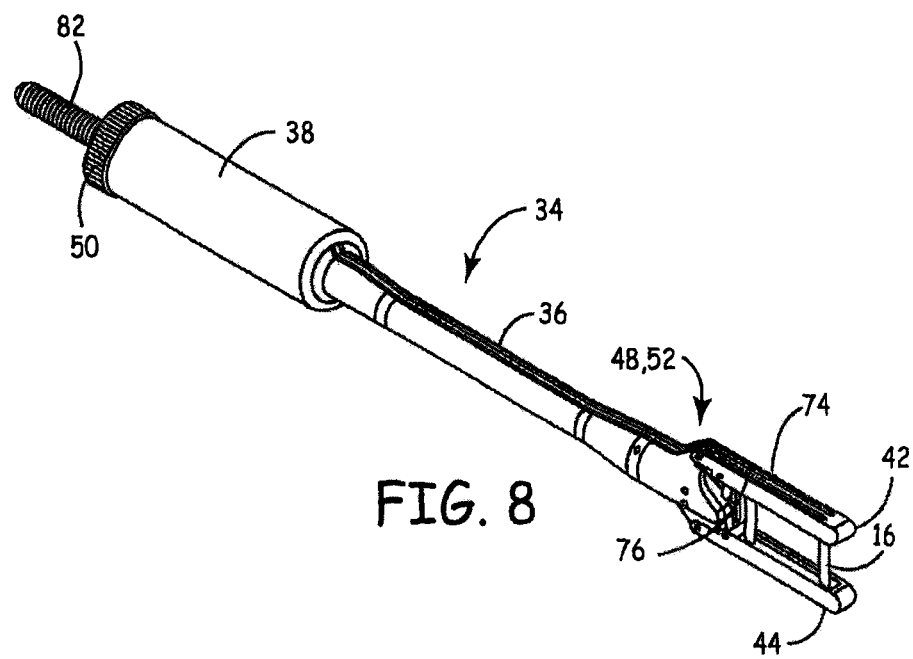
FIG. 8 is a perspective view of the ring occluder applicator of FIG. 5 with a ring occluder attached and in a stretched-open position.
Figure 9A:
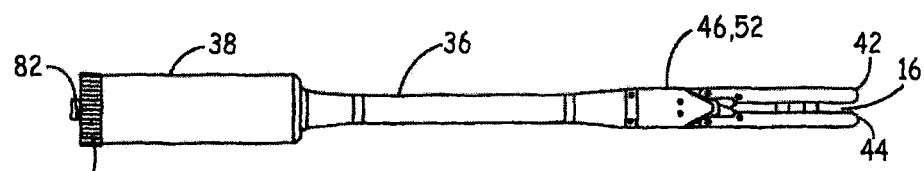
FIG. 9A is a side view of the ring occluder applicator of FIG. 7 with the ring occluder in a relaxed position.
Figure 9B:
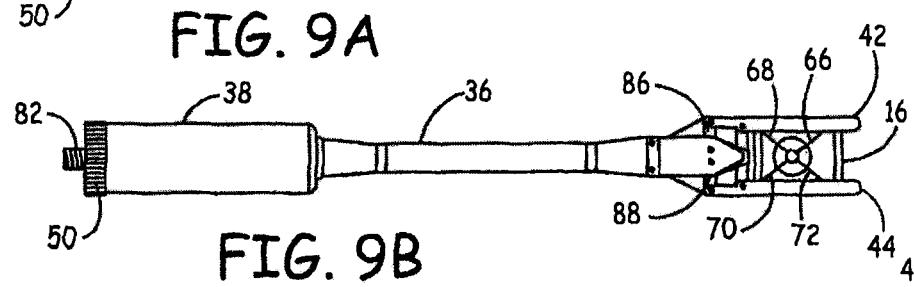
FIG. 9B is a side view of the ring occluder applicator in FIG. 7 with the ring occluder in a partially-stretched open position.
Figure 9C:
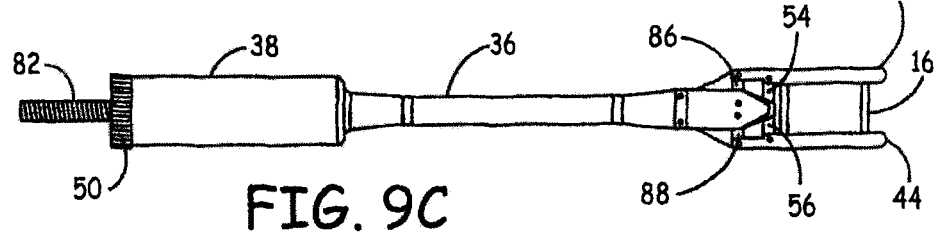
FIG. 9C is a side view of the ring occluder applicator of FIG. 7 with the ring occluder in a stretched-open position.

The ring spreader 40 can be moved from a relaxed closed position (as shown in FIG. 9A) having the upper spreader jaw 42 in close proximity to the lower spreader jaw 44 to an open position (as shown in FIGS. 8, 9B, and 9C) by the jaw actuator 48. In the open position, the upper spreader jaw 42 can be spaced from the lower spreader jaw 44 by a larger distance than in the closed position.

In some embodiments, as shown in FIG. 6, the ring 16 can be removably attached to the ring spreader 40 by one or more sutures tied between the handle 38 and the ring 16. In one embodiment, the ring 16 can be tied on the front, back, top, and bottom to uniformly open the ring 16 for application to a tissue appendage. A front suture 66 and an upper suture 68 can be attached to the jaw actuator 48 and can loop inside the shaft 36 to the upper spreader jaw 42 and around the ring 16 at spaced intervals. A proximal suture 70 and a lower suture 72 can be similarly attached to the jaw actuator 48 and can extend inside the shaft 36 to the lower spreader jaw 44 and around the ring 16 at spaced intervals.

As shown in FIG. 6, the upper spreader jaw 42 can include a first feed slot 74 having a first distal aperture 75 extending through the upper jaw 42 and a first upper aperture 79 extending through the upper jaw 42. The first upper aperture 79 can be disposed between the first distal aperture 75 and the spreader hinge 46. The upper spreader jaw 42 can include a return slot 76 parallel to the first feed slot 74. The return slot 76 can include a second distal aperture 77 in proximity to the first distal aperture 75 and a second upper aperture 81 in proximity to the first upper aperture 79. In some embodiments, the first and second upper apertures 79 and 81 can both extend through the upper jaw 42.

As shown in FIG. 7A, the lower spreader jaw 44 can include a similar configuration to the upper spreader jaw 42. The lower spreader jaw 44 can include a second feed slot 65 with a first lower aperture 67 and a first proximal aperture 69. The first proximal aperture 69 can be disposed between the first lower aperture 67 and the spreader hinge 46. A second return slot 71 can be formed on the lower spreader jaw 44 substantially parallel to the second feed slot 65. The second return slot 71 can include a second lower aperture 73 in proximity to a first lower aperture 67 and a second proximal aperture 53 in proximity to the first proximal aperture 69. The second proximal aperture 53 can be disposed between the spreader hinge 46 and the second lower aperture 73.

The feed slots 65, 74 can be used to direct the sutures attached at the handle 38 to the jaw actuator 48. The sutures 66, 68, 70, 72 can be directed along the spreader jaws 42, 44 and directed to pass through the spreader jaws 42, 44 at the apertures 67, 69, 75, 79. The sutures can 66, 68, 70, 72 then loop around the ring 16 at predefined locations. The sutures 44, 42 can also pass through the apertures 53, 73, 79, 81 and along the return slots 71, 76 to return through a lumen to attach to the jaw actuator 48. The front suture 66 can have a first end attached to the jaw actuator 48. The front suture 66 can extend through the handle 38, along the first feed slot 74, through the first distal aperture 75, and around the ring 16 in a single loop defining the front portion of the ring 16. The front suture 66 can also extend back through the second distal aperture 77, along the first return slot 76, and through the handle 38 to a second end connected to the jaw actuator 48. Likewise, the upper suture 68 can extend through the handle 38, along the first feed slot 74, through the first upper aperture 79, and around the ring 16 in a single loop defining the upper portion of the ring 16. The upper suture 68 can also extend back through the second upper aperture 81, along the first return slot 76, and through the handle 38 to a second end connected to the jaw actuator 48.

The lower suture 72 can have a first end attached to the jaw actuator 48. The lower suture 72 can extend through the handle 38, along the second feed slot 65, through the first lower aperture 67, and around the ring 16 in a single loop defining the lower portion of the ring 16. The lower suture 72 can also extend back through the second lower aperture 73, along the second return slot 71, and through the handle 38 to a second end connected to the jaw actuator 48. Likewise, the proximal suture 70 can extend through the handle 38, along the second feed slot 65, through the first proximal aperture 69, and around the ring 16 in a single loop defining the proximal portion of the ring 16. The proximal suture 70 can also extend back through the second proximal aperture 53, along the second return slot 71, and through the handle 38 to a second end connected to the jaw actuator 48.

FIG. 7 illustrates a torque screw 82 having a hex end 84 channeled in the handle 38 and attached to the jaw actuator 48, according to one embodiment of the invention. When the knob 50 is rotated, the torque screw 82 can rotatably traverse to move the hex end 84 in the handle 38 toward the ring spreader 40 or toward the knob 50, depending on which direction the knob 50 is rotated. The sutures 66, 68, 70, 72 can be attached to the hex end 84 using knots and can extend to loop around the ring 16 in the ring spreader 40. As the knob 50 is turned to traverse the hex end 84 away from the ring spreader 40, the sutures 66, 68, 70, 72 can tighten to bear against the ring 16 and the spreader jaws 42, 44 in order to overcome the elasticity of the ring 16 and move the spreader jaws 42, 44 to the open position, as shown in FIGS. 8 and 9C. The spreader jaws 42, 44 can be guided in a substantially parallel path by the four-bar assembly 52 in order to stretch the ring 16 to the open position. In some embodiments, the hex end and the torque screw 82 are replaced by a linear trigger grip. By squeezing the grip handle, the spreader jaws are spread as described above.

In some embodiments, as shown in FIGS. 9A-9C, the spreader hinge 46 can include a top proximal link 86 and a lower proximal link 88. The top proximal link 86 can include a first end pivotally attached to the shaft 36 and a second end pivotally connected to the upper spreader jaw 42. The lower proximal link 88 can include a first end pivotally connected to the shaft 36 and a second end pivotally connected to the lower spreader jaw 44. The proximal links 86, 88 can function with the distal links 54, 56 to move the upper spreader jaw 42 in a substantially parallel relationship with respect to the lower spreader jaw 44.

The sutures 66, 68, 70, 72 can act as a retainer to hold the ring 16 in the ring spreader 40. The sutures 66, 68, 70, 72 can also act as a portion of the jaw actuator 48 by pulling the ring spreader 40 toward the handle 38 to force the spreader hinge 46 to pivot at the four bar assembly 52, causing the spreader jaws 42, 44 to spread away from one other and stretching the ring 16 open. The sutures 66, 68, 70, 72 can open the ring 16 into a substantially rectangular shape as shown in FIG. 9C.

As shown in FIG. 10, a left atrial appendage chamber 94 can be positioned within a locking clip 96 in an open position. FIG. 11 illustrates the chamber 94 compressed by the locking clip 96 in the closed position. The locking clip 96 can include a lower clip jaw 118 made of an elastic material and an upper clip jaw 124 connected to the lower clip law 118 at a clip hinge 122. In one embodiment, the locking clip 96 can be formed from a single piece of elastic material 120 and can define the clip hinge 122 integrally with the lower clip jaw 118 and upper clip jaw 124. The locking clip 96 can also include a clip lock 126 (e.g., such as a clip barb 128) on the upper clip jaw 124, that is adapted to engage the lower clip jaw 118 at a lock receiver 130 to substantially permanently affix the upper clip jaw 124 to the lower clip jaw 118. FIGS. 12 and 12A illustrate an application of the locking clip 96 on a patient's heart.

FIG. 13 illustrates one embodiment of a clip applicator 98 for delivering a locking clip 96 into a patient through an incision in a closed chest routine. The clip applicator 98 can include a shaft 36 having a handle 38 on a proximal end, a clip actuator 108 on the handle 38, and a locking clip 96 coupled to a distal end.

The clip actuator 108 can be used to move the locking clip 96 from an open, unlocked position to a closed, locked position. The clip actuator 108 can include an actuator suture 110 having a first end attached to the handle 38 and extending through a lumen 112 (as shown in FIG. 14) in the handle 38. The actuator suture 110 can engage the locking clip 96 through a first feed aperture 119 in the lower jaw 118 and can extend through a first actuator aperture 125 in the upper clip jaw 124 of the locking clip 96. The actuator suture 110 can loop over the upper clip jaw 124 and can pass through a second actuator aperture 123 in the upper clip jaw 124. The actuator suture 110 can also extend through a second feed aperture 117 in the lower jaw 118 and back through the handle 38 to a second end attached to the clip actuator 108. Alternatively, the actuator suture 110 can be looped outside the handle 38, so that the operator can pull the actuator suture 110 manually to draw the upper clip jaw 124 to engage the lower clip jaw 118 when the locking clip 96 is in position to engage the left atrial appendage 12.

The first feed aperture 119 can be positioned through the lower clip jaw 118 to allow the actuator suture 110 to pass through the lower clip jaw 118 to the upper clip jaw 124. The upper clip jaw 124 can include the first and second actuator apertures 125, 123 that can allow the actuator suture 110 to loop around the upper clip jaw 124, while retaining a position near the clip lock 126 on the upper clip jaw 124. The clip actuator 108 can be a movable actuator, similar to the torque screw assembly on the ring applicator shown in FIGS. 7 and 8, or alternatively, a thumb slide or lever. The clip actuator 108 can pull the actuator suture 110 to engage the locking clip 96 by pulling the upper clip jaw 124 into engagement with the lower clip jaw 118 at the clip lock 126. The actuator suture 110 can include a first end coupled to the clip actuator 108. The first end can extend through the lumen 112 passing through the lower jaw 118 to loop around the upper clip jaw 124 and back through the lower clip jaw 118 to terminate at the handle 38. In this manner, the clip actuator 108 can bear against the actuator suture 110 to pull on the open end of the upper clip jaw 124 and to overcome the spring tenancy of the clip hinge 122 in order to draw the upper clip jaw 124 into a locking engagement with the lower clip jaw 118.

Figure 15:
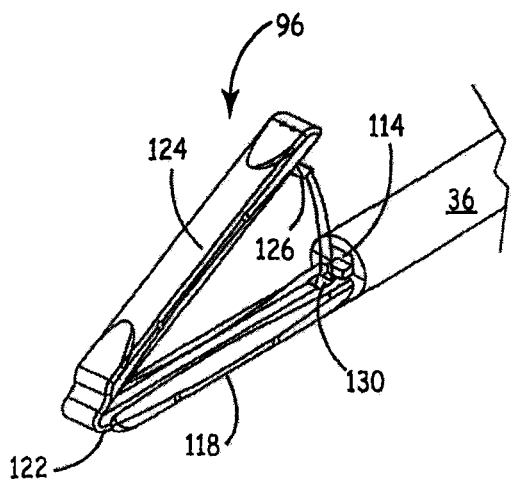
FIG. 15 is a perspective view of the clip applicator of FIG. 14 with the clip attached and in a spring-biased open position.

The lower clip jaw 118 can include an engagement connection 121 to releasably connect the locking clip 96 to the clip applicator 98 with a retention suture 111 (as shown in FIG. 14). The retention suture 111 can removably attach the locking clip 96 to the clip applicator 98. The retention suture 111 can include a first end coupled to the handle 38. The first end can extend from the handle 38 to the locking clip 96 to releasably engage the lower clip jaw 118. As shown in FIG. 14, the retention suture 111 can loop into an engagement portion 121 of the lower clip jaw 118 so that the retention suture 111 may be cut at one end. The retention suture 111 can be cut at the handle 38 to draw the retention suture 111 out of the patient and remove the clip applicator 98, while leaving the locking clip 96 attached to the lower atrial appendage 12. As shown in FIG. 15, the engagement connection 121 can include an aperture in the lower clip jaw 118, adjacent the clip lock 126, that can allow the retention suture 111 to pass into and around a portion of the lower clip jaw 118 and back to the handle 38.

As shown in FIGS. 14-17, a clip stop 114 and two alignment pins 116 can be attached to a distal end of the handle 38. The lower clip jaw 118 can include one or more receivers (not shown) to receive the alignment pins 116 in order to hold the locking clip 96 in alignment with the shaft 36 and to prevent rotation of the locking clip 96 with respect to the shaft 36. The clip stop 114 can include a retractable element in the shaft 36 that can extend out to a position between the lower clip jaw 118 and the upper clip jaw 124. The clip stop 114 can extend out to engage the locking clip 96 as the clip applicator 98 and the locking clip 96 are passed through a lumen, tube, or endoscope, while the operator is inserting the locking clip 96 into a patient, in order to prevent the locking clip 96 from inadvertently locking. After insertion through the lumen, the clip hinge 122 can bear against the clip jaws 118, 124 to open the locking clip 96 for positioning around the base of the left atrial appendage 12 or other target tissue, and the clip stop 114 can be retracted into the shaft 36.

Figure 16:
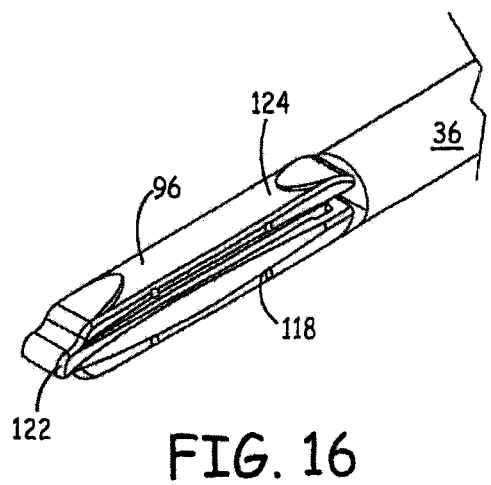
FIG. 16 is a perspective view of the clip applicator of FIG. 14 with the clip attached and in an insert position.

FIG. 16 illustrates the clip 96 in an insertion position in which the clip stop 114 is removably engaged between the upper clip jaw 124 and the lower clip jaw 118. The insertion position can help prevent the clip lock 126 from engaging as clip applicator 98 and the locking clip 96 are passed into a patient's chest through an incision (possibly in a cannula or endoscope). The clip actuator 108 can be used to pull the actuator suture 110 to move the clip stop 114 into the shaft 36 away from the clip jaws 118, 124. The clip actuator 108 can bring the clip jaws 118, 124 into a position to lock the clip lock 126 and to hold the locking clip 96 in a locking position, as shown in FIG. 16.

Figure 17:
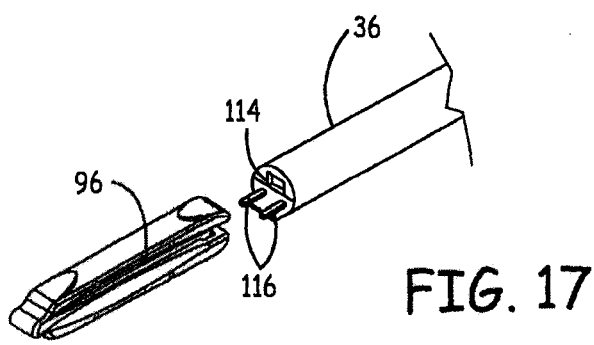
FIG. 17 is a perspective view of the clip applicator of FIG. 14 with the clip detached and in a locked position.

As shown in FIG. 17, the locking clip 96 can be disengaged from the clip applicator 98 by cutting the retention suture 111 at the handle 38 and drawing the retention suture 111 out of the clip applicator 98. Likewise, the actuator suture 110 can be released from the clip actuator 108, can be cut, and can be pulled out of the patient and from the clip applicator 98. The locked locking clip 96 can releasably slide off of the alignment pins 116 and can remain attached to the left atrial appendage 12 when the clip applicator 98 is removed.

Figures 18, 19:
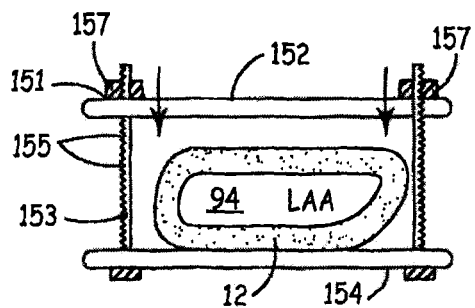
FIG. 18 is a cross-sectional schematic illustration of a left atrial appendage occlusion device according to one embodiment of the invention, before compressing tissue of the left atrial appendage.
FIG. 19 is a cross-sectional schematic illustration of the occlusion device of FIG. 18, after being clamped around the left atrial appendage.
Figure 20:
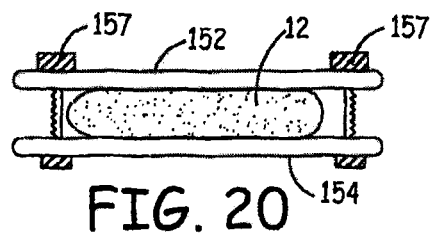
FIG. 20 is a cross-sectional schematic illustration of the occlusion device of FIG. 20 with one or more ratcheting arms removed.
Figure 21:
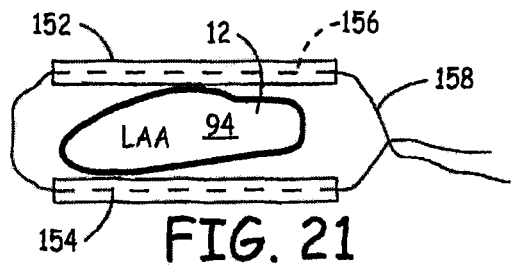
FIG. 21 is a cross-sectional schematic illustration of a left atrial appendage occlusion device according to one embodiment of the invention, before compressing tissue of the left atrial appendage.

FIGS. 18-20 illustrate one embodiment of an occluder including a clamp with a first pressure plate 152 and a second pressure plate 154. The first and second pressure plates 152, 154 can each have one or more end holes 151. A ratcheting mechanism can include teeth 155 on connector rods 153 and a receiver 157 for receiving the connecting rod 153 and engaging the teeth 155 to substantially permanently hold the plates 152, 154 in spaced relation to one other in order to isolate the chamber of the left atrial appendage 12. As shown in FIG. 20, the receivers 157 can be positioned onto the connector rods 153 extending from the second pressure plate 154. The receivers 157 can bear against the first pressure plate 152 to hold the plates 152, 154 in a predefined spaced relation. As shown in FIG. 21, the ends of the connector rods 153 extending from the receivers 157 can be clipped off after the desired clamping is achieved.

Figure 22:
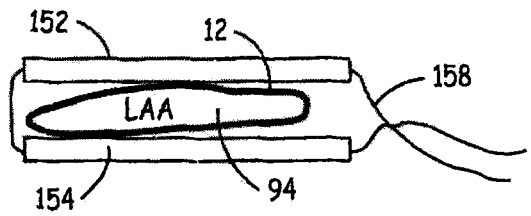
FIG. 22 is a cross-sectional schematic illustration of the occlusion device FIG. 22 after compressing tissue of the left atrial appendage.

FIGS. 21-22 illustrate one embodiment of an occluder in which the pressure plates 152, 154 can be configured with a tie channel 156 passing through each plate 152, 154 from one end to another. A tie 158 can be passed through the tie channels 156 to connect the first and second plates 152, 154 together. The plates 152, 154 can be positioned to clamp down on the base of the left atrial appendage 12 to close off the left atrial appendage chamber 94.

Figures 26, 27:
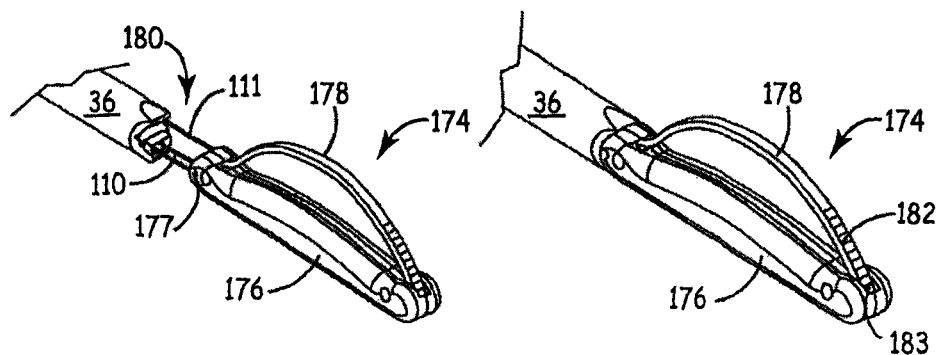
FIG. 26 is a perspective view of the occluder of FIG. 25 being mounted on the applicator of FIG. 23.
FIG. 27 is a perspective view of the occluder fully mounted on the applicator of FIG. 23.

FIGS. 23-29 illustrate one embodiment of a loop clip 174 and a loop clip applicator 172 for engaging the left atrial appendage at its base in order to close the chamber of the left atrial appendage. The loop clip 174 can include a lower clip jaw 176 and a loop 178. The loop 178 can include a fixed end 187 attached to the lower clip jaw 176 and teeth 182 that extend to a slidable end 185. The loop 178 can engage the lower clip jaw 176 at a clip lock 183 to substantially permanently clamp by bearing against tissue trapped between the loop 178 and the lower clip jaw 176. FIG. 26 illustrates an actuator attachment 180 that can include a retention suture 111 extending from the handle 38 to an engagement portion 177 on the loop clip 174. The engagement portion 177 can include an aperture through the loop clip 174 to allow the retention suture 111 to extend from the handle 38, through the shaft 36 around the engagement portion, and back to the handle 38. The retention suture 111 can releasably retain the loop clip 174 on the loop clip applicator 172, until the loop clip 174 is secured around the left atrial appendage. The retention suture 111 can be cut at one end and drawn out of the patient to leave the loop clip 174 engaged.

Figures 24, 25:
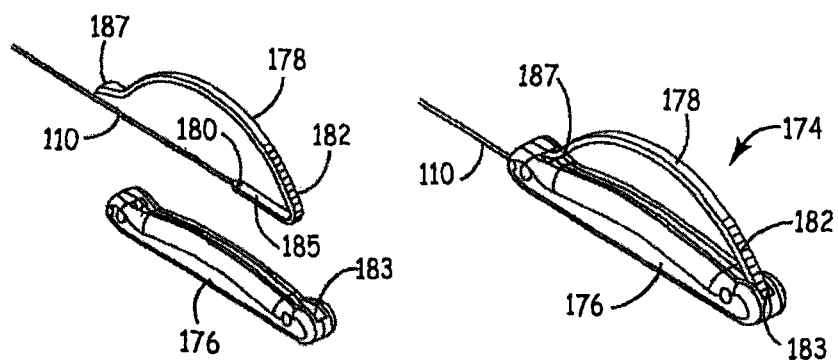
FIG. 24 is an exploded perspective view of the occluder of FIG. 23.
FIG. 25 is a perspective view of the occluder of FIG. 24 after assembly.

FIG. 24 illustrates an actuator suture 110 attached to the slidable end 185 of the loop clip 174. The actuator suture 110 can be removably attached to the slidable end 185 of the loop 178 by looping through an actuator aperture 180. The fixed end 187 of the loop 178 can be attached to the lower clip jaw 176 while the remainder of the loop 178 having teeth 182 can slidably engage the clip lock 183.

Figure 23:
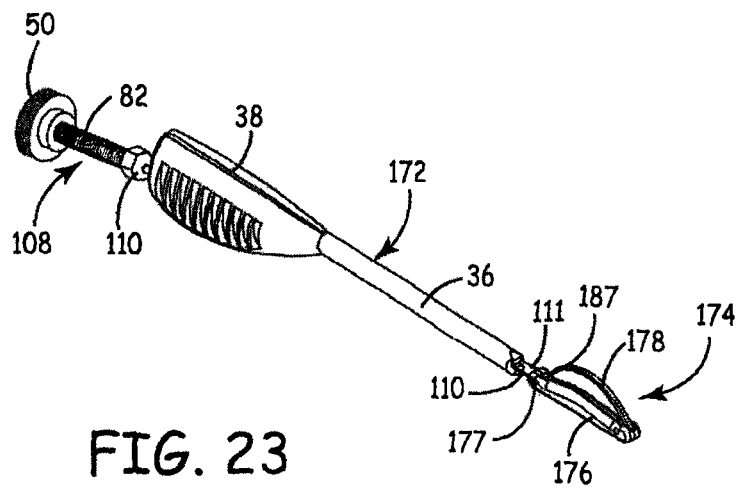
FIG. 23 is a perspective view of an applicator for inserting and applying a left atrial appendage occluder according to one embodiment of the invention.

As shown in FIG. 27, the loop clip 174 can be attached to the loop clip applicator 172 and maintained in an insertable position. The loop clip 174 and the shaft 36 can be inserted into the patient's chest to bring the loop 178 to a position adjacent the left atrial appendage 12. The loop clip 174 can be manipulated to a position where the lower jaw clip 176 is adjacent the base of the left atrial appendage 12 and the loop 178 extends around the left atrial appendage 12. The actuator suture 110 can be attached to an actuator 108, which can include a knob 50 and a torque screw 82, as shown in FIG. 23. The knob 50 can be turned to traverse the hex head of the torque screw 82 to bear against the actuator suture 110 in order to pull the slidable end 185 of the loop 178 through the clip lock 183 where the teeth 182 can be engaged by the lower jaw clip 176 to substantially permanently hold the loop 178 in position. The knob 50 can be turned until the loop 178 is pulled as tight as desired against the tissue of the left atrial appendage 12 in order to isolate the chamber from the atrium. Alternatively, the actuator suture 110 can be looped outside the handle 38 to be pulled manually by the operator to lock the loop clip 174 in relation the lower clip jaw 176. Other embodiments of the actuator 108 can include a linear trigger grip, a linear slider, etc.

Figures 28, 29:
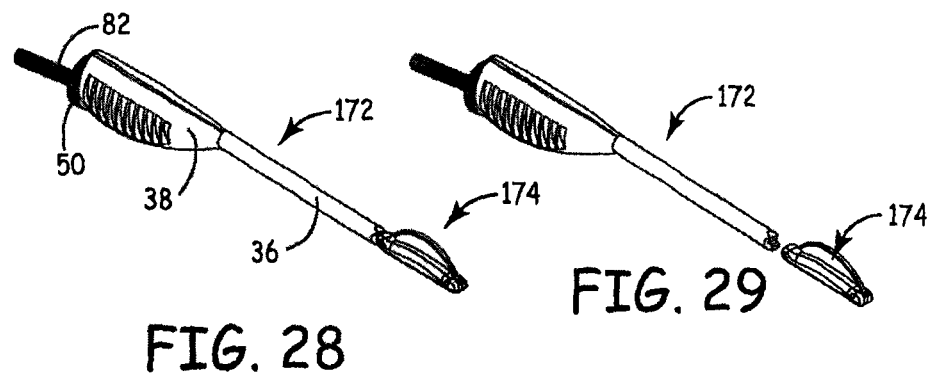
FIG. 28 is a perspective view of the occluder compressed on the applicator of FIG. 23.
FIG. 29 is a perspective view of the occluder compressed and disconnected from the applicator of FIG. 23.

As shown in FIG. 28, the loop clip 174, which is shown in a position for encircling and occluding the left atrial appendage to close the chamber 94, can be disengaged from the loop clip applicator 172 by cutting one end of the retention suture 111 and pulling the retention suture 111 from around the engagement portion 177 and out of the patient's body. As shown in FIG. 28, the loop 178 can be engaged by the teeth 182 to the lower clip jaw 176 to a closed position. The loop 178 can be disengaged from the loop clip applicator 172 by cutting one end of the actuator suture 110 and pulling the actuator suture 110 through actuator aperture 180 and out of the patient.

Some embodiments of the invention provide a tool designed to place a ring style left atrial appendage occlusion device. The tool can include a handle with a long neck. An upper and a lower jaw can be attached to the handle with a four-bar assembly on a distal end and a knob 50 and a torque screw 82 on a proximal end. Some embodiments of the tool can include four separate sutures (2 front and 2 rear) that can loop around a ring and then into the upper and lower jaws. The sutures can be positioned in slots on outside edges of the upper and lower jaws and down into the handle. A retaining suture can be positioned through the lower jaw of a ring into a distal end of the handle, and the loop can be completed outside a proximal end of the tool. The retaining suture can be used to pull and then hold the ring tight against the distal end of the handle. Two holes can be positioned in an end of the lower jaw of the ring. Alignment pins can be inserted into the two holes to help hold and position the ring. After routing through the handle, the retaining suture can be positioned into the hex end of the torque screw and through to the other side where the retaining suture are then tied off.

According to some embodiments of a method of the invention, a port can be placed in the patient's chest so that when the ring is placed and opened, the left atrial appendage can be pulled into the opening with a grasper, a vacuum source (e.g. a cone), an adhesive tool tip, a cryo device for temporarily sticking to tissue, etc. A neck of the tool can include articulation to aid in placement of the ring. A distal end of the tool can be guided through the port and placed near the left atrial appendage. As the torque screw is turned, the upper and lower jaws open parallel to one another. Continuing to turn the torque screw stretches the ring open. Other methods of actuation can be used to pull the sutures, such as a trigger, slider, etc. When the ring is fully opened, the left atrial appendage can be pulled between the upper and lower jaws until properly located. The torque screw can be turned in the opposite direction to release tension on the sutures and relax the ring around the left atrial appendage. The torque screw can be tightened and relaxed multiple times, if necessary to achieve proper placement. Once the ring is properly positioned, the sutures can be cut (either near the ring or on a proximal end of the tool) to release the ring, and the tool can be retracted. An inside edge of the port can be used to close the upper and lower jaws so the tool can be removed.

Other embodiments of the invention provide a tool designed to place a clip style left atrial appendage occlusion device. The clip can be a rigid one-piece clip with a snap-in lock on one end. The clip can also include a living hinge that is spring biased open on the other end. However, other embodiments of the tool can be used with other types of rigid clips, as well as a different hinge or latching mechanism. The tool can include a handle with a long neck. Two separate suture loops can be positioned along the length of the handle inside the neck. A stop on a distal end of the tool can be actuated on a proximal end of the tool. An actuation suture can be positioned through an upper clip jaw of the left atrial appendage clip, then through a lower clip jaw, into a distal end of the handle and complete a loop outside a proximal end of the handle. A port can be created in the patient's chest such that when the clip is positioned near the left atrial appendage, the left atrial appendage can be pulled between the upper and lower clip jaws with a grasper. The neck on the tool can articulate to aid in placement of the clip. The stop can be placed in its forward position to keep the upper clip jaw from latching while pushing it through the port. The clip can spring open after it has passed through the port. The handle can be used to position the clip near the left atrial appendage and the left atrial appendage can be pulled between the upper and lower clip jaws with a grasper. Once the clip is positioned on the left atrial appendage as desired, a stop actuation knob 50 can be pulled back to retract the stop. The actuation suture can be pulled (or actuated with a trigger, slide, screw, etc.) until the upper clip jaw snap latches into the lower clip jaw. The left atrial appendage is then occluded. The sutures can be cut and pulled through the handle, which can release the clip. The sutures can be cut with a scalpel, scissors, or other surgical instruments, or the sutures can be cut with a mechanism that is built into the tool itself. The tool can then be removed from the port.

Some embodiments of the invention provide a tool designed to place a loop-clip style left atrial appendage occlusion device. The tool can include a handle with a long neck. The tool can include two separate suture loops that can be positioned through the length of the handle and a shaft. The tool can include a knob 50 and a torque screw on a proximal end of the handle and the shaft. The loop clip 174 can include a rigid base with a flexible loop that can include one-way teeth molded into it. The loop can wrap around one end of the rigid member and through a slot with a locking snap (like a cable tie). This allows the loop to be pulled in, but not release. The end of the loop can include a hole that a suture can be routed through. The suture can be positioned into the distal end of the placement device, can be positioned through the handle, into the hex end of the torque screw, and tied off on an opposite end. A retaining suture can be positioned through a hole in an end of the loop clip, then into a distal end of the placement device, positioned through the handle, and tied off on a proximal end of the tool. The retaining suture can be used to pull and hold the loop clip tight against a distal end of the handle. An alignment boss on an end of the handle can be inserted into a matching slot on the loop clip to ensure proper alignment. A port can be created in the patient's chest so that when the loop clip is positioned, the left atrial appendage can be pulled between the loop and the base with a grasper. The neck on the placement tool can articulate to aid in placement of the loop clip. The flexible loop can be pushed down to place the loop clip through the port, then once it is through, the loop can return to its original shape. The handle can be used to position the loop clip near the left atrial appendage and the left atrial appendage can be pulled inside the loop with a grasper. Once the loop clip is positioned on the left atrial appendage as desired, turning the torque screw can gradually tighten the loop (a trigger, slide, etc. could also be used to tighten the loop). The torque screw can be turned until the loop is tight enough to occlude flow and remain securely placed. After the loop is tight enough, the actuation suture and the retaining suture can be cut and pulled through the handle. The tool can then be removed from the port.

Some embodiments of the invention include a device and method for occlusion or ligation of an atrial appendage or other tissue. The method and applicators disclosed herein describe a minimally invasive approach to ligation of an atrial appendage, specifically, of the left atrial appendage of patients with atrial fibrillation. Some embodiments of the invention include a method and apparatus to access the left appendage through a small incision and the use of a delivery tool to apply an occluder to the appendage. The tool can be used to grasp the appendage to help stabilize the appendage to allow for application of the ligation device. The ligation device may be applied and left behind as a permanent implant.

Some embodiments of the invention include a device and procedure that can occlude the left atrial appendage from the body of the left atrium—thereby substantially preventing the formation of a clot within the appendage and a subsequent embolism. Some embodiments of the invention include an implantable device and applicator for substantially permanently occluding the left atrial appendage. Some embodiments of the invention include a device and procedure that is minimally invasive to apply a device as a simple and quick method to deliver therapy to prevent embolic strokes. Some embodiments of the invention include a device and procedure that does not require the use of blood-contacting biomaterials. Some embodiments of the invention include a device and procedure that results in tissue necrosis at the left atrium/left atrial appendage junction that is necessary to help prevent reentry. Some embodiments of the invention include a device and procedure that places a device to occlude while preserving the tissue of the left atrial appendage for the production of atrial hormones. Some embodiments of the invention include a device and procedure with a substantially permanently implanted clamp used for occluding the left atrial appendage. Some embodiments of the invention include a device and procedure that is applied from the exterior of the heart, which may be accessed by a sternotomy, thorocotomy, minimally invasive, endoscopic or other means. Some embodiments of the invention include a device and procedure that may be practiced by a number of different embodiments of the clamping mechanism as disclosed herein.

Figure 30:
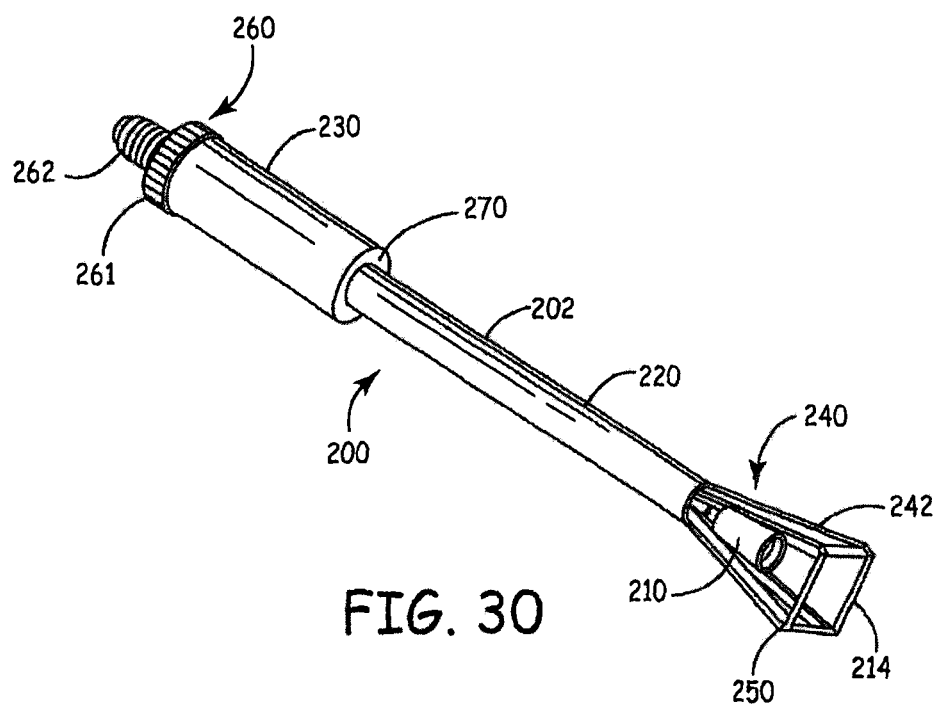
FIG. 30 is a perspective view of one embodiment of a device according to one embodiment of the invention.

FIG. 30 illustrates a device 200 for ligation of an atrial appendage. The device 200 can include a ring applicator or delivery tool 202 and an occlusion member or ring 214. In one embodiment, the occlusion ring 214 can be made of a 30 A durometer silicone rubber, although other hardnesses of silicone or other materials, such as polyurethane can be used. The ring 214 can be covered with a material such as Dacron® polyester to promote tissue ingrowth or prevent ring slippage after placement or to spread the load bearing surfaces of the ring. The ring 214 can be generally expandable for placement around the atrial appendage. The delivery tool 202 can be used to expand the ring 214. The delivery tool 202 can include a shaft 220 and a handle 230 coupled to shaft 220. The delivery tool 202 can be sized for reaching an atrial appendage through an opening in the patient's chest, for example, through a sternotomy or thoracotomy. The delivery tool 202 can include a tissue-grasping member 210. The tissue-grasping member 110 can be a mechanical grasping member, for example, hooks, barbs, or graspers, or it can be a suction grasping member (as shown in FIG. 30), or it can be an adhesive. The delivery tool 202 can include one or more suction lumens fluidly coupled to suction grasping member 210. The suction lumens can pass through the shaft 220 and/or handle 230, or portions thereof. The suction grasping member 210 can be coupled to a suction source. The tissue-grasping member 210 can be used to grasp the atrial appendage and pull it through ring 214. In one embodiment, the tissue-grasping member 210 can be moved distally and/or proximally relative to shaft 220. In one embodiment, the delivery tool 202 can include a mechanism for controllably moving the tissue-grasping member 210. This mechanism can be located at or near the handle 230.

The delivery tool 202 can include a ring spreader 240 having ring-expanding members 242 used to hold and expand the ring 214. The ring spreader 240 can be coupled to a distal end of shaft 220. In one embodiment, the delivery tool 202 can include multiple ring-expanding members 242, for example, four, as shown in FIG. 30. Alternatively, the delivery tool 202 can include three or five expanding members 242, for example. The ring 214 can be releasably coupled or attached to a distal end of ring-expanding members 242, for example, via one or more sutures 250. The sutures 250 can loop around the ring 214. The ends of the sutures 250 can pass through one or more lumens within the ring expanding members 242, the shaft 220, and the handle 230. In one embodiment, one or more portions of the sutures 250 can be exposed at or near distal or proximal ends of the handle 230. For example, portions of sutures 250 can be exposed at a suture cutting location 270. Exposure of the sutures 250 at or near the handle 230 can enable the release of the ring 214 from the delivery tool 202 remotely. In one embodiment, the sutures 250 can be cut and removed, thus releasing the ring 214 from the delivery tool 202. Cutting the sutures 250 can release the ring 214 from the ring-expanding members 242. In one embodiment, the delivery tool 202 can include one or more suture cutting members.

As shown in FIG. 30, the handle 230 can include a ring expansion mechanism 260 used to control the expansion of the ring 214. The ring expansion mechanism 260 can be coupled to the ring-expanding members 242. The ring expansion mechanism 260 can control movement of the ring expanding members 242 from a closed or collapsed configuration to an open or expanded configuration, as shown in FIG. 30. In one embodiment, the ring expansion mechanism 260 can include a screw mechanism. The ring expansion mechanism 260 can control movement of the ring-expanding members 242 into and out of shaft 220. The pulling of the ring-expanding members 242 into the shaft 220 can collapse the ring expanding members 242 into a closed configuration. The pushing of the ring-expanding members 242 out of the shaft 220 can expand the ring expanding members 242 into an open configuration. The ring-expanding members 242 can be spring biased into an open expanded configuration. In one embodiment, the ring expansion mechanism 260 can be located at or near distal or proximal ends of the handle 230. In one embodiment, the ring expansion mechanism 260 can include one or more knobs 261 and one or more threaded members 262, as shown in FIG. 30.

Figure 31:
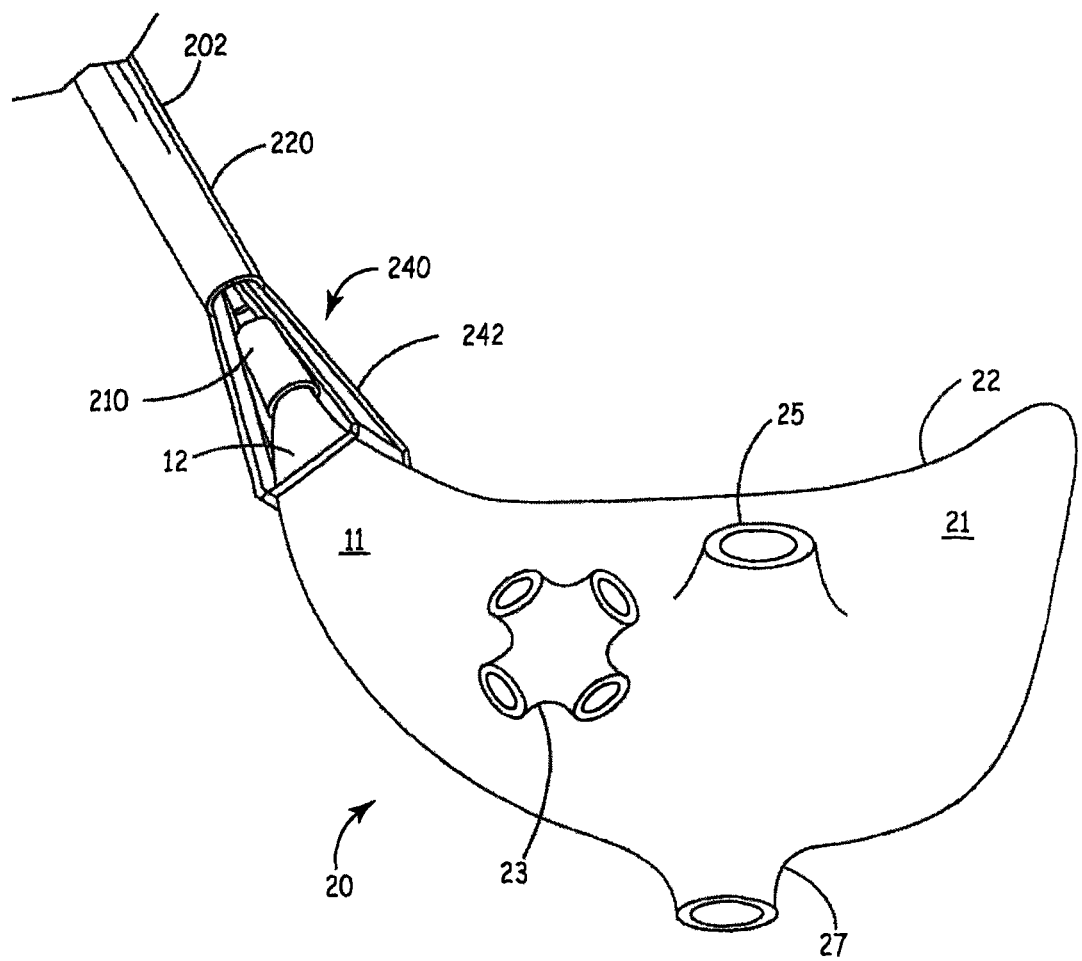
FIG. 31 is a partial perspective view of the device of FIG. 30 in use.

As shown in FIG. 31, the delivery tool 202 can be placed around the left atrial appendage 12 of a heart 20. FIG. 31 schematically illustrates the structure of the left and right atria 11 and 21, respectively, as viewed from a posterior aspect, including the bases of the pulmonary veins 23 and the bases of the superior vena cava and inferior vena cava 25 and 27, respectively, which enter the right atrium 21. FIG. 31 also schematically illustrates the left and right atrial appendages 12 and 22, respectively.

Figures 32, 33:
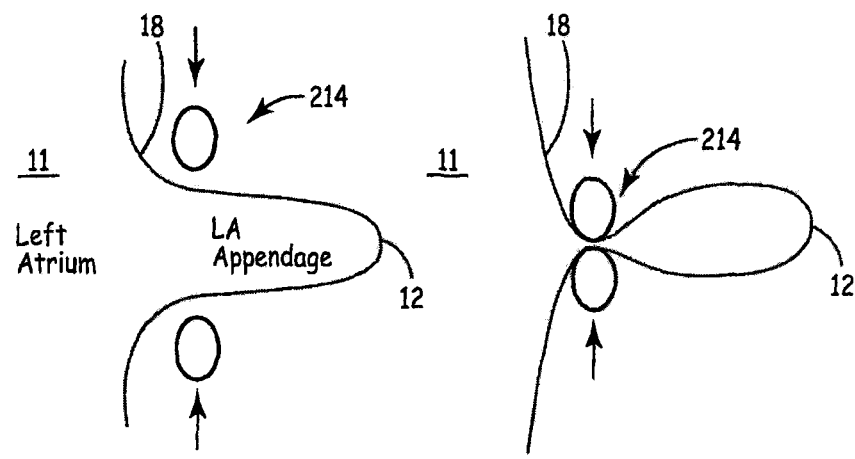
FIG. 32 is a schematic illustration of an occlusion device according to one embodiment of the invention positioned around the left atrial appendage.
FIG. 33 is a schematic illustration of the occlusion device of FIG. 32 clamped around the left atrial appendage.

FIGS. 32 and 33 schematically illustrate an outline of the left atrium 11 of the heart 20 with the left atrial appendage 12 protruding therefrom. The ring 214 can be placed in a position to surround the left atrial appendage 12 adjacent to the left atrial appendage base 18 where the left atrial appendage 12 is attached to the heart 20. The ring 214 can be made of an elastic material to allow it to be stretched into an open or expanded position, as shown in FIG. 32. The ring 214 can be allowed to return to a closed or collapsed position, as shown in FIG. 33, in order to bear against the tissue of the left atrial appendage 12 and to substantially close off any interior connection between the left atrium 11 and the left atrial appendage 12.

As shown in FIG. 32, the ring 214 can be attached to a patient's heart 20 to isolate the left atrial appendage 12 from the left atrium 11. In some embodiments, multiple rings 214 can be placed successively more and more proximal to the base 18 of the left atrial appendage 12. The elastic material of the ring 214 can be any biocompatible material, thereby allowing the ring 214 to be left on the heart 20 permanently. In one embodiment, the ring 214 can have different relative sizes to accommodate different anatomy requirements of the patient. The ring 214 can be manufactured with radio opaque qualities, such as micro-sized glass beads molded into the elastic material. Alternatively, the ring 214 can be made radio opaque by the addition of glass or metallic fibers in the elastic material. The ring 214 can be entirely biocompatible to allow for use for the life of the patient. The ring 214 can have size variations in its inner diameter along a contact surface.

In one embodiment, surgical access to the left atrial appendage can be through a left-sided thoracotomy or laproscopic port incision. The delivery tool and attached collapsed ring can be inserted through the left thoracotomy access. The ring can then be expanded. The left atrial appendage can be grasped and drawn or pulled through the expanded ring. The ring can be positioned toward the base of the left atrial appendage and released from the delivery tool. The delivery tool can then be removed from the patient, and the incision can be closed. Various imaging methods can be employed before, during, and after the tissue occlusion procedure. For example, contrast fluoroscopy, trans-thoracic ultrasound, and/or transesophageal echo (TEE) can be employed. Other surgical approaches are possible including sub-xyphoid.

Figure 34:
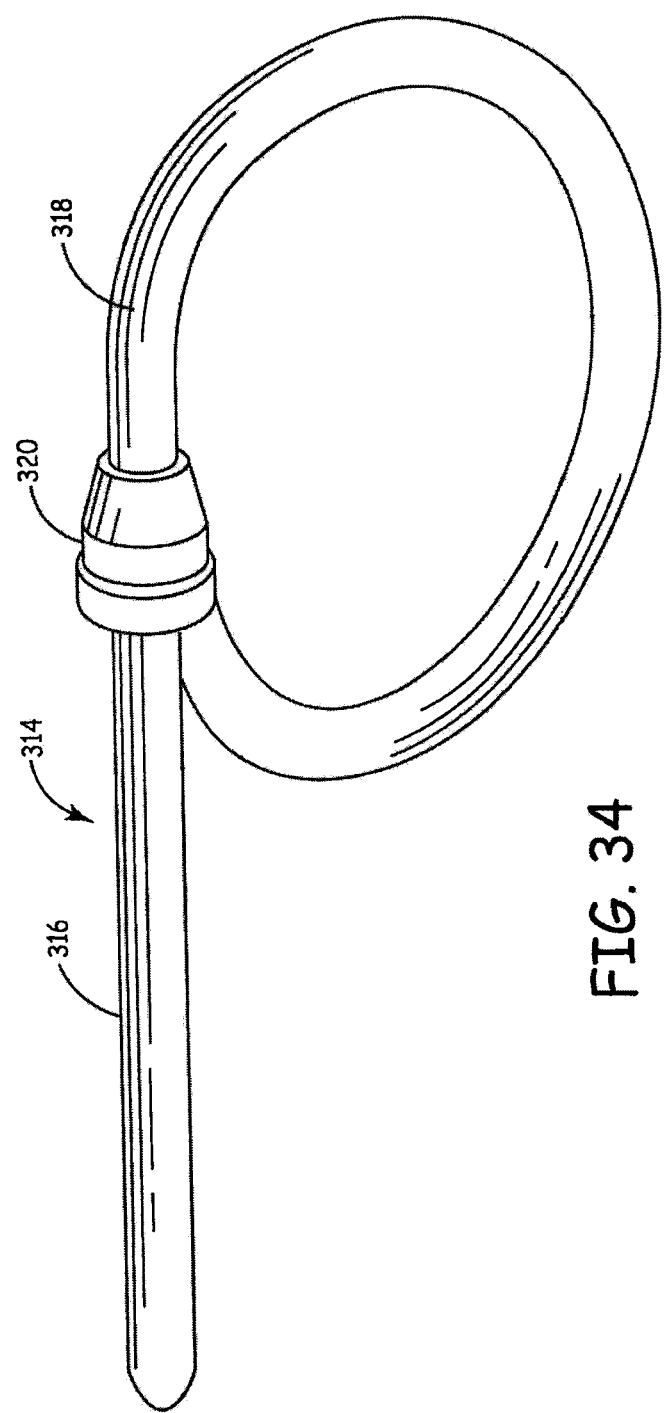
FIG. 34 is a perspective view of an adjustable band occluder according to one embodiment of the invention.

As shown in FIG. 34, some embodiments of the invention provide an adjustable band occluder 314. The adjustable band occluder 314 can include a band 316, a loop 318, and an adjustment mechanism 320. The size of the loop 318 can be varied by moving the adjustment mechanism 320 along the length of the band 316. The adjustable band occluder can be locked in a fixed position by any suitable means, such as, but not limited to, a crimper region, a ratchet mechanism or other mechanical engagement structure, or other suitable locking mechanism.

FIG. 34A is a perspective view of an adjustable band occluder 314A and a device 314B for implanting the adjustable band occluder 314A.

FIG. 34B is an enlarged view of portions of the adjustable band occluder 314A and the device 314B of FIG. 34A with portions broken away to illustrate additional details.

Some embodiments of the invention address a number of problems, such as surgical access to the endocardial surfaces of the atrial chambers of a beating heart and permanent closure of the atrial appendage volume. These problems have been addressed by others using various methods and devices, such as percutaneous catheters. The right atrium may be accessed via transvenous catheters placed through a femoral vein in the groin, as well as through superior veins such as the subclavian, brachiocephalic, or jugular veins. The left atrium is more difficult to reach transvenously, requiring first, right atrial access followed by a transseptal puncture through the fosa ovalis of the inter-atrial septum into the left atrium. With these transvenous methods, only relatively small diameter catheters can be passed through the vasculature. In addition, these devices must be navigated using fluoroscopic guidance or some form of electronic navigation.

Positioning and placement of the therapeutic elements of such catheters can be a challenge, because the movement is controlled remotely from the point of venous access. From point of entry into the body to the therapeutic end of the catheter, the distance may be 70-110 cm through a difficult path. In cases where tissue contact force is critical, this can be a significant problem. Stability of the catheter tip is an issue in a beating heart compared to firm control possible with much shorter and more rigid surgical implements. A number of commercially-available catheters may be able to be positioned in most areas of the atria, but only one catheter-based device has been developed to permanently close off the left atrial appendage following a procedure. This device, known as PLAATO (percutaneous left atrial appendage total occlusion) must be carefully sized to allow positioning within the left atrial appendage such that it is retained in position distal to the ostium with the left atrial chamber. This presents a significant risk that the device may be released into the atrium and pass into the left ventricle and become entangled in the chordae tendinae supporting the mitral valve or become lodged in the left ventricular outflow tract or aorta. The risks of such a procedure were documented in an abstract by Fischer at the 2005 meeting of the American College of Cardiology—Evelyn Fischer, et al., "Left Atrial Appendage Occlusion to Prevent Stroke in Suboptimal Warfarin Candidates Current Results of the European Multicenter Registry Trial," American College of Cardiology, Abstract presented at 2005 National Meeting, which is herein incorporated by reference in its entirety.

The atria may be accessed through sternotomy, thoracotomy, intercostals ports, or under the sub-xiphoid process. Access to the atria is important for treatment of atrial fibrillation (AF), atrial-septal-defects (ASD's), patent foramen ovalis (PFO), and mitral or tricuspid valve disease. Also of importance is the elimination of the left atrial appendage volume at the end of the procedure in order to reduce stroke risk. Surgical removal and closure of the left atrial appendate has been accomplished by using a surgical stapler/ligation device or by suturing the appendage closed followed by surgical excision of the distal appendage. This is not without risks as noted by Krum et al.—David Krum, David L. Olson, Daniel Bloomgarden, Jasbir Sra, "Visualization of Remnants of the Left Atrial Appendage following Epicardial Surgical Removal," Heart Rhythm (2004) 1, 249. Such surgical removal may result in an incomplete reduction of the left atrial appendage and allow a volume to remain unclosed, which is herein incorporated by reference in its entirety.

Regarding the relationship between the left atrial appendage and stroke risk, Blackshear et al. stated that left atrial appendage obliteration "is a routine part of modern 'curative' operations for nonrheumatic atrial fibrillation, such as the maze and corridor procedures." Joseph L. Blackshear, MD, John A. Odell, FRCS (Ed), "Appendage Obliteration to Reduce Stroke in Cardiac Surgical Patients with Atrial Fibrillation," Ann. Thorac. Surg., 1996; 61:755-759, which is herein incorporated by reference in its entirety. To assess the potential of left atrial appendage obliteration to prevent stroke in nonrheumatic atrial fibrillation patients, they reviewed previous reports that identified the etiology of atrial fibrillation and evaluated the presence and location of left atrial thrombus by transesophageal echocardiography, autopsy, or operation.

They reviewed the results of twenty-three separate studies and found that 446 of 3,504 (13%) rheumatic atrial fibrillation patients, and 222 of 1,288 (17%) nonrheumatic atrial fibrillation patients had a documented left atrial thrombus. Anticoagulation status was variable and not controlled for. Thrombi were localized to, or were present in the left atrial appendage and extended into the left atrial cavity in 254 of 446 (57%) of patients with rheumatic atrial fibrillation. In contrast, 201 of 222 (91%) of nonrheumatic atrial fibrillation-related left atrial thrombi were isolated to, or originated in the left atrial appendage (p<0.0001). Their data suggested that left atrial appendage obliteration is a strategy of potential value for stroke prophylaxis in nonrheumatic atrial fibrillation. A device was developed that allows percutaneous left atrial appendage transcatheter occlusion (PLAATO) via transseptal catheterization. Initial studies in dogs demonstrated the ability of the device to seal the left atrial appendage. Sievert et al. reported their initial experience with PLAATO in a human clinical trial involving 15 patients. Horst Sievert, MD et al, "Percutaneous Left Atrial Appendage Transcatheter Occlusion to Prevent Stroke in High-Risk Patients with Atrial Fibrillation," Circulation, 2002, 105:1887, which is herein incorporated by reference in its entirety.

PLAATO was purported to be a less invasive, percutaneous approach to closing the left atrial appendage. Previous animal studies of the device with follow-up of up to 1 year have demonstrated occlusion of the left atrial appendage with complete healing, absence of erosions, new thrombus formation on the device, or interference with atrial function.

In the initial cohort of 15 patients, occlusion of the left atrial appendage was successful in all, as proven by left atrial angiography. There were no complications associated with the device, either acutely during the implantation procedure or during follow-up. The only complication during the study was hemopericardium in the first patient attempted, which was not device-related. It resulted from left atrial appendage access, and should be easily avoided with increased experience. The procedure was successful in a second attempt in that patient.

Figure 35:
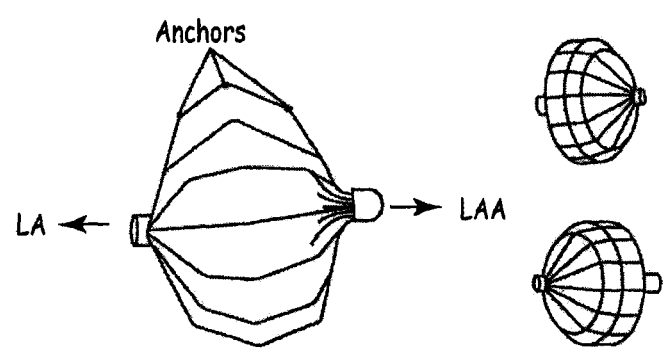
FIG. 35 is a perspective view of a deployed percutaneous left atrial appendage transcatheter occlusion (PLAATO) device.
Figure 36:
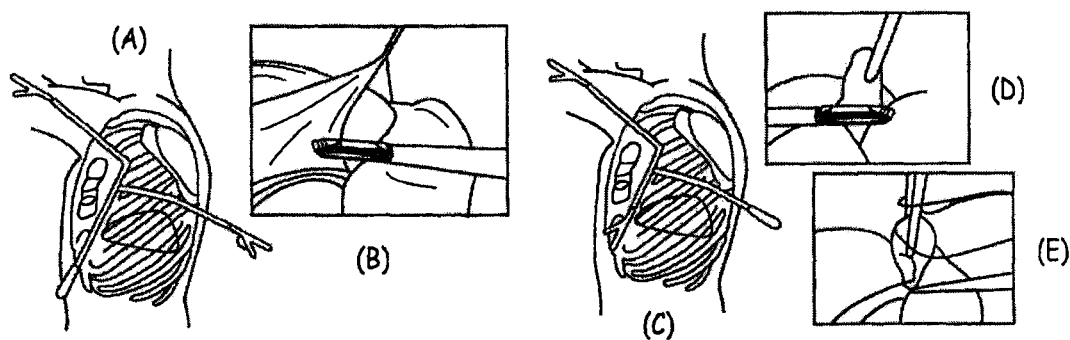
Figure 37:
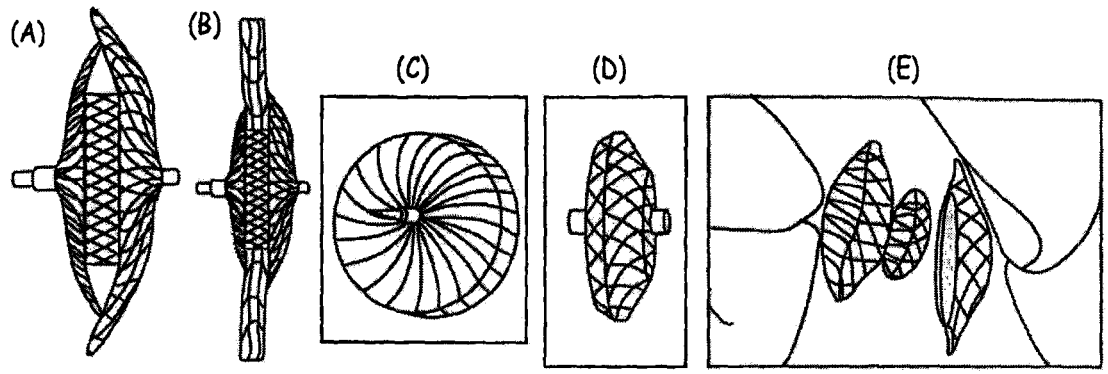

All patients did well in follow-up. One theoretical concern is the development of new thrombi on the implant. However, the use of ePTFE on the implant surface should result in relatively benign healing. Histological examination in dogs undergoing PLAATO reveal partial endothelialization at 1 month, which is complete by 2 to 3 months. In these 15 patients, transesophageal echo (TEE) at 1 month showed the surface to be completely smooth and free of mobile thrombi. FIG. 35 illustrates a deployed PLAATO device.

Fluoroscopic images of non-occluded left atrial appendage, deployment of the PLAATO device, and left atrial appendage post-deployment can be taken.

A larger cohort of patients was included in the European PLAATO Registry Trial by Fischer, et al. a study that was finished in January 2003 that examined the safety and feasibility of this procedure. This study described the experience of 92 patients. Inclusion criteria were atrial fibrillation (AF) with inability to take Warfarin®, prior cerebral ischemia and/or two clinical risk factors for stroke. After implantation of the PLAATO occluder, the patients were followed with X-ray, TEE and NIH stroke scale in regular intervals. Of the 92 patients, 67% were male with a mean age of 70±9 years. All candidates were successfully implanted. The mean procedure time was 76±36 minutes and the mean left atrial appendage orifice diameter was 20±3 mm. During follow up, one patient died of a bronchial carcinoma diagnosed 3 months before the one year follow up. One patient sustained a stroke six months post implant. Thus, the yearly incidence of stroke after implantation is 1.9%. With this small number of patients, the estimated risk reduction was 55%.

Of concern, in three patients, a thrombus on the occluder was found prior to hospital discharge (2) and one month after the procedure (1). All thrombi were resolved without sequelae. One device was chosen too small and embolized into the aorta after its release. It was snared with a catheter and was retrieved successfully. Another device was implanted successfully in the very same procedure.

To summarize this group's experience with the PLAATO device, the incidence of stroke in high-risk patients may decrease after implantation of the device. Considerable risks exist with this procedure, including errant transseptal puncture resulting in aortic dissection or atrial free wall perforation resulting in tamponade, embolization of the PLAATO device resulting in device entanglement in cardiac structures, along with thrombus formation on the occluder surface that could lead to emboli production and stroke. In addition, the chronic nature of this implant must be considered. Constant flexure of the nitinol wire structure may lead to long term fatigue and potential fracture and perforation of cardiac or adjoining tissues.

The group of Odell et al, hypothesized that if the atrial appendage could be safely obliterated, then the incidence of embolic stroke may be lessened. John A. Odell, et al., "Thoracoscopic Obliteration of the Left Atrial Appendage: Potential for Stroke Reduction," Ann. Thorac. Surg., 1996, 61:565-569, which is herein incorporated by reference in its entirety. If the appendage can be obliterated using a thoracoscopic technique, a procedure of lesser magnitude than thoracotomy, then it may offer an alternative form of management for patients ineligible for Warfarin®therapy. To determine the feasibility of atrial appendage obliteration done using the thoracoscope, they performed the procedure in mongrel dogs and in human cadavers.

Transesophageal echocardiography with emphasis on visualization of the left atrial appendage was performed pre-, intra-, and postoperatively. In five dogs, the atrial appendage was obliterated with staples, and in five the appendage was obliterated with an endoloop of 0 Vicryl suture material. Three ports were made—one in approximately the seventh interspace approximately 5 cm from the midsternum (port 1), a second inserted anteriorly in the fourth interspace (port 2), and a third more posteriorly in the fourth interspace (port 3). Carbon dioxide was instilled to a pressure of 4 to 10 mm to collapse the lung. In all animals, the pericardium was opened anterior and parallel to the phrenic nerve. Gordon N. Olinger, MD, "Carbon dioxide displacement of left heart chambers," J. Thorac. Cardiovasc. Surg., 1995, 109:187-188, which is herein incorporated by reference in its entirety.

Through the first port, the camera was inserted; through the second port, the pericardium was grasped with an instrument; and, using scissors inserted through the third port, the pericardium was opened. The technique then varied depending upon whether the appendage was obliterated with staples or with the endoloop. In those having the appendage stapled, the camera was withdrawn from port 1 and inserted in port 3. Through port 1, a 35 endo GIA stapler (Ethicon Endosurgery, Cincinnati, Ohio) with the knife blade removed was inserted, positioned across the base of the atrial appendage, and fired. In dogs having the appendage obliterated with the endoloop (Ethicon), the camera position was not changed. The endoloop was introduced through port 3 and the appendage was grasped through the loop of the suture. The loop was positioned across the base of the appendage and then tightened.

At 11 weeks, the dogs were again anesthetized with sodium pentobarbital (30 mg/kg intravenously) and a midline sternotomy was made. The heart was examined using epicardial echocardiography. The dogs were euthanized, the hearts were removed, and the left atrium was inspected.

The procedure also was attempted in eight human cadavers. In the cadavers, three ports were used for access. The most appropriate sites appeared to be the second interspace anteriorly in the midclavicular line (for grasping the pericardium and the atrial appendage), the sixth interspace in the midclavicular line (for the camera or stapling instrument), and the fifth interspace in the anterior axillary line (usually for the scissors to open the pericardium, but also for the camera or for the stapling instrument). The procedure as performed in the dog and human experiments is illustrated in FIGS. 36A-E.

The group of DiSesa investigated the use of an automatic surgical stapler for ligation of the atrial appendage in sheep, and then applied this technique in patients. V. J. DiSesa, S. Tam and L. H. Cohn, "Ligation of the Left Atrial Appendage using an Automatic Surgical Stapler," The Annals of Thoracic Surgery, Vol. 46, 652-653, which is herein incorporated by reference in its entirety. Fourteen adult sheep underwent ligation of the left atrial appendage using a surgical stapler with a rotating head and either absorbable or stainless steel staples. In four sheep, killed after two hours, no hemorrhage or intra-atrial thrombus was observed acutely. Ten sheep were allowed to recover for 90 to 100 days, twice the expected absorption time of absorbable staples. There was complete obliteration of the left atrial appendage without evidence of intra-atrial thrombus or staple migration. The absorbable staples were completely reabsorbed. They subsequently used this technique in five patients undergoing mitral valve procedures. There were no complications, and adequate obliteration of the atrial appendage was achieved. Other reports indicate that staples may require the use of reinforcement strips to prevent bleeding and tissue tearing.

Considering the simple surgical ligation methods, the group of Katz, et al. studied the incidence of incomplete ligation of the left atrial appendage during mitral valve surgery. Edward S. Katz MD, FACC, Theofanis Tsiamtsiouris MD, Robert M. Applebaum MD, FACC, Arthur Schwartzbard MD, FACC, Paul A. Tunick MD, FACC and Itzhak Kronzon MD, FACC, "Surgical Left Atrial Appendage Ligation is Frequently Incomplete: A Transesophageal Echocardiographic Study," Journal of the American College of Cardiology, Volume 36, Issue 2, 1 Aug. 2000, Pages 468-471, which is herein incorporated by reference in its entirety. Using transesophageal Doppler echocardiography, they studied 50 patients who underwent mitral valve surgery and ligation of the left atrial appendage. Incomplete left atrial appendage ligation was detected in 18 of 50 (36%) patients. This study demonstrated that surgical left atrial appendage ligation is frequently incomplete. Residual communication between the incompletely ligated appendage and the left atrial body may produce a milieu of stagnant blood flow within the appendage and be a potential mechanism for embolic events. Ligation of the left atrial appendage is frequently performed during mitral valve surgery to eliminate a potential source of emboli. However, the success of completely excluding the left atrial appendage from the circulation had not previously been systematically addressed. Transesophageal echocardiography offers unique visualization of the appendage in the beating heart and can evaluate the integrity of the surgical ligation. Usually, when the left atrial appendage is ligated, its cavity is obliterated with clot (since no flow enters the cavity) and cannot be seen during echocardiography. This appearance was the same whether the patient was studied in the operating room or months after the surgery. When the appendage is incompletely ligated, not only can the appendage cavity be visualized but flow can be seen within the appendage, as well as through an opening in the ligation site.

The group discovered that 36% of the time the left atrial appendage was found to be incompletely ligated after attempts at excluding it from the left atrial body. Factors, such as an enlarged left atrium or significant mitral regurgitation, which may be thought to increase left atrial tension and pressure (perhaps predisposing to incomplete ligation or dehiscence of sutures), did not appear to correlate with this finding. They also did not observe a correlation between appendage size and the incidence of incomplete ligation. In addition, the surgical procedure (mitral repair or replacement) and operative approach (traditional sternotomy or minimally invasive approach) did not change the incidence of incomplete ligation. It is possible, however, that the sample size in this report may have been too small to exclude a significant effect of these variables on the development of incomplete left atrial ligation.

Incomplete left atrial appendage ligation was as commonly seen in the operating room, evaluating the patient by transesophageal echocardiography immediately after terminating cardiopulmonary bypass, as it was seen in the laboratory evaluating patients referred for transesophageal echocardiography at various times after the surgery. This suggested that incomplete left atrial appendage ligation is not a degenerative process with suture dehiscence over time, but rather is present immediately after the initial surgery. Incomplete ligation may be secondary to several surgical factors. First, the running sutures used may not start and end exactly at the most distal edges of the atrial appendage, which may not be recognized with the appendage empty and unstretched while on cardiopulmonary bypass during surgery. In addition, caution must be taken during appendage ligation to avoid deep suture bites, which may involve the left circumflex coronary artery or its branches that may course in the area. This meticulous care may lead to shallower suture bites that may dehisce when the LA is once again filled and stretched after cardiopulmonary bypass. Both of these mechanisms may play a role, as in many cases flow was detected both at the edge of the appendage orifice (apparently around the end of the suturing line) and through an area at the midpoint of the appendage orifice (through the suture line). One group reported six cases of incomplete left atrial appendage ligation when a purse string suture was used to accomplish the ligation, a technique different from that used by surgeons. The actual incidence, however, of incomplete left atrial appendage ligation using their technique was not addressed.

The clinical significance of an incompletely ligated left atrial appendage has never been studied. Theoretically, creating a small communication between the LA and left atrial appendage may produce stagnation of low velocity blood flow within the atrial appendage. The appendage would then be a model for thrombus formation and continue to serve as a potential source of embolization since a port of entry into the systemic circulation still exists. Although the numbers in this study were small, several observations support this theory. First, spontaneous echo contrast (a marker for stagnant blood flow and a precursor of thrombus formation) was seen within the appendage in half of the patients with incomplete ligation. Second, and perhaps more importantly, in two-thirds of patients with spontaneous echo contrast within the incompletely ligated appendage, the contrast was actually denser within the appendage than within the left atrial body, suggesting a more stagnant and thrombogenic milieu. In two patients, frank thrombus was seen within the incompletely ligated appendage.

The ultimate question, however, is whether patients with incompletely ligated left atrial appendages will have a higher incidence of thromboembolic events. In the Katz study, four patients with incompletely ligated appendages had such events (one patient with Starr-Edwards prosthesis, two with St. Jude prosthesis and one patient status after mitral repair). This is quite a high number considering that only eight patients with incomplete ligation had any potential for long term follow-up (the other ten patients with incomplete ligation were discovered in the operating room). However, one cannot exclude other etiologies for embolization (as mechanical prostheses or atrial fibrillation) and referral bias still clouds this issue. Certainly, conventional ligation methods must be questioned in light of the findings of this study.

A number of devices for occlusion of ASD's have been investigated. Melhem J. A. Sharafuddin, MD; Xiaoping Gu, MD; Jack L. Titus, MD, PhD; Myra Urness, BS; J. J. Cervera-Ceballos, MD; Kurt Amplatz, MD, "Preliminary Results With a New Self-Expanding Nitinol Prosthesis in a Swine Model Transvenous Closure of Secundum Atrial Septal Defects," Circulation, 1997, 95:2162-2168, which is herein incorporated by reference in its entirety. Most of these concepts involve percutaneous delivery from femoral vein access. Varying levels of success have been achieved. Device dislodgment can occur if the size of the defect greatly exceeds the waist diameter of the device or approaches the diameter of the retention buttons. On the other hand, placement of a disproportionately large device may result in mushrooming of the retention buttons and weakening of the cross-clamping forces against the septal rim, which increases the risk of blood flow behind the discs and may result in incomplete endothelialization. In addition, follow-up studies of a clamshell occlusion device reported a delayed rate of metal fatigue fractures of one or more arms of about 30%. The Amplatzer device is shown in FIGS. 37A-E.

A small introduction system, simple and reliable placement technique, and favorable initial experimental success may provide promising potential of such a device for the percutaneous closure of secundum ASDs in all age groups. Heparinization is advocated in clinical use to lower the risk of catastrophic systemic embolization.

ASD device thrombosis is likely to be similar to thrombosis to be expected on left atrial appendage closure devices.

This makes the study by Krumsdorf et al, on the incidence, morphology, and clinical course of thrombus formation after catheter closure of ASD closure devices of interest regarding devices such as PLAATO. Krumsdorf U, Ostermayer S, Billinger K, Trepels T, Zadan E, Horvath K, Sievert H, "Incidence and Clinical Course of Thrombus Formation on Atrial Septal Defect and Patient Foramen Ovale Closure Devices in 1,000 Consecutive Patients," J. Am. Coll. Cardio., Jan. 21, 2004. 43(2):302-9, which is herein incorporated by reference in its entirety.

A total of 1,000 consecutive patients were investigated after patent foramen ovale (PFO) (n=593) or atrial septal defect (ASD) (n=407) closure. Transesophageal echocardiography (TEE) was scheduled after four weeks and six months. Additional TEEs were performed as clinically indicated. Thrombus formation in the left atrium (n=11), right atrium (n=6), or both (n=3) was found in 5 of the 407 (1.2%) ASD patients and in 15 of the 593 (2.5%) PFO patients (p=NS). The thrombus was diagnosed in 14 of 20 patients after four weeks and in 6 of 20 patients later on. The incidence was: 7.1% in the CardioSEAL device (NMT Medical, Boston, Mass.); 5.7% in the StarFLEX device (NMT Medical); 6.6% in the PFO-Star device (Applied Biometrics Inc., Burnsville, Minn.); 3.6% in the ASDOS device (Dr. Ing, Osypka Corp., Grenzach-Wyhlen, Germany); 0.8% in the Helex device (W.L. Gore and Associates, Flagstaff, Ariz.); and 0% in the Amplatzer device (AGA Medical Corp., Golden Valley, Minn.). The difference between the Amplatzer device on one hand and the CardioSEAL device, the StarFLEX device, and the PFO-Star device on the other hand was significant (p<0.05). For a device such as PLAATO, specifically designed to reduce or eliminate thromboembolic events coming from the region of the implant, occurrence of thrombus on ASD devices is a concern.

A method and apparatus for thoracoscopic intracardiac procedures was described U.S. Pat. No. 6,401,720, entitled "Method and Apparatus for Thoracoscopic Intracardiac Procedures," Stevens, John H.; Palo Alto, Calif. 94303, Reitz, Bruce A.; Stanford, Calif. 94305, Roth, Alex T.; Redwood City, Calif. 94061, Peters, William S.; Woodside, Calif. 94062, Gifford, Hanson S.; Woodside, Calif. 94062, which is herein incorporated by reference in its entirety. They described devices, systems, and methods provided for accessing the interior of the heart and performing procedures therein while the heart is beating. In one embodiment, a tubular access device having an inner lumen is provided for positioning through a penetration in a muscular wall of the heart, the access device having a means for sealing within the penetration to inhibit leakage of blood through the penetration. The sealing means may comprise a balloon or flange on the access device, or a suture placed in the heart wall to gather the heart tissue against the access device. An obturator is removably positionable in the inner lumen of the access device, the obturator having a cutting means at its distal end for penetrating the muscular wall of the heart. The access device is preferably positioned through an intercostal space and through the muscular wall of the heart. Elongated instruments may be introduced through the tubular access device into an interior chamber of the heart to perform procedures, such as septal defect repair and electrophysiological mapping and ablation. A method of septal defect repair includes positioning a tubular access device percutaneously through an intercostal space and through a penetration in a muscular wall of the heart, passing one or more instruments through an inner lumen of the tubular access device into an interior chamber of the heart, and using the instruments to close the septal defect. Devices and methods for closing the septal defect with either sutures or with patch-type devices are disclosed. While this concept allows access to the heart chambers similar to the present invention, it does not provide for a simple means of incisional closure as do some embodiments of the invention.

Some embodiments of the invention may provide any one or more of the following advantages: a single point of access for surgical treatment of atrial fibrillation; fewer inter-costal access ports may be needed for treating atrial fibrillation, as opposed to existing minimally-invasive methods; blunt dissection of cardiac tissue is generally not required; pericardium is left substantially intact, except for a small incision; access to the heart for delivery of therapies for various disease states; a single device can provide surgical access to the heart chambers, as well as providing a means of closing the point of access at the end of the procedure; and the left atrial appendage can be ligated and/or eliminated at the close of the procedure with little or no risk of tearing. The left atrial appendage can be eliminated at the close of the procedure such that a residual remaining volume which could lead to strokes is avoided.

Some embodiments of the invention provide a device that can provide access to the interior of the heart chambers. The device can allow for single point access to treat atrial fibrillation, atrial-septal defects, patent foramen ovalis, and valvular disease, as well as other arrhythmias. Some embodiments of the device can be used to access the ventricles from the access achieved through either appendage. Ventricular septal defects can be addressed. The device can be applied to other body structures, such as the stomach where a portion of the stomach wall could be ligated by the elastic band and excluded. This may be suitable as a treatment for obesity.

Some embodiments of the invention provide methods and devices to allow entry into the atria of a beating heart to perform delivery of therapy to the structures within the heart and endocardial surfaces and valves associated with the heart chambers. Upon removal of the device from the appendage, a permanent closure and elimination of the appendage volume can be affected. More specifically, the entry points can be located in the left and right atrial appendages. Of these, the left atrial appendage may be most appropriate, because closure and elimination of this appendage following a procedure has become a standard surgical practice performed by many surgeons.

According to embodiments of the method of the invention, pre-procedure includes placement of one or two chest wall access ports for visualization and placement of the invention. The lung can be deflated and a small opening in the pericardium can be made adjacent to the left atrial appendage. FIG. 38 schematically illustrates the relative locations of structures of the heart and chest of interest regarding the invention. More specifically, the left atrial appendage is shown in a stretched state without the pericardium in place. The heart structures noted on FIG. 38 include the following: SVC—superior vena cava, IVC—inferior vena cava, TV—tricuspid valve, FO—fossa ovalis, MV—mitral valve, PV—pulmonary vein, and left atrial appendage—left atrial appendage. FIGS. 39-68 illustrate devices and methods of using the devices according to various embodiments of the invention. In some embodiments, a device 400 can include an elastic cinch ring 410, ring expansion arms 412, and a portal tube assembly 414. The ring expansion or cinch ring support arms 412 can include three or four arms. The device 400 can be positioned through a chest port 416 in a portion of the chest wall 418. The device 400 can be passed through a chest port 416 placed between the ribs. The anatomical drawings of FIGS. 39-57 have been simplified to show only the left atrial appendage and the chest wall.

FIG. 39 illustrates the elastic cinch ring 410 in a contracted state. FIG. 40 illustrates the device 400 being advanced toward the left atrial appendage. FIG. 41 illustrates a suction cup or Babcock grasper probe 420 being advanced through the portal tube assembly 414.

FIG. 42 illustrates the suction cup or Babcock grasper probe 420 being attached to an end of the left atrial appendage. In other embodiments, any suitable type of grasper, vacuum device, adhesive, cyrogenic device, or nanotechnology device can be used to grasp and pull the left atrial appendage. FIG. 43 illustrates the support arms 412 being expanded and the left atrial appendage being pulled toward the portal tube assembly 414. FIG. 44 illustrates the cinch ring 410 being advanced over the left atrial appendage. FIG. 45 illustrates the cinch ring 410 being positioned over the mid to proximal left atrial appendage.

FIG. 46 illustrates the cinch ring 410 being allowed to contract over left atrial appendage and occlude a lumen 422 of the left atrial appendage. FIG. 47 illustrates the suction cup or Babcock grasper probe 420 removed from portal tube assembly 414. FIG. 48 illustrates a dilator/sheath assembly 424 including a dilator 426 and a sheath 428 being advanced through the portal tube assembly 414. In some embodiments, prior to puncturing into the atrial appendage, the thoracic cavity can be inflated with carbon dioxide gas. Carbon dioxide inflation of the pericardial space can be used to lessen the prevalence and consequences of air embolism, can help limit the chances of air introduction, and can help limit bleeding. FIG. 49 illustrates a needle or sharp wire 430 being advanced through a lumen of the dilator 426 to puncture into the left atrial appendage lumen 422.

FIG. 50 illustrates the dilator 426 being advanced into the lumen 422 of the left atrial appendage and the needle 430 retracted. FIG. 50 illustrates the sheath 428 being advanced over the dilator 426 into the left atrial appendage lumen 422. FIG. 51 illustrates the left atrial appendage being filled with heparinized saline, as blood and air are removed. As shown in FIG. 52, the left atrial appendage lumen 422 can be aspirated of blood 432 and flushed with heparinized saline using a syringe 434 to prevent thrombus formation. As shown in FIG. 53, the left atrial appendage lumen 422 can be filled with heparinized saline as blood and air are removed. However, in some embodiments, it may be desirable to allow blood to form a thrombus in the remaining left atrial appendage volume to promote healing and absorption of the closed-off portion of the left atrial appendage by surrounding tissue.

As shown in FIG. 54, the dilator 426 can be advanced past the cinch ring 410 and into the left atrium. As shown in FIG. 55, the sheath 428 can be advanced over the dilator 426 past the cinch ring 410 and into the left atrium. As shown in FIG. 56, the dilator 426 can be removed. A hemostasis valve (not shown) can be positioned on a proximal end of the sheath. As shown in FIG. 57, therapeutic implements can be advanced into the left atrium for the treatment of various conditions.

FIG. 58 illustrates one embodiment of a balloon ablation device 436 positioned at the right inferior pulmonary vein ostium. The use of a cryogenic or high-intensity focused ultrasound balloon ablation device can be used in some embodiments of the invention. FIG. 59 illustrates one embodiment of a balloon ablation device 436 positioned at the left superior pulmonary vein ostium.

FIG. 60 illustrates one embodiment of an encircling ablation device 438 approaching the left superior pulmonary vein ostium. The ablation device 438 can use radiofrequency (RF) energy, cryothermy, high-intensity focused ultrasound, microwaves, or any other suitable ablation energy. FIG. 61 illustrates one embodiment of an encircling ablation device 438 placed around the left superior pulmonary vein ostium.

FIG. 62 illustrates one embodiment of a left atrial debulking spiral ablation device 440 placed against the posterior left atrium. FIG. 63 illustrates one embodiment of a high intensity focused ultrasound ablation device 442 that can create a lesion over the left atrial isthmus. FIG. 64 illustrates one embodiment of a PFO or ASD closure device 444 being deployed in the fossa ovalis of the inter-atrial septum. FIG. 65 illustrates one embodiment of a linear ablation device 446 forming connecting lesions between the pulmonary veins.

As shown in FIG. 66, at the completion of all the endocardial therapeutic procedures, the elastic cinch ring 410 can be allowed to constrict down around the base of the left atrial appendage. The sutures or other devices holding the cinch ring 410 can be released such that the support arms 412 and the portal tube assembly 414 can be pulled away from the heart, while leaving the cinch ring 410 substantially permanently in place at the base of the appendage. As shown in FIG. 67, immediately following the procedure, the left atrial appendage will generally include a volume that is contained by the cinch ring 410. Healing will then occur and the vestige of the left atrial appendage will be absorbed into the atrial wall. As shown in FIG. 68, after approximately 12 weeks, the left atrial appendage is expected to have been absorbed and assimilated by the atrial wall. The ring 410 can remain embedded in the remaining scar 448.

FIGS. 69-71 illustrate a device 500 for ligation of an atrial appendage. The device 500 can include a ring applicator or delivery tool 502 and an occlusion member or ring 514. In one embodiment, the occlusion ring 514 can be made of a 30 A durometer silicone rubber, although other hardnesses of silicone or other materials, such as polyurethane can be used. The ring 514 can be covered with a material such as Dacron® polyester to promote tissue ingrowth or prevent ring slippage after placement or to spread the load bearing surfaces of the ring. The ring 514 can be generally expandable for placement around the atrial appendage. The delivery tool 502 can be used to expand the ring 514. The delivery tool 502 can include a shaft 520 and a handle 530 coupled to shaft 520. The delivery tool 502 can be sized for reaching an atrial appendage through an opening in the patient's chest, for example, through a sternotomy or thoracotomy. The delivery tool 502 can include a tissue-grasping tool channel 570 extending from the handle 530 to the distal end of the shaft 520. A tissue-grasping tool 580 may be movably positioned within tissue-grasping tool channel 570. For example, shaft 584 of tissue-grasping tool 580 fits within tool channel 570. In one embodiment, tissue-grasping tool 580 may include one or more hooks, barbs, suction ports and/or graspers. For example, as shown in FIGS. 72 and 73, tissue grasping tool 580 may include tissue graspers 582. The tissue-grasping tool 580 can be used to grasp the atrial appendage and pull it through ring 514. In one embodiment, the tissue-grasping tool 580 can be moved distally and/or proximally relative to shaft 520.

In one embodiment, the delivery tool 502 can include a ring spreader 540 having a pair of ring-expanding members 542 used to hold and expand the ring 514. The ring spreader 540 can be coupled to a distal end of shaft 520. The ring 514 can be releasably coupled or attached to the distal ends of ring-expanding members 542 and the distal end of shaft 520, for example, via one or more sutures 550. The sutures 550 can loop around the ring 514. The ends of the sutures 550 can pass through one or more lumens within the ring expanding members 542, the shaft 520, and the handle 530. In one embodiment, the two ring-expanding members 542 open ring 514 into a triangular shape. The proximal ends of the ring-expanding members 542 are pivotally coupled to the distal end of shaft 520, thereby allowing the ring-expanding members 542 to pivot from a closed or collapsed position, as shown in FIG. 69, to an open or extended position, as shown in FIG. 70. In the collapsed position, ring-expanding members 542 run parallel to shaft 520 and the distal ends of the ring-expanding members 542 point in a direction towards handle 530. In the extended position, ring-members 542 are aligned perpendicular to each other and to shaft 520. In the extended position, ring 514 has an open triangular configuration, as shown in FIG. 70. In one embodiment, sutures 550 are used to control the opening and closing of ring-expanding members 542. Sutures 550 run through suture lumens 525 of shaft 520. The proximal ends of sutures 550 are attached or coupled to suture tension knob or ring expansion mechanism 532 located at handle 530. Suture tension knob 532 is rotatable and may include a ratcheting mechanism. The ratcheting mechanism may be used to keep tension on the sutures without having to continuously hold onto knob 532. As knob 532 is rotated, sutures 550 stretch ring 514 toward the distal ends of ring-expanding members 542 and actuate ring-expanding members 542 to move from a collapsed configuration to an extended configuration wherein ring 514 is opened into a triangular configuration. Ring 514 may be released when desired, for example, around tissue via actuation of suture cutting mechanism 562. Suture cutting mechanism 562 is used to cut sutures 550, thereby releasing ring 514 from delivery tool 502 remotely. Suture cutting mechanism 562 includes cutting blade 564, which is used to cut sutures 550.

In one embodiment, shaft 520 is approximately 12 mm in diameter and tool channel 570 is approximately 5.5 mm in diameter. In one embodiment, tool channel 570 provides guidance for positioning and manipulating tissue-grasping tool 580. In addition, tool channel 570 allows deliver tool 502 and tissue-grasping tool 580 to be positioned together through a single port, for example, a 12 mm port placed between the patient's ribs and it allows the two tools to be held by one hand.

In one embodiment of the present invention, the distal end of delivery tool 502 may be passed through a port or small incision, for example, in the chest of a patient and positioned adjacent the left atrial appendage of a heart. Next, knob 532 may be rotated, thereby opening ring 514. A tissue-grasping tool 580 may then be slid distally along tissue-grasping tool channel 570 so that graspers 582 protrude through ring 514. Graspers 582 may then be manipulated by handle 586 to grasp tissue of the left atrial appendage. Tissue-grasping tool 580 and delivery tool 502 are then manipulated so as to position a desired portion of the left atrial appendage within the triangular opening of ring 514. Ring 514 is then released from delivery tool 502 and allowed to constrict tissue of the left atrium.

The ring or band occluders and the clip occluders disclosed herein can be constructed of any one or more of the following materials: silicone rubber, polyurethane, super-elastic material, shape-memory polymer or metal, latex, nitrile, butyl, styrene-butadiene, polyacrylate, acrylic, polyisoprene, chloroprene, fluoroelastomers, or other suitable biocompatible elastomeric materials. The ring or band occluders and the clip occluders disclosed herein can incorporate any one or more of the following features: texturing to aid in mechanical stability (i.e., ridges, bumps, grooves, etc.); fabric such as Polyethyleneterapthalate (i.e., Dacron®), polyester, ePTFE, etc. to promote tissue ingrowth; other types of coatings to promote tissue ingrowth; and pharmacological agents (e.g. a controlled release agent) to aid in tissue ingrowth, local therapeutic apoptosis, local necrosis, revascularization, arrhythmia control, infection control, anti-bacterial, fluid balance (i.e., atrial natritic peptide replacement).

In some embodiments of the invention, the ring or band occluders and/or clip occluders may incorporate one or more pharmacological agents including anti-inflammatory agents (e.g., steroids, dexamethasone, beclomethasone) anti-arrhythmic agents, chemotherapeutic agents, anti-infection agents, anticoagulant agents, anti-thrombotic agents (e.g., coumadin, heparin), clotting agents, platelet agents, cytotoxic agents, growth factors, angiogenesis factors, hormones (e.g., atrial natriuretic peptide), nitric oxide, radioactive agents, radiopaque agents (e.g., barium sulfate), echogenic agents (e.g., perfluorocarbon), antibodies, antigens, immunoglobulins, enzymes, neurotransmitters, cytokines, blood agents, regulatory agents, transport agents, fibrous agents, proteins, peptides, proteoglycans, toxins, antibiotic agents, antibacterial agents, antimicrobial agents, bacterial agents, hyaluronic acid, polysaccharides, carbohydrates, fatty acids, catalysts, vitamins, DNA segments, RNA segments, nucleic acids, lectin, antiviral agents, viral agents, genetic agents, ligands, drugs and dyes (e.g., which act as biological ligands). One or more drugs or gents may be found in nature (naturally occurring) and/or may be chemically synthesized.

One or more drugs or agents may be incorporated into the ring, band or clip, e.g., within a polymeric material of the ring, band or clip. One or more drugs or agents may be incorporated into one or more coatings of the ring, band or clip, e.g., within a polymeric coating covering at least a portion of the ring, band or clip. One or more drugs or agents may be incorporated into one or more fabrics of the ring, band or clip, e.g., within or on a fabric coating covering at least a portion of the ring, band or clip. In some embodiments of the invention, one or more drugs or agents may be loaded uniformly throughout one or more materials of the ring, band or clip. In some embodiments of the invention, one or more drugs or agents may be loaded non-uniformly in one or more materials of the ring, band or clip. In some embodiments of the invention, one or more drugs or agents may be loaded within an inner circumference of the ring, band or clip. In some embodiments of the invention, one or more drugs or agents may be loaded within an outer circumference of the ring, band or clip.

In some embodiments of the invention, one or more materials incorporated into the ring, band or clip may be "smart materials" which may alter their structure in response to one or more external factors, e.g., temperature. For example, the application of heat may cause a material, e.g., a polymer, to change shape or conformation, thereby resulting in the release of a drug or agent. In one embodiment, ultrasound, e.g., focused ultrasound, may be used to create heat needed to cause the material change shape or conformation.

In some embodiments of the invention, the ring, band or clip may comprise one or more radiopaque materials, e.g., barium sulfate, thereby making the ring, band or clip observable during fluoroscopic procedures. In some embodiments of the invention, the ring, band or clip may comprise one or more echogenic materials, e.g., perfluorocarbon, thereby making the ring, band or clip observable during ultrasound procedures.

In some embodiments of the invention, the ring, band or clip may release one or more drugs or agents via a diffusion-controlled mechanism. For example, a drug or agent may be uniformly or non-uniformly dispersed or dissolved in a material, e.g., a polymeric material, of the ring, band or clip and/or a coating of the ring, band or clip and/or a fabric covering of the ring, band or clip. The drug or agent may diffuse from an area of high concentration (e.g., from the material(s) of the band or clip) to an area of low concentration (e.g., an area of tissue such as the LAA).

In some embodiments of the invention, the ring, band or clip may release one or more drugs or agents via a biodegradable mechanism. For example, a drug or agent may be uniformly or non-uniformly dispersed or dissolved in a material, e.g., a polymeric material, of the ring, band or clip and/or a coating of the ring, band or clip and/or a fabric covering of the ring, band or clip. The drug or agent may be released during degradation of the material. The material may be designed to either degrade completely or to degrade partially, e.g., leaving the core structure of the material intact.

In some embodiments of the invention, the ring, band or clip may comprise a cross-sectional shape that may be round, square, rectangular, oval, triangular, star-shaped, etc. In some embodiments of the invention, the ring, band or clip may be reversibly placed, and its position may be adjusted if necessary. In some embodiments of the invention, multiple ring, band or clip may be placed more and more proximal to the base of the left atrial appendage.

In some embodiments of the invention, the ring, band or clip may include one or more sensors, for example to monitor changes in one or more tissue properties. One or more properties of surrounding tissue may change over time and/or in response to drug delivery, as described above, for example. In one embodiment, the band or clip may include a sensing electrode. Sensors may be monitored and/or controlled via wireless telemetry, for example, thereby providing wireless monitoring of one or more tissue properties over time.

In one embodiment, one or more sensors may comprise a biosensor, for example, comprising an immobilized biocatalyst, enzyme, immunoglobulin, bacterial, mammalian or plant tissue, cell and/or subcellular fraction of a cell. For example, the tip of a biosensor may comprise a mitochondrial fraction of a cell, thereby providing the sensor with a specific biocatalytic activity. In one embodiment, one or more sensors may be based on potentiometric technology or fiber optic technology. For example, a sensor may comprise a potentiometric or fiber optic transducer. An optical sensor may be based on either an absorbance or fluorescence measurement and may include an UV, a visible or an IR light source. In one embodiment, one or more sensors may be used to detect naturally detectable properties representative of one or more characteristics, e.g., chemical, physical or physiological, of a patient's bodily tissues or fluids. For example, naturally detectable properties of patient's bodily tissues or fluids may include pH, fluid flow, electrical current, impedance, temperature, pressure, components of metabolic processes, chemical concentrations, for example, the absence or presence of specific peptides, proteins, enzymes, gases, ions, etc. In one embodiment, one or more sensors may include one or more imaging systems, camera systems operating in UV, visible, or IR range; electrical sensors; voltage sensors; current sensors; piezoelectric sensors; electromagnetic interference (EMI) sensors; photographic plates, polymer-metal sensors; charge-coupled devices (CODs); photo diode arrays; chemical sensors, electrochemical sensors; pressure sensors, vibration sensors, sound wave sensors; magnetic sensors; UV light sensors; visible light sensors; IR light sensors; radiation sensors; flow sensors; temperature sensors; or any other appropriate or suitable sensor. In one embodiment, one or more sensors may be powered by a suitable power source. In addition, one or more sensors may be coupled to any appropriate output device, for example, a LCD or CRT monitor which receives and displays information regarding one or more sensors.

A temperature sensor may incorporate one or more temperature-sensing elements such as, for example, thermocouples, thermisters, temperature-sensing liquid crystals, or temperature-sensing chemicals. A temperature sensor could be used, for example, to monitor tissue temperature.

The signals from one or more sensor may be amplified by a suitable amplifier before reaching an output device. The amplifier also may be incorporated into an output device. Alternatively, the amplifier may be a separate device. The output device may incorporate one or more processors. In one embodiment, sensors may be positioned around a perimeter of the band or clip. When sensed tissue reaches a perimeter, a corresponding sensor may send a signal. In one embodiment, a sensor may send constant signals. For example, a sensor may send a constant signal based on its voltage. As a tissue perimeter changes, the voltage of the sensor may change proportionately and the signal sent by the sensor may change proportionately.

FIGS. 74 and 75 illustrate one embodiment of device 200 for ligation of an atrial appendage. In this embodiment, device 200 includes a ring applicator or delivery tool 202 and an occlusion member or ring 214. The delivery tool 202 can include a ring spreader 240 having ring-expanding members 242 used to hold and expand the ring 214. The ring spreader 240 can be coupled to a distal end of shaft 220. In one embodiment, the delivery tool 202 can include three ring-expanding members 242. As shown in FIG. 76, the ring 214 can be releasably coupled or attached to the distal end of ring-expanding members 242, for example, via wire hooks 272 made of stainless steel or nitinol, for example. The wire hooks 272 may be passed through one or more lumens 278 within ring-expanding members 242. The wire hooks 272 may be retracted partially (as shown in FIGS. 77 and 78) or completely into ring-expanding members 242 via a ring release mechanism 273 located at the proximal end of device 20, thereby releasing ring 214 from delivery tool 202. The handle 230 may also include a ring expansion mechanism 260 used to control the expansion of the ring 214. In one embodiment, ring expansion mechanism 260 is coupled to a wedge member 274 via a shaft 275. As the wedge member 274 is moved via ring expansion mechanism 260 from a distal position to a more proximal position the ring expanding members 242 are forced to move from a closed or collapsed configuration to an open or expanded configuration, as shown in FIGS. 74 and 75.

FIG. 79 illustrates one embodiment of device 200 for ligation of an atrial appendage. In this embodiment, device 200 includes a ring applicator or delivery tool 202 and an occlusion member or ring 214. The delivery tool 202 can include a ring spreader 240 having ring-expanding members 242 used to hold and expand the ring 214. The ring spreader 240 can be coupled to a distal end of shaft 220. In one embodiment, the delivery tool 202 can include three ring-expanding members 242 pivotally coupled to distal end of shaft 220, as shown in FIG. 80. As shown in FIG. 81, the ring 214 can be releasably coupled to the distal end of ring-expanding members 242, for example, via ring attachment members 252 pivotally coupled to ring expanding members 242. In one embodiment, ring attachment members 252 may be remotely controlled to pivot thereby releasing ring 214 from delivery tool 202. A ring release mechanism 273, coupled to ring attachment members 252, may be located at or near handle 230. Ring release mechanism 273 may be used to control the pivoting of ring attachment members 252 thereby releasing ring 214 from delivery tool 202. The handle 230 may also include a ring expansion mechanism 260 used to control the expansion of the ring 214. The ring expansion mechanism 260 may be coupled to the ring-expanding members 242. The ring expansion mechanism 260 can control movement of the ring expanding members 242 from a closed or collapsed configuration to an open or expanded configuration, as shown in FIGS. 79 and 80.

FIG. 82 illustrates one embodiment of device 34 for ligation of an atrial appendage, wherein ring applicator 34 includes a shaft 36 with a handle 38 on a proximal end and a ring spreader 40 on a distal end. In one embodiment, the ring spreader 40 includes a pair of spreader jaws 42 and 44. In one embodiment, a spring member may bias the jaws into an open or expanded configuration and/or a closed or collapsed configuration. In an alternative embodiment, the jaw arms 42 and 44 may ride on a cylinder 51 which forces the arms apart when they are pushed forward out the distal end of shaft 36. FIG. 83 shows one embodiment of ring spreader 40 in a closed or collapsed configuration. FIG. 84 shows one embodiment of ring spreader 40 in an open or expanded configuration. In one embodiment, a jaw actuator 48 is moveably coupled to handle 38. The jaw actuator 48 includes a shaft 49 connected to jaws 42 and 44. When the shaft 49 is pushed forward within the shaft 36, jaws 42 and 44 are forced out the distal end of shaft 36 and into an open or expanded configuration. In some embodiments, as shown in FIG. 9B, the ring 16 can be removably attached to the ring spreader 40 by one or more sutures, which may act as a retainer to hold the ring 16 in the ring spreader 40.

In some embodiments, the shaft of the ring, band or clip delivery tool may comprise one or more flexible, bendable and/or articulation section and/or sections. One or more flexible, bendable and/or articulation section and/or sections of the shaft of the delivery tool allows the device to accommodate a variety of patient anatomies via flexing, bending and/or articulation of the delivery tool's shaft. Preferably, any flexing, bending and/or articulation of the shaft will not inhibit the opening and closing mechanism of the delivery tool for opening and closing the ring, band or clip.

In one embodiment, as shown in FIG. 85, a portion of the shaft of the delivery tool may comprise an outer tube member 110 made of a memory alloy and/or plastic which may be pre-bent to a desired angle, for example 90°. The shaft may then comprise an inner stiffening rod member 111 placed within a lumen 112 of the outer tube member 110. The inner stiffening rod member 111 may be used to straighten the outer tube if advanced within the lumen 112 of the outer tube member 110 and allow the outer tube member 110 to return to its pre-bent shape if retracted. In one embodiment, the stiffening rod member 111 may be controlled by a rotating collar axially located with the outer tube member 110 and stiffening rod member 111. In one embodiment, the shaft or outer tube member 110 may include one or more lumens for control lines that facilitate the opening and closing mechanism or ring spreader of the delivery tool for opening and closing the ring, band or clip.

In one embodiment, as shown in FIGS. 86 and 87, a portion of the shaft of the delivery tool may comprise on or more hinge mechanisms 310, e.g., a hinge mechanism comprising multiple living hinges along a shaft section to create a gradual bend or curve for articulation. In one embodiment, one or more lumens 311 for control lines that facilitate the opening and closing mechanism or ring spreader of the delivery tool may be located as close to or through the pivots 312 of the hinges, thereby insuring that the control lines would not substantially lengthen or shorten throughout the range of hinge articulation. A cable or rod may be used, for example, to operate the hinge mechanism 310, thereby articulating the shaft portion comprising the living hinges, for example. One or more lumens 313 may be used for the cable or rod. The articulation of the hinge mechanism 310, e.g., the pushing and pulling of the cable or rod, may be controlled by a rotating collar axially located with the shaft. A gradual bend curve formed from the multiple living hinges prevents sharp bends or kinking in the opening and closing mechanism control lines, thereby insuring good working conditions for the opening and closing mechanism.

FIG. 88 illustrates one embodiment of device 300 for ligation of an atrial appendage, wherein ring applicator 300 includes a shaft 36 with a handle or hand piece 38 on a proximal end and a ring spreader 40 on a distal end. Shaft 36 may include an articulation section 320, for example, located at the distal portion of shaft 36, see FIG. 89. In one embodiment, articulation section 320 of shaft 36 may include one or more hinge mechanisms as shown in FIG. 90. In one embodiment, hinge mechanism 325 includes multiple living hinges controlled via a hinge articulation control wire 330. Moving control wire 330 in a proximal direction causes articulation section 320 to form a bend or curve. Moving control wire 330 in a distal direction causes articulation section 320 to straighten. In one embodiment, articulation control wire 330 is coupled to an articulation actuator or drive mechanism 335 positioned at the distal end of handle or hand piece 38. In one embodiment, as shown in FIGS. 91, 92 and 93, articulation drive mechanism 335 comprises an articulation drive screw 340 and an articulation drive screw knob 345 used to manually control the movement of control wire 330 in both a distal direction and a proximal direction. Rotation of drive screw knob 345 causes drive screw 340 to rotate, which, in turn, causes control wire 330 to move distally or proximally, thereby causing the hinged section 320 to bend or straighten.

In one embodiment, as shown in FIG. 90, ring spreader 40 includes a ring spreader drive wire 350 used to expand at least one embodiment of ring 14. For example, ring 14 may include a textile or fabric mesh covering 355 as shown in FIGS. 94 and 95. The fabric mesh covering 355 may cover the entire ring 14. Spreader drive wire 350 may run through a mesh covering lumen 357 as shown in FIG. 95. In one embodiment, the distal end of spreader drive wire 350 is fixed in place within mesh covering lumen 357 so that as drive wire 350 is pushed distally into mesh covering lumen 357 the mesh covering expands. Expansion of the mesh covering 355 forces ring 14 to expand. When drive wire 350 is pulled back proximally, the mesh and band contract back to a pre-expanded configuration. In one embodiment, the ring and mesh covering are expanded via drive wire 350 and they are positioned on the left atrial appendage as desired. Drive wire 350 may then be pulled proximally out of the mesh, thereby causing the ring and mesh covering to contract around the atrial appendage. In an alternative embodiment, the ring and mesh covering are expanded via drive wire 350 and they are positioned on the left atrial appendage as desired. Drive wire 350 may then be pulled proximally, thereby causing the ring and mesh covering to contract around the atrial appendage. The drive wire and mesh covering may then be removed completely from the ring, for example, via a suture or running stitch 356. The running stitch may be pulled out of the mesh covering thereby allowing the mesh covering to be removed from the ring. In one embodiment, as shown in FIG. 95, the running stitch may be located along the mesh covering and along the inside lumen of ring 14. In some embodiments, drive wire 350 may be releasably coupled to ring 14 via a mesh covering, one or more sutures, and/or one or more wires, for example.

In one embodiment, as shown in FIGS. 96 and 97, ring spreader drive wire 350 is coupled to a ring spreader actuator or drive mechanism 360 positioned at the proximal end of handle or hand piece 38. In one embodiment, ring spreader drive mechanism 360 comprises a hand trigger mechanism 365 used to manually control the movement of ring spreader drive wire 350 in both a distal direction and a proximal direction, thereby controlling the expansion and contraction of ring 14. As shown in FIG. 97, ring spreader drive mechanism 360 may also comprise a drive wire release assembly 370. Drive wire release assembly 370 allows the ring spreader drive wire 350 to be released from ring spreader drive mechanism 360. Drive wire release assembly 370 may comprise a spring 372. Spring 372 may be used to provide a desired amount of force or tension on drive wire 350. Drive wire release assembly 370 may comprise a drive wire release member 374. In one embodiment, drive wire release member 374 includes a release mechanism that is designed to release drive wire 350 when it is squeezed. In one embodiment, drive wire release assembly 370 includes locking pins 375, drive shaft members 376 and 377 and plunger 378 and plunger shaft 379. In one embodiment, as shown in FIGS. 98A, 98B and 98C, the drive wire release mechanism of drive wire release member 374 may comprise a coupler 380 coupled to drive wire 350 that when squeezed, opens a pair of jaws, which allows the user to pull the coupler free from the rest of the device.

Referring now to FIGS. 99-102, a system 600 for electrically connecting an electrical lead 602 inside a heart 604 (FIG. 102) of a patient and delivering an electrical signal to the heart 604 is illustrated according to various embodiments of the present disclosure. It will be appreciated that the system 600 can incorporate one or more components described above and illustrated in FIGS. 1-98C, and the method of using the system 600 can include one or more steps described above and illustrated in FIGS. 1-98C.

The system 600 can include a positioning tool 606. The positioning tool 606 can incorporate various features of any of the tools (e.g., occlusion tools, ring applicators, etc.) discussed above and illustrated in FIGS. 1-98C. Also, as will be discussed, the positioning tool 606 can be configured for placement of an electrical lead 602 in the heart 604 (FIG. 102).

The positioning tool 606 can also include a hollow tube 612 with a proximal end 608, a distal end 610, and a lumen 614 therein that extends longitudinally from the proximal end 608 to the distal end 610. The tube 612 can be flexible or rigid.

The positioning tool 606 can also include a ring spreader assembly 615 adjacent the distal end 610 of the tube 612. The ring spreader assembly 615 can include a plurality of arms 616a, 616b. The arms 616a, 616b can each be moveably coupled (e.g., hingeably coupled) at one end to the tube 612. Also, a resilient ring 618 can be releaseably coupled to the arms 616a, 616b. Thus, similar to the embodiments discussed above in relation to FIGS. 1-98C, movement of the arms 616a, 616b away from the tube 612 can resiliently stretch and expand the ring 618 (FIG. 99), and movement of the arms 616a, 616b toward the tube 612 can allow the ring 618 to resiliently recover and reduce in width (FIG. 100). It will be appreciated that the ring spreader assembly 615 and the ring 618 can be of any suitable type and can include any of the components described above in relation to FIGS. 1-98C. Also, the ring 618 can be a part that is included in the CARDIOBLATE CLOSURE™ system, which is available for clinical use from Medtronic Inc. of Minneapolis, Minn.

As shown in FIG. 99, the positioning tool 606 can further include a securing member 620 that is moveably supported by the tube 612. The securing member 620 can moveably extend out of the distal end 610 of the tube 612. The securing member 620 can be operably connected to a vacuum source 621 such that the securing member 620 can exert a suction force. This suction force allows the securing member 620 to secure the tool 606 to one or more anatomical features, such as an atrial appendage 622. In some embodiments, the securing member 620 can secure the tool 606 to a left atrial appendage 622, but in other embodiments, the securing member 620 can secure the tool 606 to a right atrial appendage 622. Also, the securing member 620 can secure to the atrial appendage 622 in any suitable way other than suction. For instance, as discussed above in relation to FIGS. 1-98C, the securing member 620 can include a hook or barb for hooking the tool 606 onto the atrial appendage 622. The securing member 620 can also include a grasping member for grasping the appendage 622. Also, the securing member 620 can include an adhesive for adhering the tool 606 to the appendage 622.

Moreover, as shown in FIGS. 100 and 101, the system 600 can further include a catheter 626 that is hollow so as to define a lumen 630 extending longitudinally from a proximal end 632 to a distal end 634. Also, as shown in FIG. 100, the system 600 can include a piercing member 628, such as a needle, that is moveably supported within the lumen 630.

Additionally, as shown in FIG. 102, the system 600 can include the electrical lead 602. The electrical lead 602 can be a pacemaker lead for delivering an electrical pacing signal to the heart 604. Also, the electrical lead 602 can be a defibrillation lead for delivering a defibrillation signal to the heart 604. In some embodiments, the lead 602 can be a Model 5076 pacing lead, which is commercially available from Medtronic Inc. of Minneapolis, Minn. The lead 602 can be operably attached to a generator 690 of an implantable medical device that generates the electrical signal transmitted to the heart 604. The lead 602 can also include a distal end 642 that can be connected to the heart 604 as will be discussed.

Thus, during use, the distal end 610 of the tube 612 can be introduced through a chest wall 624 of the patient (FIG. 99). Then, the securing member 620 can moveably extend out of the distal end 610 to secure to the atrial appendage 622 (as shown in phantom in FIG. 99). The securing member 620 can be moved toward the tube 612 such that the appendage 622 is pulled between the arms 616a, 616b, and the arms 616a, 616b can be actuated toward the tube 612 such that the ring 618 recovers and contacts the appendage 622 (FIG. 100). The securing member 620 can be withdrawn from the tube 612 once the ring 618 is secured over the appendage 622, and the arms 616a, 616b can secure the tool 606 to the appendage 622.

Also, as shown in FIG. 100, the catheter 626 can be advanced through the lumen 614 of the tube 612 away from the proximal end 608 to extend partially out of the distal end 610 of the tube 612. The piercing member 628 can be secured in the distal end 634 of the catheter 626 as the catheter 626 advances through the tube 612 and the piercing member 628 can pierce the appendage 622 to create an aperture 640 in the appendage 622. The catheter 626 and piercing member 628 can be extended far enough into the appendage 622 to extend beyond the ring 618 as shown in FIG. 100.

Next, as shown in FIG. 101, the piercing member 628 can be withdrawn from the catheter 626, by pulling the piercing member away from the distal end 634 and out of the proximal end 632. The catheter 626 can remain in position, extending beyond the distal end 610 of the tube 612 and the ring 618. As such, the catheter 626 can remain in position, extending through the appendage 622 of the heart 604.

Subsequently, as shown in FIG. 102, the electrical lead 602 can be moveably supported and advanced through the catheter 626 from the proximal end 632 to extend partially out of the distal end 634 of the catheter 626. As such, the electrical lead 602 can extend through aperture 640 of the appendage 622 and into the heart 604. Once inside the heart 604, the distal end 642 of the lead 602 (e.g., an electrically conductive distal end) can be routed to an intended location within the heart 604. For instance, in some exemplary embodiments, the distal end 642 of the lead 602 can be routed into the left ventricle 644 of the heart 604. Then, the distal end 642 can be mechanically and electrically connected to cardiac tissue within the left ventricle 644.

Also, in some exemplary embodiments, the catheter 626 can be steerable and deflectable and can be used to help steer the electrical lead 602 from the appendage 622 to the left ventricle 644. For instance, the distal end 642 of the lead 602 can be disposed within the catheter 626, and torque forces, pushing forces, and the like can be applied to the proximal end 632 of the catheter 626 to steer the distal end 634 of the catheter 626 into a desired portion of the left ventricle 644. (The distal end 634 of the catheter 626 is shown in phantom in FIG. 102 steered into the left ventricle 644.) Then, the distal end 642 of the lead 602 can be extended out of the catheter 626 to be connected to the desired portion inside the left ventricle 644. In some exemplary embodiments, the catheter 626 can be part of the SOLO-TRAK™ percutaneous lead introducer system, which is commercially available from Medtronic Inc. of Minneapolis, Minn., or other similar lead delivery systems.

Once the electrical lead 602 has been connected, the ring 618 can be detached from the arms 616a, 616b according to one or more of the various exemplary embodiments discussed above in relation to FIGS. 1-98C. Once detached, the ring 618 can substantially occlude the appendage 622 as discussed above.

Also, the catheter 626 and the remaining portions of the tool 606 can be withdrawn from the patient, leaving the electrical lead 602 in place. In some embodiments, the catheter 626 can be slittable or peelable, such that the catheter 626 can be removed from the patient and the lead 602 in a single operation without having to pass over the full length of the lead 602 and without moving the lead 602. The electrical lead 602 can then be connected to the generator 609.

It should also be appreciated that the piercing member 628 may pierce the wall of atrial appendage 622, and the catheter 626 can be advanced into the appendage 622 before securing the ring 618 on the atrial appendage 622. As such, the catheter 626 can be advanced into the heart 604 prior to securing of the ring 618 over the atrial appendage 622 and creating compression around catheter 626. Subsequently, the ring 618 can be secured to the appendage 622.

It will be appreciated that the electrical lead 602 can be connected more easily using the system 600 described above. Also, the lead 602 is less likely to interfere with, for instance, the phrenic nerve because the lead 602 is connected to the interior cardiac tissue of the heart 604.

Referring now to FIGS. 103-105, another exemplary embodiment of the system 700 is illustrated. It will be appreciated that components that correspond to the system 600 of FIGS. 99-102 are indicated with corresponding reference numerals increased by 100.

As shown in FIG. 103, the system 700 can include a securing member 720 with a passage 721 extending longitudinally therethrough. The passage 721 can be used for applying suction to the appendage 722 of the heart 704 to thereby hold the appendage 722.

As shown in FIG. 104, the passage 721 can also be used for passage of the piercing member 728 through the securing member 720. More specifically, while the securing member 720 holds onto the appendage 722, the piercing member 728 can advance through the passage 721 and eventually pierce through the appendage 722 to create the aperture 740.

Next, as shown in FIG. 105, the electrical lead 702 can be advanced through the passage 721, through the aperture 740, and into the heart 704 via the appendage 722. This can occur while the securing member 720 remains secured to the appendage 722. The operative portion 742 of the lead 702 can then be mechanically and electrically connected to cardiac tissue in a predetermined area of the heart 704 (e.g., the left ventricle) as discussed above.

Furthermore, as shown in FIG. 105 an abutment member 760 can be implanted in or on the heart 704. For instance, in some exemplary embodiments, the abutment member 760 can be a ring-shaped sleeve that is mounted adjacent the aperture 740. The abutment member 760 can be advanced through the passage 721 of the securing member 720 as the electrical lead 702 is advanced through the passage 721. Also, in some embodiments, the abutment member 760 can be advanced through the passage 721 either before or after the electrical lead 702 is advanced into the heart 704. In either case, the lumen of the abutment member 760 can receive the electrical lead 702 to be disposed and positioned between the tissue of the heart 704 and the electrical lead 702. As such, the abutment member 760 can inhibit and prevent direct contact between the heart 704 and the lead 702 adjacent the aperture 740. Accordingly, the lead 702 can be moved relative to the heart 704, and the lead 702 is less likely to damage the heart 704. For instance, the lead 702 can rub against the abutment member 760 (as opposed to the tissue of the heart 704 when being withdrawn from the heart 704 when being replaced.

Also, the abutment member 760 may include features (e.g., a flanged outer surface) that mates with the outer surface of heart 704 and promotes tissue in-growth to secure the abutment member 760 within the wall of the heart 704. As such, the abutment member 760 can reinforce the wall of the heart 704 at the location where the lead 702 passes into heart 704. Moreover, the abutment member 760 can include an extension portion 761 that extends partially outside of the heart 704 a sufficient distance to allow a compression device 763 (e.g., a compressive suture, etc.) to be applied around the extension portion 761. The compression device 763 can apply a compression force, F, that is transferred to the lead 702 to thereby hold the lead 702 in place relative to the heart 704.

It will be appreciated that the system 700 shown in FIGS. 103-105 can also include a ring spreader assembly of the type discussed above in relation to FIGS. 1-102. Also, it will be appreciated that the system 700 can include a ring for occluding the appendage 722 as discussed above in relation to FIGS. 1-102. Furthermore, it will be appreciated that the system 700 can include a catheter for steering the lead 702 into position within the heart 704 as discussed above.

Thus, the electrical lead 702 can be connected more easily using the system 700 described above. Also, the lead 702 is less likely to interfere with, for instance, the phrenic nerve because the lead 702 is connected to the interior cardiac tissue of the heart 704. In addition, the electrical lead 702 is less likely to damage the heart 704 when being replaced.

Referring now to FIG. 106, another exemplary embodiment of the system 800 is illustrated. It will be appreciated that components that correspond to the system 700 of FIGS. 103-105 are indicated with corresponding reference numerals increased by 100.

As shown, the abutment member 860 can have a base 871, a neck 873, and a lip 875. The base 871 and lip 875 can be disposed on opposite ends of the neck 873. The base 871 can be relatively flat and annular, the neck 873 can be tubular in shape, and the lip 875 can be annular and can extend away from the axis of the neck 873. Also, the abutment member 860 can include a lumen 877 that extends through each of the base 871, the neck 873, and the lip 875.

Moreover, the abutment member 860 can include a covering member 879. In some embodiments, the covering member 879 can be relatively thin and annular and can cover the base 871, opposite the neck 873. The covering member 879 can be wider than the base 871. In other embodiments, the covering member 879 can cover the entire outer surfaces of the abutment member 860. Also, the covering member 879 can be made out of any suitable material, such as Dacron® polyester.

Furthermore, as shown in FIG. 106, the electrical lead 802 can extend through the lumen 877. Also, the base 871 of the abutment member 860 can be implanted within the atrial appendage 822 while the lip 875 extends out of the appendage 822. As such, the resilient ring 818 can be retained on the neck 873 with the appendage 822 fixed between the ring 818 and the neck 873. Also, the lip 875 can retain the ring 818 on the neck 873 and prevent the ring 818 from sliding off of the neck 873, and the appendage 822 can be held between the lip 875, the neck 873, and the ring 818. Moreover, the ring 818 can compress the neck 873 to thereby hold the lead 802 in place relative to the abutment member 860. Still further, the base 871 can be wide enough such that the base 871 is held against the inner surface of the appendage 822. In addition, the outer portion of the covering member 879 can lie directly on the appendage 822 to promote healing of the appendage 822.

Accordingly, the ring 818 is unlikely to slip off of the appendage 822 due to the shape of the abutment member 860 of FIG. 106. Also, the lead 802 is unlikely to move relative to the abutment member 860 because the ring 818 can hold the lead 802 in place.

Furthermore, other substitutions, modifications, changes, and omissions may be made in the design, operating conditions, and arrangements of the exemplary embodiments without departing from the scope of the invention as expressed in the appended claims. In addition, it will be appreciated by those skilled in the art that while the invention has been described above in connection with particular embodiments and examples, the invention is not necessarily so limited, and that numerous other embodiments, examples, uses, modifications and departures from the embodiments, examples and uses are intended to be encompassed by the claims attached hereto. The entire disclosure of each patent and publication cited herein is incorporated by reference, as if each such patent or publication were individually incorporated by reference herein.

What is claimed is:

1. A system for delivering an electrical lead to a ventricle of a heart of a patient, the system comprising:
   a securing means for securing and holding onto an atrial appendage of the heart;
   a piercing means for piercing and forming an aperture in the atrial appendage while the securing means holds onto the atrial appendage;
   an electrical lead having a distal end, the distal end insertable through the aperture in the atrial appendage and into the left ventricle of the heart, the electrical lead connectable to an implantable cardiac device, the electrical lead delivering an electrical signal to the cardiac tissue to maintain a predetermined heartbeat; and
   an abutment member that is implantable in the heart, the abutment member surrounding the electrical lead and positionable between the heart and the electrical lead to inhibit direct contact between the heart and the electrical lead.

2. The system of claim 1, wherein the securing means includes an adhesive.

3. The system of claim 1, wherein the securing means includes a suction device.

4. The system of claim 1, wherein the securing means includes a passage for passing the distal end of the electrical lead through the securing means.

5. The system of claim 1, wherein the securing means includes a passage for passage of the piercing member through the securing member.

6. The system of claim 1, wherein the abutment member is a sleeve having a lumen that receives the electrical lead.

7. The system of claim 6, further comprising a compression member that compresses the abutment member against the electrical lead to hold the electrical lead in place relative to the abutment member.

8. A system for delivering an electrical lead to a ventricle of a heart of a patient, the system comprising:
   a securing member for securing and holding onto an atrial appendage of the heart;
   a piercing member for piercing and forming an aperture in the atrial appendage while the securing member holds onto the atrial appendage;
   an electrical lead having a distal end, the distal end insertable through the aperture in the atrial appendage and into the left ventricle of the heart, the electrical lead connectable to an implantable cardiac device, the electrical lead delivering an electrical signal to the cardiac tissue to maintain a predetermined heartbeat; and
   an abutment member that is implantable in the heart, the abutment member surrounding the electrical lead and positionable between the heart and the electrical lead to inhibit direct contact between the heart and the electrical lead; and
   wherein the securing means includes a hook.

9. A system for delivering an electrical lead to a ventricle of a heart of a patient, the system comprising:
   a securing member for securing and holding onto an atrial appendage of the heart;

a piercing member means for piercing and forming an aperture in the atrial appendage while the securing member means holds onto the atrial appendage;

an electrical lead having a distal end, the distal end insertable through the aperture in the atrial appendage and into the left ventricle of the heart, the electrical lead connectable to an implantable cardiac device, the electrical lead delivering an electrical signal to the cardiac tissue to maintain a predetermined heartbeat; and an abutment member that is implantable in the heart, the abutment member surrounding the electrical lead and positionable between the heart and the electrical lead to inhibit direct contact between the heart and the electrical lead; and wherein the securing member includes a barb.

10. A system for delivering an electrical lead to a ventricle of a heart of a patient, the system comprising:

a securing member for securing and holding onto an atrial appendage of the heart;

a piercing member for piercing and forming an aperture in the atrial appendage while the securing member holds onto the atrial appendage;

an electrical lead having a distal end, the distal end insertable through the aperture in the atrial appendage and into the left ventricle of the heart, the electrical lead connectable to an implantable cardiac device, the electrical lead delivering an electrical signal to the cardiac tissue to maintain a predetermined heartbeat; and an abutment member that is implantable in the heart, the abutment member surrounding the electrical lead and positionable between the heart and the electrical lead to inhibit direct contact between the heart and the electrical lead; and wherein the securing member includes a grasping member.

11. A system for delivering an electrical lead to a ventricle of a heart of a patient, the system comprising:

a securing means for securing and holding onto an atrial appendage of the heart;

a piercing means for piercing and forming an aperture in the atrial appendage while the securing means holds onto the atrial appendage;

an electrical lead having a distal end, the distal end insertable through the aperture in the atrial appendage and into the left ventricle of the heart, the electrical lead connectable to an implantable cardiac device, the electrical lead delivering an electrical signal to the cardiac tissue to maintain a predetermined heartbeat; and an abutment member that is implantable in the heart, the abutment member surrounding the electrical lead and positionable between the heart and the electrical lead to inhibit direct contact between the heart and the electrical lead; and further comprising a resilient ring able to occlude the atrial appendage.

12. The system of claim 11, further comprising a ring spreader assembly releaseably attached to the resilient ring, the ring spreader assembly including a control for expanding and releasing the resilient ring.

13. A system for delivering an electrical lead to a ventricle of a heart of a patient, the system comprising:

a securing means for securing and holding onto an atrial appendage of the heart;

a piercing means' for piercing and forming an aperture in the atrial appendage while the securing means holds onto the atrial appendage;

an electrical lead having a distal end, the distal end insertable through the aperture in the atrial appendage and into the left ventricle of the heart, the electrical lead connectable to an implantable cardiac device, the electrical lead delivering an electrical signal to the cardiac tissue to maintain a predetermined heartbeat; and an abutment member that is implantable in the heart, the abutment member surrounding the electrical lead and positionable between the heart and the electrical lead to inhibit direct contact between the heart and the electrical lead; and wherein the abutment member is a sleeve having a lumen that receives the electrical lead and; and wherein the abutment member includes a base, a neck, and a lip, the base insertable into the atrial appendage to be held against the atrial appendage, the lip extendable out of the atrial appendage, and further comprising a compression member that compresses the neck of the abutment member, the lip retaining the compression member on the neck.

* * * * *